(12) United States Patent
Farina et al.

(10) Patent No.: US 12,128,174 B1
(45) Date of Patent: Oct. 29, 2024

(54) DEVICES AND METHODS FOR USING MEDICAMENT DEVICES

(71) Applicant: PROVERIS SCIENTIFIC CORPORATION, Hudson, MA (US)

(72) Inventors: Susan Hanmer Farina, Sudbury, MA (US); Dino John Farina, Sudbury, MA (US)

(73) Assignee: PROVERIS SCIENTIFIC CORPORATION, Hudson, MA (US)

( * ) Notice: Subject to any disclaimer, the term of this patent is extended or adjusted under 35 U.S.C. 154(b) by 0 days.

(21) Appl. No.: 18/604,209

(22) Filed: Mar. 13, 2024

Related U.S. Application Data

(63) Continuation of application No. 16/200,435, filed on Nov. 26, 2018, now abandoned, which is a
(Continued)

(51) Int. Cl.
*A61M 15/00* (2006.01)
(52) U.S. Cl.
CPC . *A61M 15/0001* (2014.02); *A61M 2205/3334* (2013.01); *A61M 2205/3584* (2013.01);
(Continued)
(58) Field of Classification Search
CPC ...... A61M 15/0001; A61M 2205/3334; A61M 2205/3584; A61M 2205/581; A61M 2205/583; A61M 2230/40
See application file for complete search history.

(56) References Cited

U.S. PATENT DOCUMENTS 5,363,842 A    11/1994   Mishelevich et al.
5,505,192 A *   4/1996   Samiotes ............ A61M 15/009
                                                       128/200.14
(Continued)

FOREIGN PATENT DOCUMENTS

CN     102245240 A    11/2011
CN     102695535 A     9/2012
(Continued)

OTHER PUBLICATIONS

Apter, et al., Testing the reliability of old and new features of a new electronic monitor for metered dose inhalers; Annals of Allergy, Asthma, & Immunology, Apr. 2001, 421-424.
(Continued)

*Primary Examiner* — Kendra D Carter
*Assistant Examiner* — Jaeick Jang
(74) *Attorney, Agent, or Firm* — Wilson Sonsini Goodrich & Rosati

(57) ABSTRACT

Disclosed herein are devices and methods for the use of medicament devices. The devices and methods may be used to detect or sense one or more parameters of a medicament device, for instance, shake parameters, actuation parameters, or inhalation airflow parameters. The devices and methods may be used to indicate to a user that the medicament device is in an appropriate condition for actuation of the medicament device. The devices and methods may be used to indicate to a user that the medicament device is in a condition to deliver an intended dosage range of a formulation. The devices and methods may further be used to guide a user through proper usage of a medicament device.

25 Claims, 30 Drawing Sheets

Related U.S. Application Data continuation of application No. PCT/US2017/034824, filed on May 26, 2017.

(60) Provisional application No. 62/465,701, filed on Mar. 1, 2017, provisional application No. 62/439,595, filed on Dec. 28, 2016, provisional application No. 62/342,843, filed on May 27, 2016.

(52) U.S. Cl.
CPC . *A61M 2205/581* (2013.01); *A61M 2205/583* (2013.01); *A61M 2230/40* (2013.01)

(56) References Cited

U.S. PATENT DOCUMENTS

| | | | |
|---|---|---|---|
| 5,538,002 | A | 7/1996 | Boussignac et al. |
| 6,202,642 | B1 | 3/2001 | McKinnon et al. |
| 6,997,906 | B2 | 2/2006 | Langley et al. |
| 7,100,839 | B2 | 9/2006 | Farina et al. |
| 7,658,122 | B2 | 2/2010 | Farina et al. |
| 7,748,382 | B2 | 7/2010 | Denyer et al. |
| 8,172,082 | B2 | 5/2012 | Edwards et al. |
| 8,357,114 | B2 | 1/2013 | Poutiatine et al. |
| 8,424,517 | B2 | 4/2013 | Sutherland et al. |
| 8,539,945 | B2 | 9/2013 | Solomon et al. |
| 8,807,131 | B1 * | 8/2014 | Tunnell ............. A61M 15/0021 128/200.14 |
| 9,035,765 | B2 | 5/2015 | Engelhard et al. |
| 9,149,589 | B2 | 10/2015 | Meyer et al. |
| 9,364,619 | B2 | 6/2016 | Overfield et al. |
| 9,427,534 | B2 | 8/2016 | Bruin et al. |
| 9,626,481 | B2 | 4/2017 | Solomon et al. |
| 9,728,068 | B2 | 8/2017 | Engelhard et al. |
| 9,782,551 | B2 | 10/2017 | Morrison et al. |
| 9,911,308 | B2 | 3/2018 | Edwards et al. |
| 9,937,305 | B2 | 4/2018 | Morrison |
| 9,962,508 | B2 | 5/2018 | Bruin et al. |
| 2003/0140921 | A1 * | 7/2003 | Smith ............... A61M 15/0031 128/200.14 |
| 2009/0157037 | A1 | 6/2009 | Iyer et al. |
| 2009/0308387 | A1 | 12/2009 | Andersen et al. |
| 2010/0116070 | A1 | 5/2010 | Farina et al. |
| 2011/0265806 | A1 | 11/2011 | Alarcon et al. |
| 2011/0270541 | A1 | 11/2011 | Cha et al. |
| 2012/0291779 | A1 | 11/2012 | Haartsen et al. |
| 2013/0008436 | A1 | 1/2013 | Von Hollen et al. |
| 2013/0037027 | A1 * | 2/2013 | Schuller ............ A61M 16/0063 128/205.12 |
| 2013/0269685 | A1 | 10/2013 | Wachtel et al. |
| 2015/0004582 | A1 | 1/2015 | Baker et al. |
| 2015/0100276 | A1 * | 4/2015 | Huang ................ A61M 15/009 702/187 |
| 2015/0100335 | A1 | 4/2015 | Englehard et al. |
| 2015/0112707 | A1 | 4/2015 | Manice et al. |
| 2015/0156567 | A1 | 6/2015 | Oliver et al. |
| 2015/0174349 | A1 | 6/2015 | Tunnell et al. |
| 2015/0245660 | A1 | 9/2015 | Lord |
| 2015/0259110 | A1 | 9/2015 | Blackburn |
| 2015/0290396 | A1 | 10/2015 | Nagar et al. |
| 2015/0335834 | A1 | 11/2015 | Anandhakrishnan |
| 2015/0374939 | A1 | 12/2015 | Meyer et al. |
| 2015/0377749 | A1 | 12/2015 | Farina et al. |
| 2016/0007913 | A1 | 1/2016 | Darket |
| 2016/0082208 | A1 | 3/2016 | Ballam et al. |
| 2016/0113568 | A1 | 4/2016 | Macchi |
| 2016/0129182 | A1 | 5/2016 | Schuster et al. |
| 2016/0144141 | A1 | 5/2016 | Biswas et al. |
| 2016/0235916 | A1 | 8/2016 | Edwards et al. |
| 2016/0256640 | A1 | 9/2016 | Overfield et al. |
| 2017/0132391 | A1 | 5/2017 | Morrison |
| 2017/0173279 | A1 | 6/2017 | Sutherland et al. |
| 2017/0290527 | A1 | 10/2017 | Morrison et al. |
| 2017/0323553 | A1 | 11/2017 | Engelhard et al. |
| 2018/0085540 | A1 | 3/2018 | Dantsker et al. |
| 2018/0151053 | A1 | 5/2018 | Edwards et al. |
| 2018/0200460 | A1 | 7/2018 | Ziegler et al. |
| 2018/0207373 | A1 | 7/2018 | Morrison |
| 2018/0264207 | A1 | 9/2018 | Von Hollen et al. |
| 2018/0304018 | A1 | 10/2018 | Blondino et al. |
| 2019/0224426 | A1 | 7/2019 | Farina et al. |

FOREIGN PATENT DOCUMENTS

| | | | |
|---|---|---|---|
| CN | 103228306 A | 7/2013 | |
| CN | 103347553 A | 10/2013 | |
| CN | 105377346 A | 3/2016 | |
| EP | 1581291 B1 | 1/2009 | |
| EP | 2047881 B1 | 8/2010 | |
| EP | 2414978 A1 | 2/2012 | |
| EP | 2300083 B1 | 5/2013 | |
| EP | 2609954 A2 | 7/2013 | |
| EP | 2908674 A1 | 8/2015 | |
| EP | 3038687 A1 | 7/2016 | |
| EP | 3111978 A1 | 1/2017 | |
| EP | 2414978 B1 | 12/2018 | |
| EP | 3038687 B1 | 2/2019 | |
| GB | 2263068 B | 5/1996 | |
| GB | 2547279 A | 8/2017 | |
| GB | 2548009 A | 9/2017 | |
| WO | WO-2005028008 A1 | 3/2005 | |
| WO | WO-2010067240 A1 | 6/2010 | |
| WO | WO-2011083377 A1 | 7/2011 | |
| WO | WO-2012072541 A1 | 6/2012 | |
| WO | WO-2012072563 A1 | 6/2012 | |
| WO | WO-2015004554 A1 | 1/2015 | |
| WO | WO-2015109259 A1 | 7/2015 | |
| WO | WO-2016030521 A1 | 3/2016 | |
| WO | WO-2016033418 A1 | 3/2016 | |
| WO | WO-2016033421 A1 * | 3/2016 | ............ A61B 5/087 |
| WO | WO-2016116591 A1 | 7/2016 | |
| WO | WO-2017005605 A1 | 1/2017 | |
| WO | WO-2017141033 A1 | 8/2017 | |
| WO | WO-2017178865 A1 | 10/2017 | |
| WO | WO-2017199215 A1 | 11/2017 | |
| WO | WO-2017201463 A1 | 11/2017 | |
| WO | WO-2017205824 A1 | 11/2017 | |

OTHER PUBLICATIONS

Asthma Facts, Center for Disease Control, Jul. 2013, pp. 1-15.
Asthma's Impact on the Nation, Center for Disease Control, pp. 1-4.
Cost of COPD, Propeller Health, 2014, pp. 2-10.
Extended European Search Report dated Feb. 12, 2020, for EP Appl. No. 17803720.6.
Farina, et al. A Shaking Control Space Study for a Fluticasone/Salmeterol Metered Dose Inhaler Based on Spray Pattern Analysis. Proveris Scientific Corporation, 2013.
Fink et al. Problems with Inhaler Use: A Call for Improved Clinician and Patient Education, Respiratory Care, 50.10 (Sep. 2005): 1360-1375.
Giraud et al. Misuse of corticosteroid metered-dose inhaler is associated with decreased asthma stability, European Respiratory Journal, (2002): 246-251.
GlaxoSmithKline Highlights of prescribing information for Ventolin HFA (albuterol sulfate) Inhalation Aerosol. Dec. 31, 2014. pp. 1, 22-23.
Ibrahim, et al. Inhalation drug delivery devices: Technology Update, Med Devices Auckland 8 (2015): 131-139.
Kelly, Shake Well Before Dispensing, PharmaD, Pharmacy Times, Sep. 28, 2015, 1-3.
McEvoy, Mike, Alburterol (Ventolin): Drug Whys, EMSL.com.
Myrdal et al. Advances in Metered Dose Inhaler Technology: Formulation Development. AAPS Pharma Sci Tech., 15.2 (Apr. 2014): 434-44.
Al-Jahdali, et al., Improper inhaler technique is associated with poor asthma control and more frequent emergency department visits, Asthma & Clinical Immunology 2013, 9:8.
Newcomb, et al. How critical quality attributes and process variables drive the in-vitro performance of pMDIs: new technologies and methods; Proveris Scientific Corporation, 2015.

(56) References Cited

OTHER PUBLICATIONS

Newcomb et al., Understanding the importance and effects of shaking on pMDI performance, Proveris Scientific Corporation, DDL Poster, 2015.
Nicolini., Beclomethasone/Formoterol fixed combination for the management of asthma: patient considerations. Ther Clin Risk Manag, 4.5 (2008): 855-864.
PCT/US2017/034824 International Search Report and Written Opinion dated Oct. 13, 2017.
Pitluk et al., A Shaking Control Space for Fluticasone Propionate Nasal Spray DCU Testing. Proveris Scientific Corporation, 2012.
Saxena, Study: Patients don't know how to use drug delivery devices. www.fiercedrugdelivery.com, Dec. 17, 2014, 1-2.
Scichilone, et al. Patient perspectives in the management of asthma: improving patient outcomes through critical selection of treatment options, Patent Preference and Adherence, 4 (2010): 17-23.
Terzano, Pressurized metered Dose Inhalers and Add-on Devices, Pulmonary Pharmacology & Therapeutics, 14 (2001): 351-366.
U.S. Appl. No. 16/200,435 Office Action dated Feb. 16, 2023.
U.S. Appl. No. 16/200,435 Office Action dated Jul. 22, 2020.
U.S. Appl. No. 16/200,435 Office Action dated May 24, 2022.
U.S. Appl. No. 16/200,435 Office Action dated Sep. 13, 2023.
U.S. Appl. No. 16/200,435 Office Action dated Sep. 21, 2021.
Virchow et al. A review of the value of innovation in inhalers for COPD and asthma, Journal of Market Access & Health Policy, Sep. 2015.

\* cited by examiner

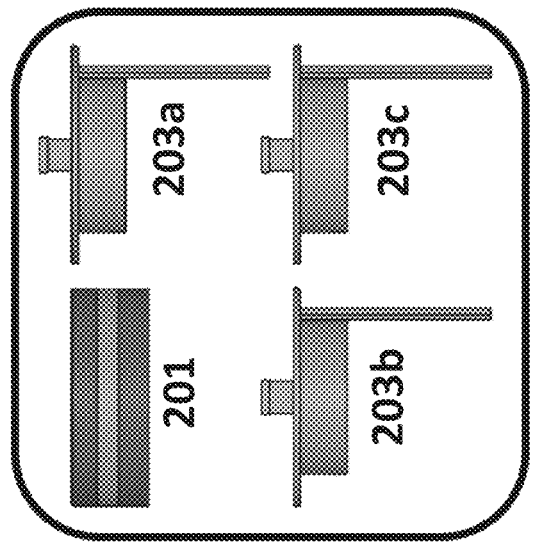
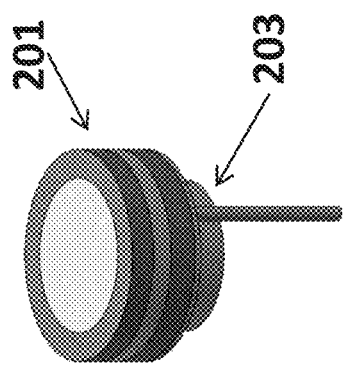
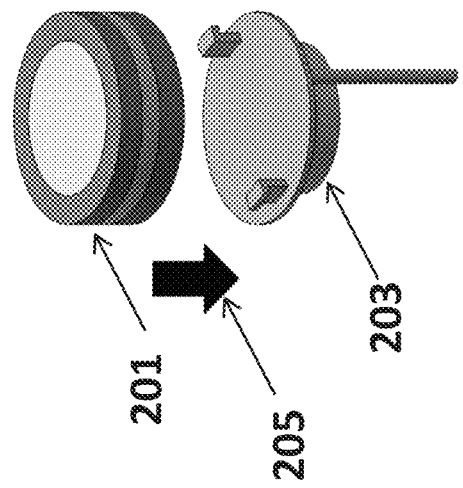
FIG. 2B
FIG. 2A

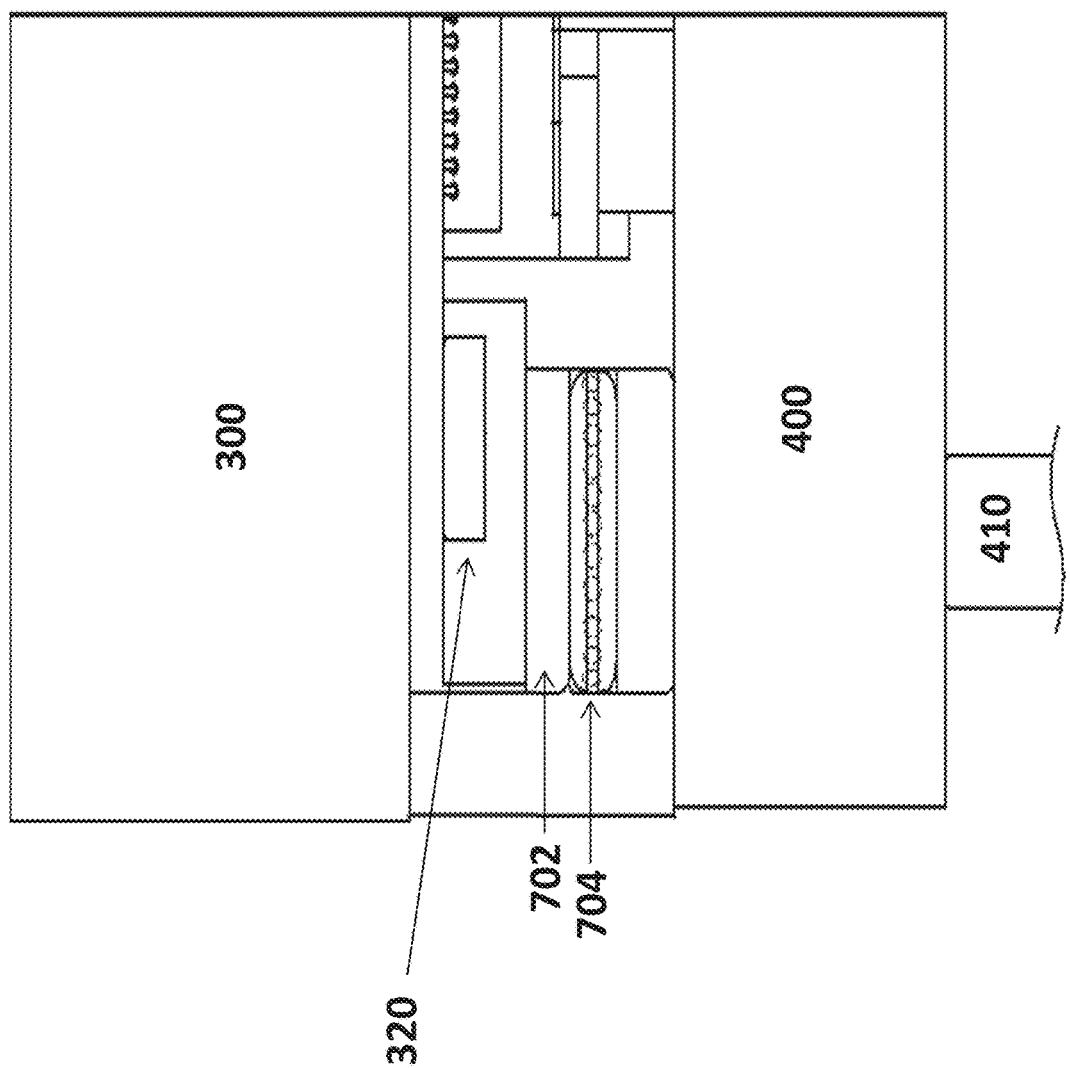

FIG. 9

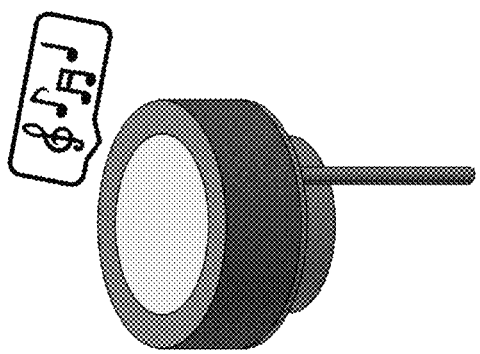
FIG. 12B
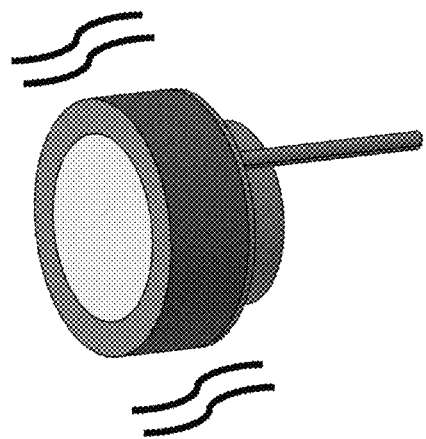
FIG. 12D
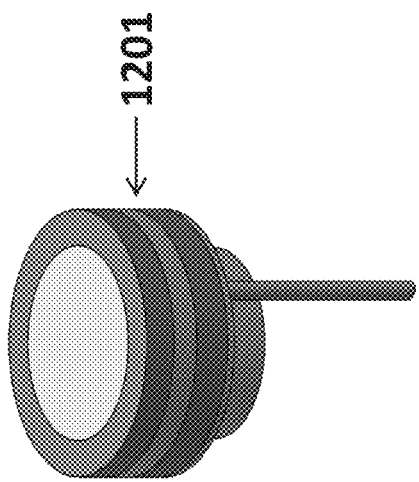
FIG. 12A
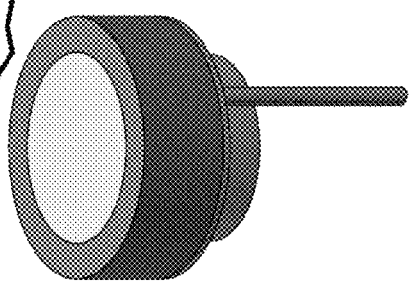
FIG. 12C

DEVICES AND METHODS FOR USING MEDICAMENT DEVICES

CROSS REFERENCE

This application is a continuation application of U.S. patent application Ser. No. 16/200,435, filed on Nov. 26, 2018, now abandoned, which is a continuation application of International Patent Application No. PCT/US2017/034824, filed on May 26, 2017, which claims the benefit of U.S. Provisional Application No. 62/342,843, filed on May 27, 2016; U.S. Provisional Application No. 62/439,595, filed on Dec. 28, 2016; and U.S. Provisional Application No. 62/465,701, filed on Mar. 1, 2017, each of which is incorporated by reference herein in its entirety.

BACKGROUND OF THE INVENTION

Inhaler and nasal devices may require specific handling such as proper shaking and proper actuation in order to release an intended dosage range of a drug. Poor handling by caregivers and patients and improper inhalation technique is associated with overdosed medication delivery and decreased medication delivery, and poor disease control. User error of inhaler and nasal devices is a critical public health concern and it is estimated that up to 92% of patients using pressurized metered dose inhalers (pMDIs) and up to 54% of patients using dry powder inhalers may be using their inhalers incorrectly. Correct inhaler technique involves some common steps for all devices (e.g., dose preparation, device orientation, full exhalation, deep inhalation, and breath hold). However, dose preparation, such as priming and re-priming the device, shaking the device, and device orientation differ between devices. Furthermore, the characteristics of the device and the formulation of the drug, each of which vary between products, may be important factors in determining the correct handling technique to ensure an intended dosage of drug is being delivered. Moreover, usage instructions such as "shake well" or "shake for 5 seconds," are interpreted differently in practice among device users adding to dosage problems caused by improper dose preparation and device use technique. Similar types of errors may occur with caregivers and patients using nasal devices to deliver a drug formulation.

SUMMARY OF THE INVENTION

In one aspect, a sensor device is provided for guiding usage of a medicament device, the sensor device comprising: a coupler for coupling to the medicament device, wherein the medicament device is selected from a plurality of different types of medicament devices; one or more sensors for detecting use of the medicament device; a processor configured to: automatically process one or more parameters associated with the medicament device; and output a signal based on the one or more parameters; and an indicator configured to: operably receive the signal; and output a guidance to a user of the medicament device, wherein the guidance varies depending on a type of medicament device that is selected. The guidance may vary in a duration of shaking a medicament device, a shake-to-fire interval, a wait time between actuations, a number of priming steps, a number of re-priming steps, and a duration until re-priming steps. The duration of shaking the medicament device may vary between 0 and 30 seconds. The wait time between actuations may vary between 0 to 60 seconds. The number of priming steps may vary between 0 and 5. The number of re-priming steps may vary between 0 and 5. The duration until re-priming steps may vary between 0 and 30 days. The shake-to-fire interval may vary from 0 to 30 seconds. The guidance may comprise an auditory indication. The guidance may comprise a visual indication. The coupler may comprise a receiving port. The receiving port may comprise an electrical interface. The receiving port may be configured to removably receive a complementary protrusion of an adapter comprising a memory storing the one or more parameters associated with the medicament device. The coupler may comprise one or more latch points for receiving one or more latches of an adapter comprising an adhesive configured to couple to the medicament device. The sensor device may be configured to be used with 5 or more different types of medicament devices. The sensor device may be configured to be used for a duration of more than 6 months. The one or more sensors may comprise an accelerometer, a barometer, a temperature sensor, a magnetometer, an ambient light sensor, or a global positioning system (GPS). The one or more sensors may comprise the accelerometer, and the accelerometer may be configured to be located along a central axis of the medicament device. The barometer may be located in a pressure sensing cavity. The pressure sensing cavity may allow a bidirectional flow of air in and out of the pressure sensing cavity. The bidirectional flow of air may be through a single opening in the pressure sensing cavity. The pressure sensing cavity may comprise a volume of approximately 10 $mm^3$. The pressure sensing cavity may comprise an opening for coupling to a pressure tap tube. The sensor device may comprise an element for turning the sensor device on or off. The element may be located at a proximal end of the sensor device. The indicator may comprise a speaker. The indicator may comprise a light emitting diode (LED). The indicator may comprise a visual display. The sensor device may comprise an interface for communicating with an external device. The sensor device may comprise a size of approximately 10 $cm^3$. The medicament device may comprise a canister used with an inhaler. The inhaler may be is a pressurized dose metered inhaler.

In another aspect, a kit is provided comprising: a sensor device of any of the above, and instructions for coupling and/or decoupling the sensor device to an adapter comprising a memory storing the one or more parameters associated with the medicament device.

In another aspect, an adapter is provided for guiding usage of a medicament device, the adapter comprising: a first coupler for coupling to the medicament device; a memory storing one or more parameters associated with the medicament device; and a second coupler for coupling to a sensor device, wherein the sensor device is configured to output a guidance to a user of the medicament device. In another aspect, a kit is provided comprising: the adapter; and instructions for coupling and/or decoupling the adapter to a medicament device selected from a plurality of different types of medicament devices. The adapter may be configured to guide usage of a single type of medicament device. The second coupler may comprise a protrusion. The protrusion may comprise an electrical interface. The protrusion may be complementary to a receiving port of a sensor device comprising one or more sensors for detecting use of the medicament device. The first coupler may comprise an adhesive. The adapter may further comprise one or more processors operably coupled to the memory. The adapter may comprise a pressure tap tube. The pressure tap tube may be hollow. The pressure tap tube may comprise a proximal portion located on a first surface of the adapter and a distal portion located away from a second surface opposite the first surface. The proximal portion may comprise a sealing element. The sealing element may be an "O" ring. The distal portion may comprise one or more holes. The one or more holes may be located on a side surface of the pressure tap tube. The pressure tap tube may be configured to run alongside a longitudinal axis of the medicament device. The adapter may comprise an authenticator. The authenticator may be configured to authenticate the sensor device and/or the adapter. The adapter may be configured to couple to the sensor device via a snap on mechanism. The adapter may be configured to be used for at least 60 actuations. The medicament device may comprise a canister used with an inhaler.

In yet another aspect, a method is provided for using a sensor device configured to couple to a plurality of different types of medicament devices, the method comprising: coupling the sensor device to a first medicament device; processing one or more parameters associated with the first medicament device; guiding usage of the first medicament device based on the processed one or more parameters associated with the first medicament device; decoupling the sensor device from the first medicament device; coupling the sensor device to a second medicament device, wherein the second medicament device differs in a type of medicament device from the first medicament device; processing one or more parameters associated with the second medicament device; and guiding usage of the second medicament device based on the processed one or more parameters associated with the second medicament device, wherein guiding usage of the second medicament device differs from guiding usage of the first medicament device. Guiding usage of the second medicament device may differ from guiding usage of the first medicament device in a duration of shaking a medicament device, a shake-to-fire interval, a wait time between actuations, a number of priming steps, a number of re-priming steps, or a duration until re-priming steps. The duration of shaking the medicament device may vary between 0 and 30 seconds. The wait time between actuations may vary between 0 to 60 seconds. The number of priming steps may vary between 0 and 5. The number of re-priming steps may vary between 0 and 5. The duration until re-priming steps may vary between 0 and 30 days. The shake-to-fire interval may vary between 0 and 30 seconds. Coupling the sensor device to the first medicament device may comprise coupling the sensor device to a first adapter coupled to the first medicament device, wherein the first adapter comprises a first memory storing a first set of parameters associated with the first medicament device. Coupling the sensor device to the second medicament device may comprise coupling the sensor device to a second adapter coupled to the second medicament device, wherein the second adapter comprises a second memory storing a second set of parameters associated with the second medicament device, wherein the second set of parameters differs from the first set of parameters. The medicament device may comprise a canister used with an inhaler.

In another aspect, a method is provided for measuring usage of an inhaler using one or more sensors, the method comprising: with aid of the one or more sensors: measuring a duration of shaking the inhaler; measuring a duration of a time subsequent to the shaking; measuring an inhalation of a user using inhaler; measuring an actuation of the inhaler; and measuring a duration of a hold down time of the actuation. The one or more sensors may output an indication subsequent to each measuring step when a predetermined threshold has been reached. The output may be a visual output that indicates to the user of the inhaler to move onto a next step. The output may be an auditory output that indicates to the user of the inhaler to move onto a next step. The one or more sensors may be further configured to measure an orientation of the inhaler. The sensor may output an indication of an incorrect orientation when the inhaler is outside a predetermined orientation. The one or more sensors may be further configured to track a remaining number of actuations for the inhaler. The sensor may output an indication of a low number of dosages remaining for the inhaler when the inhaler is at or below a predetermined number of dosages remaining. The one or more sensors may comprise an accelerometer, a barometer, a temperature sensor, a magnetometer, an ambient light sensor, or global positioning system (GPS). The inhaler may comprise a medicament device. The medicament device may be a canister of the inhaler. The one or more sensors may comprise a sensor located external to the inhaler. The one or more sensors may be located on a mobile device.

In another aspect, a device is provided for monitoring usage of a medicament device, the device comprising: a) an adapter, wherein the adapter comprises a memory storing a set of parameters specific to a type of the medicament device; and b) a sensor device separable from, and in operable communication with the adapter, wherein the sensor device is configured to be used with a plurality of different types of adapters each comprising a unique set of parameters specific to different types of medicament devices, wherein the device is configured to produce an output based on the set of parameters. The device may further comprise the medicament device. The medicament device may be a canister used with an inhaler. The adapter may be configured to couple to an exterior of the canister, and the sensor device may be configured to couple indirectly to the canister via the adapter. The sensor device may comprise an accelerometer configured to be located along a central line axis of the medicament device when the adapter and the sensor device are coupled to the medicament device. The sensor device may comprise a pressure sensing cavity comprising a single opening. The adapter may comprise a pressure tap tube configured to couple to the single opening. The pressure sensing cavity may comprise a barometer. The sensor device may comprise a receiving port, and the adapter may comprise a protrusion complementary to the receiving port. The receiving port and the protrusion may each comprise an electrical interface. The output may be a feedback provided to a user based on usage of the medicament device. The feedback may guide the user on how to properly administer the medicament device in real-time. The output may be produced when at least one of the set of parameters has met a predetermined threshold. The output may be produced when at least one of the set of parameters is outside a threshold range. The sensor device may be configured to be operable with one or more different medicament devices. The sensor device may be reusable. The adapter may be disposable. The medicament device may be used with an inhaler or nasal device. The inhaler or nasal device may be a pressurized metered dose inhaler (pMDI) or a dry powder inhaler. The set of parameters may comprise one or more shake parameters. The one or more shake parameters may comprise: shake duration, shake angle, shake frequency, shake-to-fire interval, shake orientation, and any combination thereof. The set of parameters may comprise one or more actuation parameters. The one or more actuation parameters may comprise: compression velocity, compression acceleration, actuation hold time, decompression velocity, decompression acceleration, actuation stroke length, and any combination thereof. The set of parameters may comprise one or more inhalation airflow parameters. The one or more inhalation airflow parameters may comprise: inspiratory airflow rate, inhaled volume, inflow velocity, and any combination thereof. The medicament device may contain a formulation of a drug. The output may be produced when at least one of the set of parameters has met a predetermined threshold, and the predetermined threshold may be determined based on a composition of the formulation of a drug, one or more characteristics of the medicament device, or both. The formulation may comprise one or more excipients. The formulation may comprise no excipients. The adapter may be affixed to a housing or a canister of the medicament device. The adapter may be permanently affixed to a surface of the housing or canister. The adapter may be removably affixed to a surface of the housing or canister. The sensor device may be affixed to the adapter. The one or more outputs may comprise a visual indication, an audible indication or both. The visual indication may comprise: a presence or absence of a light, a color change of a light, a flashing of a light, and any combination thereof. The visual indication may be produced by a light-emitting diode (LED). The visual indication may be produced by a LCD or LED display. The output may comprise data. The data may be collected and stored by the device. The data may be transmitted to or read from a mobile device, a computer, a cloud application, or any combination thereof. The one or more sensors may be selected from the group comprising: an accelerometer, a barometer, a temperature sensor, a magnetometer, an ambient light sensor, or a global positioning system (GPS).

In yet another aspect, a method is provided for using an inhaler or nasal device with aid of a sensor, the method comprising: a) shaking the inhaler or nasal device; b) measuring a shake-to-fire interval for actuating the inhaler or nasal device using the sensor; c) actuating the inhaler or nasal device when the sensor produces an output, wherein when the sensor detects a beginning of the shake-to-fire interval, the sensor produces the output.

In another aspect, a method is provided for using an inhaler or nasal device with aid of a sensor, the method comprising: a) compressing the inhaler or nasal device for a period of time, wherein the period of time comprises an actuation hold time window; and b) decompressing the inhaler or nasal device when the sensor produces an output, wherein when the sensor detects an end of the actuation hold time window, the sensor produces the output.

In another aspect, a device is provided for monitoring usage of a medicament device comprising: a) an adapter comprising: a distal end comprising a first adapter coupler for coupling to the medicament device; a memory storing one or more parameters associated with the medicament device; a proximal end comprising a second adapter coupler for coupling to a sensor device, wherein the second adapter coupler comprises a protrusion comprising an electrical interface; and a pressure tap tube, wherein the pressure tap tube comprises a first end on the proximal end side of the adapter and a second end located distally away from the distal end side of the adapter; and b) a sensor device removably coupled to the adapter, wherein the sensor device comprises: a mating surface for mating with the proximal end of the adapter, comprising: a receiving port comprising an electrical interface, wherein the receiving port is complementary to the protrusion and is configured to receive the protrusion; and an opening configured to receive the first end of the pressure tap tube; a pressure sensing cavity operably coupled to the opening, the pressure sensing cavity defining an enclosed chamber with the opening and comprising a barometer; a processor operably coupled to the receiving port, the processor configured to: receive the one or more parameters associated with the medicament device from the adapter; automatically process the one or more parameters associated with the medicament device; and output a signal based on the one or more parameters; and an indicator configured to: operably receive the signal; and output a guidance to a user of the medicament device, wherein the guidance varies depending on the one or more parameters that is received.

In another aspect, a kit is provided comprising: a sensor device according to any of the above; an adapter according to any of the above; and instructions for coupling and/or decoupling the sensor device and the adapter to a medicament device selected from a plurality of different types of medicament devices.

In one aspect, a system is provided comprising a sensor for detecting one or more parameters of an inhaler or nasal device, wherein the sensor is in contact with the inhaler or nasal device and wherein the system produces one or more outputs when each of at least one of the one or more parameters has met a predetermined threshold. In some cases, when each of at least one of the one or more parameters has met a predetermined threshold, the inhaler or nasal device, when actuated, delivers an intended dosage range of a drug. In some cases, the one or more parameters comprises one or more shake parameters. In some examples, the one or more shake parameters are selected from the group consisting of: shake duration, shake angle, shake frequency, shake-to-fire interval, and any combination thereof. In some instances, the one or more parameters comprise one or more actuation parameters. In some examples, the one or more actuation parameters is selected from the group consisting of: compression velocity, compression acceleration, actuation hold time, decompression velocity, decompression acceleration, actuation stroke length, and any combination thereof. In some instances, the one or more parameters comprises one or more inhalation airflow parameters. In some examples, the one or more inhalation airflow parameters is selected from the group consisting of: inspiratory airflow rate, inhaled volume, inflow velocity, and any combination thereof. In some cases, the inhaler or nasal device is a pressurized metered dose inhaler (pMDI) or a dry powder inhaler. In some cases, the inhaler or nasal device contains a formulation of a drug. In some cases, the predetermined threshold is determined based on a composition of the formulation of a drug, one or more characteristics of the inhaler or nasal device, or both. In some cases, the formulation comprises one or more excipients. In some cases, the formulation comprises no excipients. In some cases, the sensor is affixed to a holder or a canister of the inhaler or nasal device. In some cases, the sensor is permanently affixed to the holder or canister. In some cases, the sensor is removably affixed to the holder or canister. In some cases, the sensor is affixed to a surface of the holder or canister. In some cases, the sensor is embedded into the holder or canister. In some cases, the one or more outputs comprises an indication. In some cases, the indication is a visual indication, an audible indication or both. In some cases, the visual indication is selected from the group consisting of: a presence or absence of a light, a color change of a light, a flashing of a light, and any combination thereof. In some examples, the indication is produced by a light-emitting diode (LED). In some cases, the sensor is operably coupled to the inhaler or nasal device. In some cases, the one or more outputs comprises data. In some cases, the data is collected and stored by the sensor. In some cases, the data is transmitted to or read from a mobile device, a computer, a cloud application, or any combination thereof.

In another aspect, a system is provided comprising a sensor for detecting a shake-to-fire interval for actuating an inhaler or nasal device, wherein the sensor is in contact with the inhaler or nasal device and wherein when the sensor detects the shake-to-fire interval, the system produces one or more outputs. In some cases, the shake-to-fire interval indicates a period of time during which the inhaler or nasal device, when actuated, delivers an intended dosage range of a drug. In some cases, the shake-to-fire interval comprises a first time point at the start of the shake-to-fire interval and a second time point at the end of the shake-to-fire interval. In some cases, the inhaler or nasal device contains a formulation of a drug. In some cases, the shake-to-fire interval is determined based on a composition of the formulation of a drug, one or more characteristics of the inhaler or nasal device, or both. In some cases, the formulation comprises one or more excipients. In some cases, the formulation comprises no excipients. In some cases, the one or more outputs comprises an indication. In some cases, the one or more outputs is produced when the first time point is reached. In some cases, one or more additional outputs is produced when second time point is reached. In some cases, the indication is a visual indication, audible indication or both. In some cases, the visual indication is selected from the group consisting of: a presence or absence of a light, a color change of a light, a flashing of a light, and any combination thereof. In some cases, the visual indication is produced by a light-emitting diode (LED). In some cases, the sensor further detects one or more parameters of the inhaler or nasal device. In some cases, the one or more parameters comprises one or more shake parameters. In some cases, the shake-to-fire interval is a period of time after a predetermined threshold of the one or more parameters is met. In some examples, the one or more shake parameters is selected from the group consisting of: shake duration, shake angle, shake frequency, shake-to-fire interval, and any combination thereof. In some cases, the sensor is operably coupled to the inhaler or nasal device. In some cases, the inhaler or nasal device cannot be actuated outside of the shake-to-fire interval. In some cases, the inhaler or nasal device is automatically actuated when the shake-to-fire interval is detected. In some cases, the inhaler or nasal device is automatically actuated when the one or more outputs is produced. In some cases, the sensor is affixed to a holder or a canister of the inhaler or nasal device. In some cases, the sensor is permanently affixed to the holder or canister. In some cases, the sensor is removably affixed to the holder or canister. In some cases, the sensor is affixed to a surface of the holder or canister. In some cases, the sensor is embedded into the holder or canister. In some cases, the inhaler or nasal device is a pressurized metered dose inhaler (pMDI) or a dry powder inhaler. In some cases, the one or more outputs comprises data. In some cases, the data is collected and stored by the sensor. In some cases, the data is transmitted to or read from a mobile device, a computer, a cloud application or any combination thereof.

In another aspect, a method is provided for using an inhaler or nasal device comprising a system, wherein the system comprises a sensor in contact with the inhaler or nasal device, the method comprising: a) shaking the inhaler or nasal device, wherein the shaking comprises one or more shake parameters; and b) actuating the inhaler or nasal device when a predetermined threshold of the one or more shake parameters is met, wherein when the sensor detects the predetermined threshold has been met, the system produces one or more outputs. In some instances, the one or more shake parameters is selected from the group consisting of: shake duration, shake angle, shake frequency, shake-to-fire interval, and any combination thereof. In some cases, the one or more outputs comprise an indication. In some cases, the indication is a visual indication, an audible indication or both. In some cases, the actuating releases an intended dosage of a drug. In some cases, the method further comprises during the actuating, the sensor or an additional sensor detects one or more actuation parameters. In some cases, when the sensor or the additional sensor detects a predetermined threshold of the one or more actuation parameters, the system produces one or more additional outputs. In some cases, the one or more actuation parameters is selected from the group consisting of: compression velocity, compression acceleration, actuation hold time, decompression velocity, decompression acceleration, actuation stroke length, and any combination thereof. In some cases, the inhaler or nasal device is a pressurized metered dose inhaler (pMDI) or a dry powder inhaler. In some cases, the inhaler or nasal device contains a formulation of a drug. In some cases, the predetermined threshold is determined based on a composition of the formulation of a drug, one or more characteristics of the inhaler or nasal device, or both. In some cases, the formulation comprises one or more excipients. In some cases, the formulation comprises no excipients. In some cases, the sensor is affixed to a holder or a canister of the inhaler or nasal device. In some cases, the sensor is permanently affixed to the holder or canister. In some cases, the sensor is removably affixed to the holder or canister. In some cases, the sensor is affixed to a surface of the holder or canister. In some cases, the sensor is embedded into the holder or canister. In some cases, the visual indication is selected from the group consisting of: a presence or absence of a light, a color change of a light, a flashing of a light, and any combination thereof. In some cases, the visual indication is produced by a light-emitting diode (LED). In some cases, the sensor is operably coupled to the inhaler or nasal device. In some cases, the one or more outputs comprises data. In some cases, the data is collected and stored by the sensor. In some cases, the data is transmitted to or read from a mobile device, a computer, a cloud application or any combination thereof.

In another aspect, a system is provided comprising a sensor for detecting an actuation hold time window of an inhaler or nasal device, wherein the sensor is in contact with the inhaler or nasal device and wherein when the sensor detects the actuation hold time window, the system produces one or more outputs. In some cases, the actuation hold time window comprises a length of time after which the inhaler or nasal device, when held in an actuated state, has delivered an intended dosage range of a drug. In some cases, the actuation hold time window comprises a first time point at the start of the actuation hold time window and a second time point at the end of the actuation hold time window. In some cases, the inhaler or nasal device contains a formulation of a drug. In some cases, the actuation hold time window is determined based on a composition of the formulation of a drug, one or more characteristics of the inhaler or nasal device, or both. In some cases, the formulation comprises one or more excipients. In some cases, the formulation comprises no excipients. In some cases, the one or more outputs comprises an indication. In some cases, the indication is a visual indication, an audible indication or both. In some cases, the visual indication is selected from the group consisting of: a presence or absence of a light, a color change of a light, a flashing of a light, and any combination thereof. In some cases, the visual indication is produced by a light-emitting diode (LED). In some cases, the output is produced when the second time point of the actuation hold time window is detected. In some cases, the sensor further detects one or more parameters of the inhaler or nasal device. In some cases, the one or more parameters comprises one or more shake parameters. In some cases, the one or more shake parameters is selected from the group consisting of: shake duration, shake angle, shake frequency, shake-to-fire interval, and any combination thereof. In some cases, the one or more parameters comprises one or more actuation parameters. In some cases, the one or more actuation parameters is selected from the group consisting of: compression velocity, compression acceleration, actuation hold time, decompression velocity, decompression acceleration, actuation stroke length, and any combination thereof. In some cases, the sensor is operably coupled to the inhaler or nasal device. In some cases, the sensor is affixed to a holder or a canister of the inhaler or nasal device. In some cases, the sensor is permanently affixed to the holder or canister. In some cases, the sensor is removably affixed to the holder or canister. In some cases, the sensor is affixed to a surface of the holder or canister. In some cases, the sensor is embedded into the holder or canister. In some cases, the inhaler or nasal device is a pressurized metered dose inhaler (pMDI) or a dry powder inhaler. In some cases, the one or more outputs comprises data. In some cases, the data is collected and stored by the sensor. In some cases, the data is transmitted to or read from a mobile device, a computer, a cloud application or any combination thereof.

In another aspect, a method is provided for using an inhaler or nasal device comprising a system, wherein the system comprises a sensor in contact with the inhaler or nasal device, the method comprising: a) compressing the inhaler or nasal device for a period of time, wherein the period of time comprises an actuation hold time window; b) decompressing the inhaler or nasal device when the system produces an output, wherein when the sensor detects the end of the actuation hold time window, the system produces the output. In some cases, the compressing releases an amount of a drug. In some cases, the method further comprises, prior to the compressing, shaking the inhaler or nasal device. In some cases, the shaking comprises one or more shake parameters. In some cases, the one or more shake parameters is selected from the group consisting of: shake duration, shake angle, shake frequency, shake-to-fire interval, and any combination thereof. In some cases, the system produces an additional output when a predetermined threshold of the one or more shake parameters has been met. In some cases, the decompressing occurs after an intended dosage range of a drug has been released from the inhaler or nasal device. In some cases, the method further comprises during the actuating, the sensor detects one or more actuation parameters. In some cases, the sensor produces an additional output when a predetermined threshold of the one or more actuation parameters has been met. In some cases, the one or more actuation parameters is selected from the group consisting of: compression velocity, compression acceleration, actuation hold time, decompression velocity, decompression acceleration, actuation stroke length, and any combination thereof. In some cases, the inhaler or nasal device is a pressurized metered dose inhaler (pMDI) or a dry powder inhaler. In some cases, the inhaler or nasal device contains a formulation of a drug. In some cases, the actuation hold time window is determined based on a composition of the formulation of a drug, one or more characteristics of the inhaler or nasal device, or both. In some cases, the formulation comprises one or more excipients. In some cases, the formulation comprises no excipients. In some cases, the sensor is affixed to a holder or a canister of the inhaler or nasal device. In some cases, the sensor is permanently affixed to the holder or canister. In some cases, the sensor is removably affixed to the holder or canister. In some cases, the sensor is affixed to a surface of the holder or canister. In some cases, the sensor is embedded into the holder or canister. In some cases, the output comprises an indication. In some cases, the indication is a visual indication, an audible indication or both. In some cases, the visual indication is selected from the group consisting of: a presence or absence of a light, a color change of a light, a flashing of a light, and any combination thereof. In some cases, the visual indication is produced by a light-emitting diode (LED). In some cases, the sensor is operably coupled to the inhaler or nasal device. In some cases, the output comprises data. In some cases, the data is collected and stored by the sensor. In some cases, the data is transmitted to or read from a mobile device, a computer, a cloud application or any combination thereof.

In another aspect, the disclosure provides for a device or components thereof, as illustrated in any one of FIGS. 1A-C, 2A, 2B, 12A-D, or 15A-E.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A depicts a non-limiting example of a method of attaching a sensor to an adapter as described herein. FIG. 2B depicts a non-limiting example of a sensor and one or more product-specific adapters as described herein.

FIG. 3A depicts an exploded top view of a non-limiting example of a sensor package in accordance with an embodiment of the disclosure. FIG. 3B depicts an exploded bottom view of a non-limiting example of a sensor package in accordance with an embodiment of the disclosure. FIG. 3C depicts a top view of a non-limiting example of a sensor package in accordance with an embodiment of the disclosure. FIG. 3D depicts a bottom view of a non-limiting example of a sensor package in accordance with an embodiment of the disclosure.

FIG. 4A depicts a top view of a non-limiting example of an adapter prior to coupling to an inhaler device in accordance with an embodiment of the disclosure. FIG. 4B depicts a top view of a non-limiting example of an adapter after coupling to an inhaler device in accordance with an embodiment of the disclosure. FIG. 4C depicts a non-limiting example of an expanded view of a pressure tap tube as embodied on an adapter in accordance with an embodiment of the disclosure.

FIG. 5A depicts a non-limiting example of an adapter coupled to an inhaler device prior to coupling of a sensor device in accordance with an embodiment of the disclosure. FIG. 5B depicts a non-limiting example of a sensor device and adapter coupled to an inhaler device in accordance with an embodiment of the disclosure.

FIG. 6A depicts a non-limiting example of a sensor device and an adapter prior to coupling in accordance with an embodiment of the disclosure. FIG. 6B depicts a non-limiting example of a sensor device coupled to an adapter in accordance with an embodiment of the disclosure.

FIG. 7 depicts a non-limiting example of an expanded view of a pressure sensing cavity in accordance with an embodiment of the disclosure.

FIG. 9 depicts non-limiting examples of product-specific operating parameters for specific medicament devices in accordance with an embodiment of the disclosure.

FIG. 12A, FIG. 12B, FIG. 12C, and FIG. 12D depict non-limiting examples of indications outputted by a system of the disclosure.

FIG. 17A depicts a non-limiting example of a top view of a system as described herein. FIG. 17B depicts a non-limiting example of a side view of a system as described herein. FIG. 17C depicts a non-limiting example of a bottom view of a system as described herein. FIG. 17D depicts a non-limiting example of a system assembled onto a pMDI canister as described herein.

DETAILED DESCRIPTION OF THE INVENTION

Figures 1A, 1B, 1C:
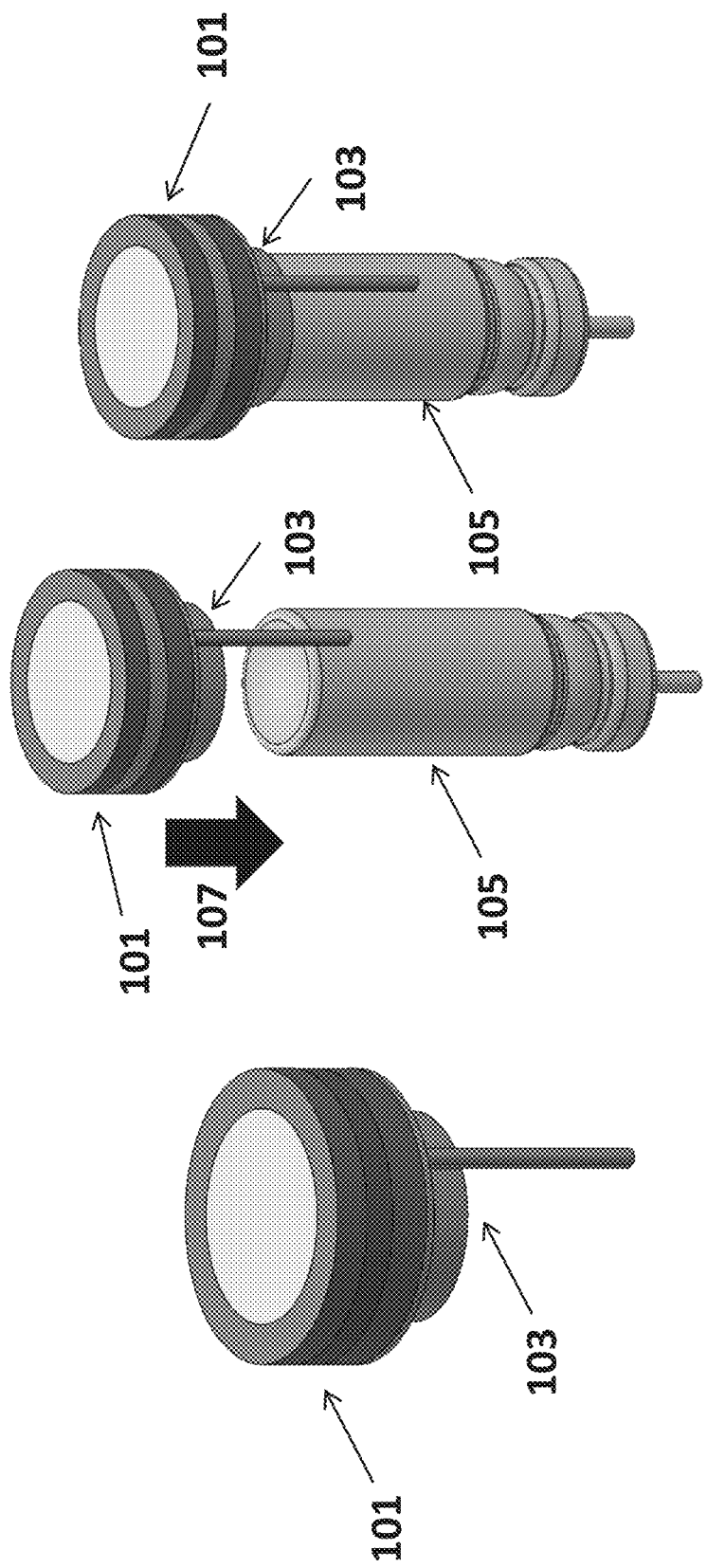
FIG. 1A depicts a non-limiting example of a sensor and an adapter as described herein.
FIG. 1B depicts a non-limiting example of a method of attaching a sensor and adapter to a medicament device as described herein.
FIG. 1C depicts a non-limiting example of a sensor and adapter attached to a medicament device as described herein.

Disclosed herein are methods and devices for sensing or detecting one or more parameters related to usage of a medicament device. In some cases, the medicament device is an inhaler or a nasal device. The methods and devices may be used, for example, to sense or detect when a medicament device is in a condition that is suitable for delivering an intended dosage of a drug. Additionally or alternatively, the methods and devices described herein may guide a user through one or more steps of using a medicament device, for example, by providing feedback to the user based on one or more usage parameters of the medicament device. Generally, the guidance may be provided to the user of a medicament device in order to assist the user in proper usage of the device. Devices and methods described herein may include any number of medicament devices, sensor devices, and/or product-specific adapters.

The term "medicament device" as used herein may refer to any device or apparatus configured to deliver a drug or a therapeutic to a user. Optionally, the medicament device may refer to a container or device containing a medicament. In some non-limiting instances, the term "medicament device" as used herein may refer to an inhaler device or a nasal device. In some cases, the term "medicament device" may refer to an Orally Inhaled and Nasal Drug Product (OINDP) or any component thereof. The term "medicament device" as used herein may refer to the medicament device as a whole, or may refer to any component of the medicament device. By way of example only, the term "medicament device" may refer to an inhaler device, or may refer to a component of the inhaler device, such as a housing of the inhaler device, an actuator of the inhaler device, a mouthpiece of the inhaler device, or a canister of medicament contained within the housing of the inhaler device.

The terms "sensor package" and "sensor device" may be used herein interchangeably and may refer to a device that may be used in conjunction with a medicament device for sensing one or more usage parameters of a medicament device. The sensor device may contain one or more sensors, and additionally may contain any number of electronic components, batteries, microprocessors, switches, buttons, circuit boards, and feedback systems such as auditory or visual outputs. Various non-limiting examples of sensor devices are described herein.

The terms "adapter", "connector", "product-specific adapter" and "product-specific connector" may be used herein interchangeably and may refer to a device that may be used to attach or couple a sensor device to the medicament device. The adapter or connector may be configured to couple a sensor device to a medicament device, and may additionally contain any number of electronic components. In some cases, the adapter may comprise one or more product-specific operating parameters (PSOPs) that are specific for a particular medicament device. Various non-limiting examples of adapters are described herein.

The terms "product-specific operating parameters" or "PSOPs" may be used herein interchangeably and may refer to specific parameters associated with a particular medicament device for proper usage of the device. For example, the PSOPs may refer to the number of times a medicament device should be shaken prior to actuation, or the number of actuations required to prime the medicament device prior to initial usage. Although various PSOPs have been described herein, it should be understood that the PSOPs for a particular medicament device will vary depending on a variety of factors, and thus the various embodiments described herein are to be viewed as non-limiting examples only. PSOPs for a specific medicament device may be provided by the manufacturer of the medicament device (e.g., provided in an instruction sheet for the device or on the box of the device) or may need to be determined empirically. In some instances, the PSOPs are programmed or loaded onto the product-specific adapter as described herein.

Figure 9:
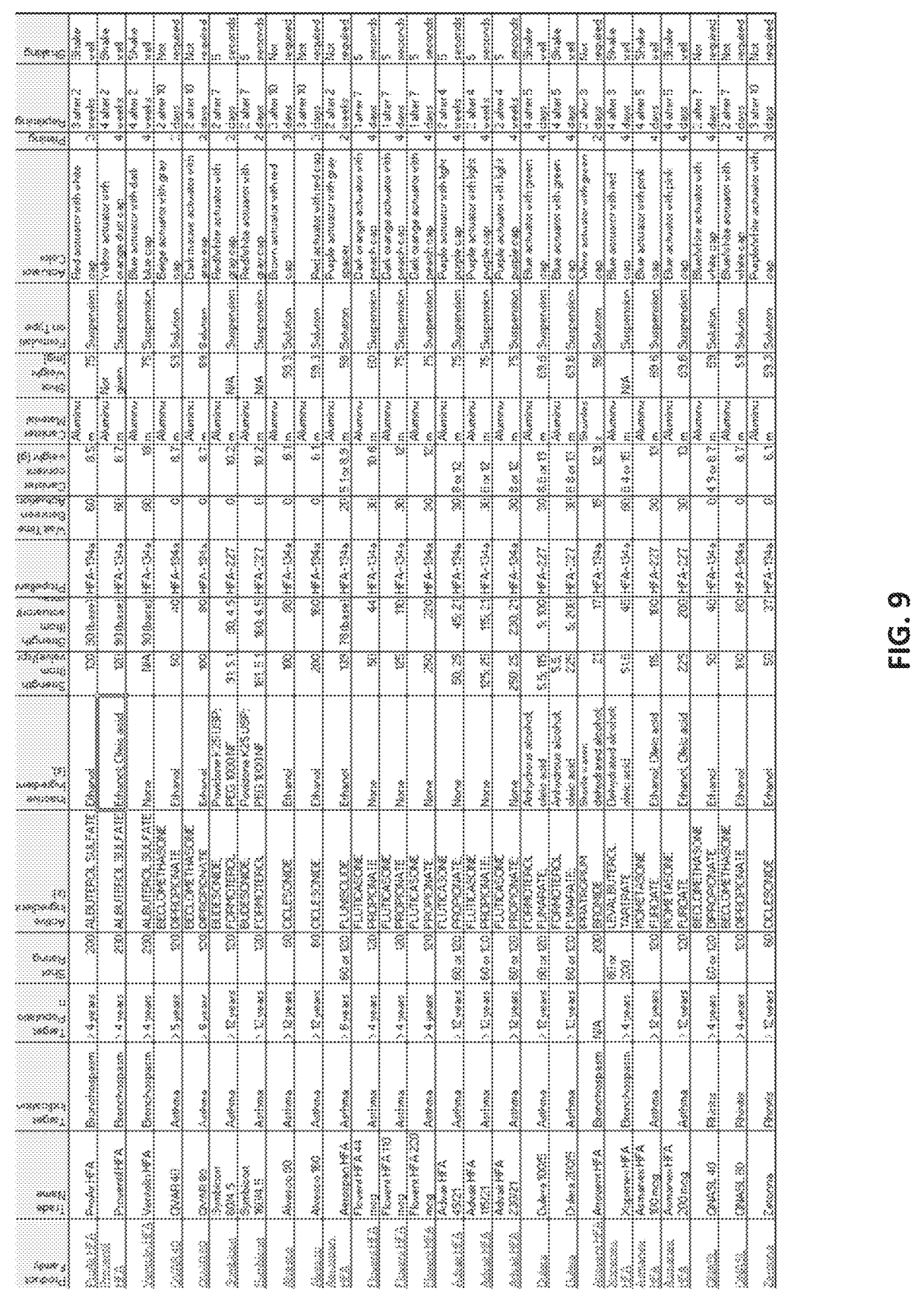

The amount of drug released by a medicament device may be dependent on a number of factors, for example, whether the device has been shaken properly prior to actuation or whether a device user has actuated the device properly. Even further, the composition of the formulation (e.g., drug, excipients, propellants) contained within the device, and characteristics of the device itself may be critical factors in determining how much the device needs to be shaken prior to actuation or how long the device needs to be in an actuated state to deliver an intended dosage range. Usage of medicament devices, and particularly inhaler and nasal devices, are prone to user error, often resulting in an incorrect dosage of drug delivered. This may be especially relevant as different drug formulations, even if used in a same context (e.g., with inhalers), may comprise very different usage parameters, for example, as illustrated in FIG. 9. The devices and methods provided herein may be utilized to indicate to a user of a medicament device that the device is in a condition suitable to deliver the intended dosage range of the formulation. The methods and devices described throughout may guide or instruct a user on how to operate the medicament device properly, thereby improving the use of said device. In some instances, the methods and devices described throughout may guide or instruct a user on how to operate the medicament device correctly, such that the accuracy of an emitted dosage is improved. The methods and devices described herein may allow a user to operate different medicament devices comprising different recommended parameters (e.g., shake parameters, inhalation parameters, etc) appropriately using a single sensor device, as the sensor devices described herein may be tailored to specific types of medicament devices, e.g., via an adapter. In one aspect, a device may comprise one or more sensors for detecting one or more usage parameters of a medicament device.

In one particular aspect, a sensor device is provided for guiding usage of a medicament device, the sensor device comprising: (a) a coupler for coupling to the medicament device, wherein the medicament device is selected from a plurality of different types of medicament devices; (b) one or more sensors for detecting use of the medicament device; (c) a processor configured to: (i) automatically process one or more parameters associated with the medicament device; and (ii) output an signal based on the one or more parameters; and (d) an indicator configured to: (i) operably receive the signal; and (ii) output a guidance to a user of the medicament device, wherein the guidance varies depending on a type of medicament device that is selected.

In another particular aspect, a kit is provided comprising: a sensor device as described herein, and instructions for coupling and/or decoupling the sensor device to an adapter comprising a memory storing the one or more parameters associated with the medicament device.

In another aspect, an adapter is provided for guiding usage of a medicament device, the adapter comprising: (a) a first coupler for coupling to the medicament device; (b) a memory storing one or more parameters associated with the medicament device; and (c) a second coupler for coupling to a sensor device, wherein the sensor device is configured to output a guidance to a user of the medicament device.

In a further aspect, a kit is provided comprising: an adapter as described herein; and instructions for coupling and/or decoupling the adapter to a medicament device selected from a plurality of different types of medicament devices.

In another aspect, a method is provided of a using a sensor device configured to couple to a plurality of different types of medicament devices, the method comprising: (a) coupling the sensor device to a first medicament device; (b) processing one or more parameters associated with the first medicament device; (c) guiding usage of the first medicament device based on the processed one or more parameters associated with the first medicament device; (d) decoupling the sensor device from the first medicament device; (e) coupling the sensor device to a second medicament device, wherein the second medicament device differs in a type of medicament device from the first medicament device; (f) processing one or more parameters associated with the second medicament device; and (g) guiding usage of the second medicament device based on the processed one or more parameters associated with the second medicament device, wherein guiding usage of the second medicament device differs from guiding usage of the first medicament device.

In yet another aspect, a method is provided for measuring usage of an inhaler using one or more sensors, the method comprising: with aid of the one or more sensors: (a) measuring a duration of shaking the inhaler; (b) measuring a duration of a time subsequent to the shaking; (c) measuring an inhalation of a user using inhaler; (d) measuring an actuation of the inhaler; and (e) measuring a duration of a hold down time of the actuation.

In another aspect, a device is provided for monitoring usage of a medicament device, the device comprising: (a) an adapter, wherein the adapter comprises a memory storing a set of parameters specific to a type of the medicament device; and (b) a sensor device separable from, and in operable communication with the adapter, wherein the sensor device is configured to be used with a plurality of different types of adapters each comprising a unique set of parameters specific to different types of medicament devices, wherein the sensor device is configured to produce an output based on the set of parameters.

In another aspect, a method is provided for using an inhaler or nasal device with aid of a sensor, the method comprising: (a) shaking said inhaler or nasal device; (b) measuring a shake-to-fire interval for actuating the inhaler or nasal device using the sensor; and (c) actuating the inhaler or nasal device when said sensor produces an output, wherein when said sensor detects an end of said shake-to-fire interval, said sensor produces said output.

In yet another aspect, a method is provided for using an inhaler or nasal device with aid of a sensor, the method comprising: (a) compressing said inhaler or nasal device for a period of time, wherein said period of time comprises an actuation hold time window; and (b) decompressing said inhaler or nasal device when said sensor produces an output, wherein when said sensor detects an end of said actuation hold time window, said sensor produces said output.

In another aspect, a device is provided for monitoring usage of a medicament device comprising: (a) an adapter comprising: (i) a distal end comprising a first adapter coupler for coupling to the medicament device; (ii) a memory storing one or more parameters associated with the medicament device; (iii) a proximal end comprising a second adapter coupler for coupling to a sensor device, wherein the second adapter coupler comprises a protrusion comprising an electrical interface; and (iv) a pressure tap tube, wherein the pressure tap tube comprises a first end on the proximal end side of the adapter and a second end located distally away from the distal end side of the adapter; and (b) a sensor device removably coupled to the adapter, wherein the sensor device comprises: (i) a mating surface for mating with the proximal end of the adapter, comprising: a receiving port comprising an electrical interface, wherein the receiving port is complementary to the protrusion and is configured to receive the protrusion; and an opening configured to receive the first end of the pressure tap tube; (ii) a pressure sensing cavity operably coupled to the opening, the pressure sensing cavity defining an enclosed chamber with the opening and comprising a barometer; (iii) a processor operably coupled to the receiving port, the processor configured to: receive the one or more parameters associated with the medicament device from the adapter; automatically process the one or more parameters associated with the medicament device; and output a signal based on the one or more parameters; and (iv) an indicator configured to: operably receive the signal; and output a guidance to a user of the medicament device, wherein the guidance varies depending on the one or more parameters that is received.

In some cases, the methods and devices described herein may be used with essentially any medicament device. In particular cases, the methods and devices described herein may be used with an inhaler device. An inhaler device may be utilized for e.g., delivery of a drug or substance directly to the lungs of a subject. The methods and devices described herein may be suitable for use with any inhaler device that requires shaking and/or actuation. In some cases, the inhaler device is a metered-dose inhaler (MDI), for example, a pressurized metered-dose inhaler (pMDI). Non-limiting examples of MDIs may include AeroChamber® and Autohaler®. In some cases, the MDI comprises a spacer or aerosol holding chamber. The inhaler device may be a dry powder inhaler, non-limiting examples including: Aerolizer®, Diskus®, Ellipta™, Flexhaler®, Handihaler®, Neohaler®, Pressair™, Twisthaler®, Rotahaler® and Turbuhaler®.

In other particular instances, the methods and devices may be used with a nasal device for, e.g., local delivery of a drug to the nose or the paranasal sinuses. Non-limiting examples of nasal devices may include: mechanical spray pumps (e.g., squeeze bottles, multi-dose metered-dose spray pumps, single/duo-dose spray pumps, bi-directional multi-dose spray pumps), gas-driven spray systems/atomizers, mechanical powder sprayers, breath actuated inhalers, and insufflators. In other particular instances, the methods and devices may be used with a nebulizer and/or other devices.

The inhaler or nasal device may be an Orally Inhaled and Nasal Drug Product (OINDP). Non-limiting examples of OINDPs which may be suitable for use with the devices described herein may include: aclidinium bromide inhalation powder (Tudorza® Pressair®), ipratropium inhalation aerosol (Atrovent® HFA), tiotropium inhalation powder Spiriva® Handihaler®), tiotropium inhalation solution (Spiriva® Respimat®), umeclidinium inhalation powder (Incruse® Ellipta®), albuterol/ipratropium inhalation solution (DuoNeb®), albuterol/ipratropium bromide inhalation spray (Combivent® Respimat®), budesonide/formoterol fumarate dihydrate inhalation aerosol (Symbicort®), fluticasone/salmeterol inhalation powder (Advair® Diskus®), fluticasone/salmeterol inhalation aerosol (Advair® HFA), fluticasone furoate/vilanterol inhalation powder (Breo® Ellipta®), mometasone furoate/formoterol fumarate inhalation aerosol (Dulera®), tiotropium bromide/olodaterol inhalation spray (Stiolto™ Respimat®), umeclidinium/vilanterol inhalation powder (Anoro® Ellipta®), beclomethasone dipropionate HFA inhalation aerosol (Qvar®), beclomethasone dipropionate nasal aerosol (QNASL®), budesonide inhalation powder (Pulmicort® Flexhaler®), budesonide inhalation suspension (Pulmicort® Respules®), ciclesonide inhalation aerosol (Alvesco®), flunisolide inhalation aerosol (Aerospan®), fluticasone furoate inhalation powder (Arnuity™ Ellipta®), fluticasone propionate inhalation aerosol (Flovent® HFA), fluticasone propionate inhalation powder (Flovent® Diskus®), mometasone furoate inhalation powder (Asmanex® Twisthaler®), mometasone furoate inhalation aerosol (Asmanex® HFA), arformoterol tartrate inhalation solution (Brovana®), formoterol fumarate inhalation powder (Foradil®), formoterol fumarate inhalation solution (Perforomist®), indacaterol inhalation powder (Arcapta™ Neohaler™), olodaterol inhalation spray (Striverdi® Respimat®), salmeterol xinafoate inhalation powder (Serevent® Diskus®), albuterol sulfate inhalation powder (Proair® Respiclick®), albuterol sulfate inhalation aerosol (Proair® HFA), albuterol inhalation solution (AccuNeb®), albuterol sulfate inhalation aerosol (Proventil® HFA), albuterol sulfate inhalation aerosol (Ventolin® HFA), levalbuterol tartrate inhalation aerosol (Xopenex® THFA), and ciclesonide nasal aerosol (Zetonna®).

The medicament device may include a formulation of, for example, a drug or an active ingredient. In some cases, the formulation includes one or more excipients. In some cases, the formulation does not include any excipients. In some cases, the formulation includes one or more propellants. The formulation may be a suspension, a solution, or a dry powder.

The methods and devices described herein may involve one or more sensors. The one or more sensors may be in contact with the medicament device. In some cases, the one or more sensors are in direct contact with the medicament device, for example, one or more sensor components is directly contacting or touching a component of the medicament device. The one or more sensors may be in contact with any part of the medicament device, such as, for example, the housing of the medicament device or the canister of the medicament device. In some cases, the one or more sensors are in contact with the housing of the medicament device. The housing of the medicament device may be the plastic component of the medicament device such as the actuator, the mouthpiece, or both. In some cases, the one or more sensors are in contact with the canister of the medicament device. The canister may be the metal component of the medicament device (e.g., stainless steel or aluminum) which contains the formulation. In such cases where the medicament device is a metered dose inhaler, the one or more sensors may be in contact with the metering valve.

In some cases, the one or more sensors may be affixed to the holder or the canister of the medicament device. In such cases where the medicament device is an inhaler device, the one or more sensors may be affixed to the actuator and/or mouthpiece of the inhaler device. In such cases where the medicament device is a nasal device, the one or more sensors may be affixed to the nasal device's bottle, pump, or actuator nozzle tip. In some cases, the one or more sensors are permanently affixed or attached to the holder or the canister of the medicament device. For example, the one or more sensors may not be detachable or decoupled from the medicament device. The one or more sensors may be glued, welded, embedded, adhered, or otherwise affixed to the medicament device in such a way that the one or more sensors cannot be removed. In other cases, the one or more sensors may be removably affixed to the holder or canister of the medicament device. In this example, the one or more sensors may be capable of being removed from the holder or the canister of the medicament device. In some instances, the one or more sensors may be removed from one medicament device and affixed to a separate medicament device. In some instances, the one or more sensors may be attached to an adapter that provides for removably affixing the sensor to a medicament device. In some cases, the medicament device may be provided and/or obtained with the one or more sensors already attached. In other cases, the medicament device may be provided and/or obtained without the one or more sensors already attached. In particular cases, the one or more sensors may be sold and/or purchased separately from the medicament device. In such cases, the one or more sensors may be attached to the medicament device by, for example, the user (e.g., a patient), a healthcare provider, or a manufacturer.

In some instances, the one or more sensors are contained within a sensor device or sensor package configured to be attached to a medicament device. The sensor device may comprise a housing for containing the one or more sensors. The sensor device may further comprise, contained within the housing, the one or more sensors. The one or more sensors may include any type of sensor that may be useful for monitoring usage of a medicament device. Non-limiting examples of sensors that may be provided in the sensor device include: airflow sensors (e.g., a thermistor, a pressure sensor, a barometer), integrated flow sensors, position or displacement sensors, rate sensors, tilt sensors, touch sensors (e.g., an electrode, a capacitive or resistive touch sensor), shake sensors (e.g., accelerometer), magnetometers, temperature sensors, global positioning system (GPS) chips, ambient light sensors, sensors capable of detecting more than one parameter, and any combination thereof.

In some cases, the sensor device may be used with essentially any medicament device. In particular instances, the sensor device may be universally configured such that said sensor device is operable with any number and variety of medicament devices. In a particular aspect, the sensor device may be coupled to and used with a first medicament device, then subsequently decoupled from the medicament device and then attached to and used with a second, different medicament device. The first and second medicament devices may be of the same type, or different types. A type of medicament device as referred to herein, may depend on specifications of the medicament device. For example, a type may depend on active ingredients, inactive ingredients, strength, recommended shake duration, and such as shown in the columns of FIG. 9. In some instances, the sensor device may be reused a plurality of times, for example, 2, 3, 4, 5, 6, 7, 8, 9, 10, 15, 20, 30, 40, 50, 100, 200, 500, 1000, 2000, 5000, or more times.

In some cases, the sensor device may be coupled directly to a medicament device (e.g., by a coupler that allows for attachment to the medicament device) or by attachment to an adapter. For example, the sensor device may comprise a communication unit (e.g., wireless communication unit, RFID chip, optical reader, etc). A medicament device (e.g., canister used with an inhaler) may comprise another communication unit (e.g., wireless communication unit, RFIC chip, barcode that may be read, etc) which can communicate with the communication unit of the sensor device. In such a case, the medicament device may be configured to communicate relevant parameters (e.g., shake parameters, etc) that can be processed by the sensor device to guide a user to appropriately use the medicament device.

In some instances, the sensor device may be coupled to a medicament device via one or more intermediary devices. For example, the sensor device may be coupled to the medicament device via an adapter. The adapter may be configured to couple directly to a medicament device or a component thereof. In one such example, the adapter may be specific for a particular medicament device such that the universal sensor device may be coupled to virtually any medicament device by use of the product-specific adapter. The sensor device may include a coupler for coupling to the medicament device and/or the adapter. The coupler may include a receiving port for receiving a complementary protrusion of the adapter. In such cases, the coupler may also include an electrical interface for electrically coupling to the adapter. In some cases, the coupler may include one or more latch points for receiving one or more latches of an adapter comprising an adhesive configured to couple to the medicament device.

FIGS. 1A-C depict a non-limiting example of how a sensor device coupled to an adapter is attached to a medicament device in accordance with the disclosure. FIG. 1A depicts a sensor device 101 coupled to an adapter 103. In some cases, the sensor device 101 may be attached to the medicament device 105 by attaching 107 the adapter 103 (with the sensor device 101 attached) to the holder or canister of the inhaler device 105, as shown in FIGS. 1B & 1C.

In some instances, the adapter may be designed to fit onto the holder or canister of a specific medicament device product. In some instances, the sensor device 201 may be affixed 205 e.g., snapped or sealed, onto the adapter 203 as depicted in FIG. 2A. The sensor device (i.e., the sensor device and the adapter) may then be affixed to the inhaler device as described above. In some cases, the sensor device and product-specific adapter may be provided separately or as a unit or kit containing one or more sensor devices and one or more adapters. For example, as shown in FIG. 2B, a sensor device 201 may be provided with one or more product-specific adapters 201a, 201b, 201c that may be attached to the sensor device as described previously.

In some cases, the sensor device may be reusable, for example, the sensor device may be configured to be used 2, 3, 4, 5, 6, 7, 8, 9, 10, 15, 20, 30, 40, 50, 100, 200, 500, 1000, 2000, 4000, or more times. Optionally, the sensor device may be configured to be used indefinitely. The sensor device may be configured to be used for a duration of at least 1 month, 2 months, 4 months, 6 months, 8 months, 10 months, 12 months, or more. The sensor device may be rechargeable, for example, the sensor device may comprise a battery that can be recharged one or more times. In some cases, the battery may be recharged at least 1, 2, 3, 4, 5, 6, 7, 8, 9, 10, 15, 20, 30, 40, 50, or more times. In some instances, the battery may be removed from the sensor device and recharged. In some cases, the battery may be replaced at least 1, 2, 3, 4, 5, 6, 7, 8, 9, 10, 15, 20, 30, 40, 50, or more times.

In some cases, the adapter may be disposable. In some instances, the adapter may be configured to be used with a single medicament device product. In some instances, the adapter may be used through the life of the medicament device, after which the adapter may be discarded. The reusability of the sensor device may beneficially allow a user to use a single sensor device with a plurality of different adapters depending on the user's needs. In some instances, a single user having different product needs may use a single sensor device with a plurality of different adapters. For example, a sensor device may be used in conjunction with a first adapter capable of being used with a first medicament device for the life of the first medicament device. After the first medicament device has been exhausted, the user may remove the adapter and sensor device from the first medicament device, discard the first adapter, and then use the same sensor device with a second adapter capable of being used with a second medicament device for the life of the second medicament device. In some cases, the first and second medicament devices are the same type (e.g., the same medicament product), and may utilize the same type of adapter (i.e., an adapter that is capable of being used with either the first or the second medicament device). In other cases, the first and second medicament devices are different, and may utilize different types of adapters (i.e., the first adapter is capable of being used with the first medicament device, but not the second medicament device; and the second adapter is capable of being used with the second medicament device, but not the first medicament device). In both scenarios, the sensor device may be configured to work in conjunction with both adapters, such that the sensor device can be re-used with different adapters.

The sensor device may further include additional working components. For example, the sensor device may include a processor configured to automatically process one or more parameters associated with the medicament device; and output a signal based on the one or more parameters. In some cases, the sensor device may include a microcontroller which may be used to manage and control the system functions including, but not limited to, firmware logic and data processing algorithms, timers for providing a precision time base for sensor data acquisition functions, and audio feedback sequences. The sensor device may include an audio player, amplifier, and/or loudspeaker for providing auditory feedback to a user of the medicament device. The sensor device may include a battery, such as a rechargeable lithium-based battery. Such battery may be capable of powering the sensor device for up to 60 days before a recharge. The sensor device may include an LED for indicating battery charging status and PC application connectivity. The sensor device may include a fixed amount of non-volatile memory for storing usage history data and other system settings. The sensor device may include a real-time clock for providing accurate date and time-stamping of the entries in the usage history. The real-time clock may be capable of providing accurate timekeeping even when connected to a fully discharged battery. The sensor device may include a button switch to turn the system on or off. The button switch may be located anywhere on the sensor device, and in some cases, is located on a distal end of the sensor device. The button switch may be touched, pushed, or otherwise contacted by a user of the medicament device. The button switch may perform additional features such as, for example, enabling a user to acknowledge feedback received from the sensor device or for directing system operation. The sensor device may also include a USB connector interface that can be used to recharge the battery or communicate with the PC application software and/or wireless interface compatibility such as Bluetooth® capabilities. In such cases where the sensor device is used in conjunction with an adapter, the sensor device may include an electro-mechanical interface for connecting to the adapter.

Figure 3A:
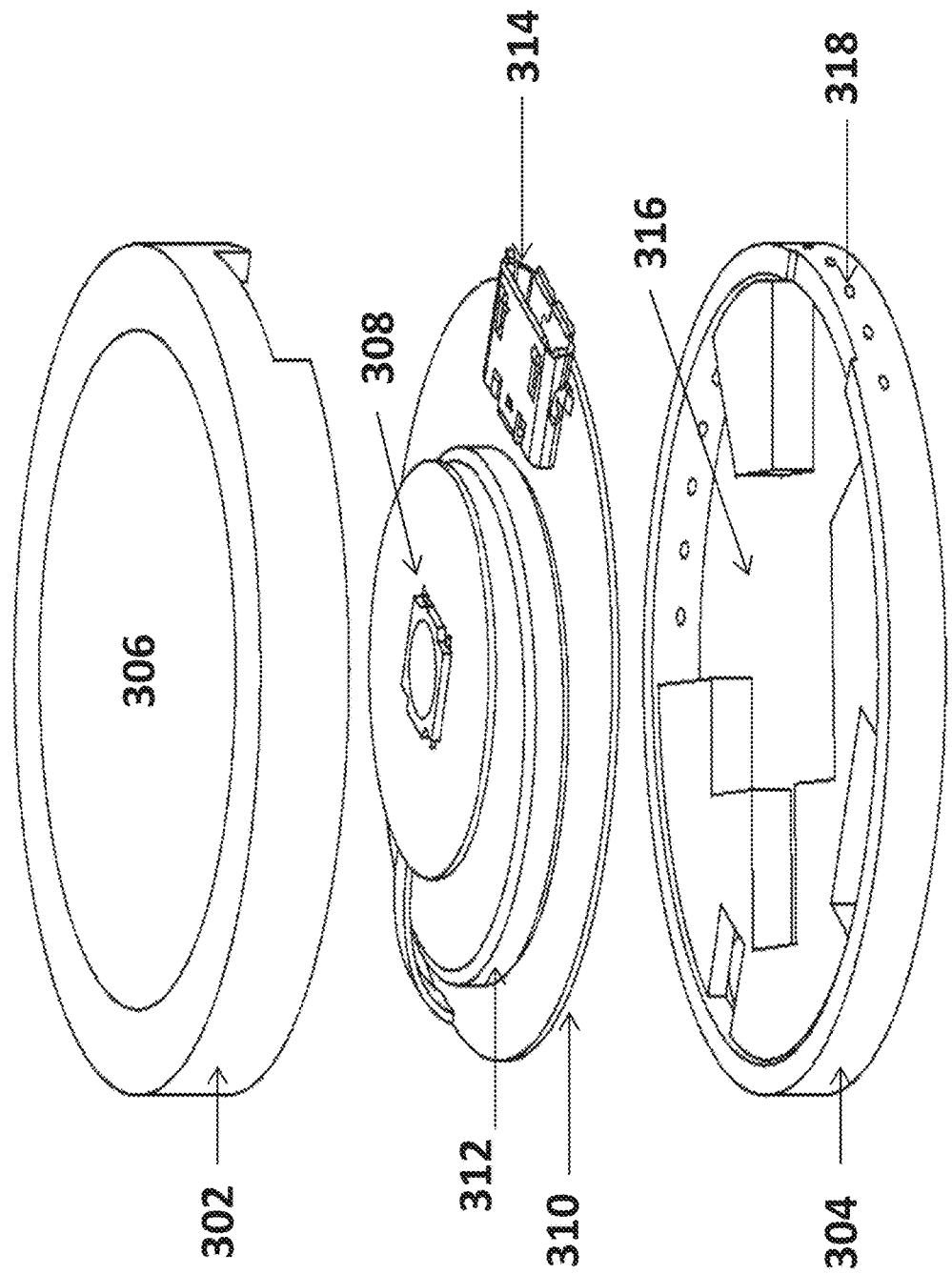
FIG. 3A, FIG. 3B, FIG. 3C, and FIG. 3D depict multiple views of a sensor package as described in accordance with various embodiments of the disclosure.

FIG. 3A illustrates an exploded view of a sensor device from the top, in accordance with embodiments. FIG. 3C illustrates a perspective view of a sensor device 300 from the top, in accordance with embodiments. The sensor device may comprise an upper body 302 and a lower body 304. Each of the upper body 302 and the lower body 304 may or may not be circular. Each of the upper body 302 and the lower body 304 may or may not be substantially flat. In some instances, the upper 302 or lower body 304 may comprise interactive components. For example, a surface 306 of the upper body 302 may comprise a movable component. The movable component may be actuatable by a user. The movable component may be used to control a functionality of the sensor device 300, e.g., to turn the sensor device on or off, or change an operating mode of the sensor device 300. As another example, a surface 306 of the upper body 302 may comprise a visual display. The visual display may be used to give an indication, or guidance to a user, as described herein. As another example, a surface 306 of the upper body 302 may comprise a touch sensitive button. The touch sensitive button may be used to control a functionality of the sensor device 300, e.g., to turn the sensor device on or off, or change an operating mode of the sensor device 300. Optionally, the touch sensitive button may be configured to function also as a visual display as described above. While the interactive component of the sensor device 300 is illustrated on a top surface of the upper body as an example, it is to be understood that it may be located anywhere, e.g., on a side, on the lower body, etc. The lower body 304 may comprise a sound chamber 316. The sound chamber may aid in transmission of auditory indications generated from the sensor device 300. In some instances, the lower body 304 may comprise sound ports 318 which may allow auditory instructions to be communicated to a user using the sensor device 300.

The upper body 302 and the lower body 304 may comprise a housing, or exterior of the sensor device 300. The housing may comprise a volume equal to or less than 4 cm$^3$, 6 cm$^3$, 8 cm$^3$, 10 cm$^3$, 12 cm$^3$, 14 cm$^3$, 16 cm$^3$, 18 cm$^3$, 20 cm$^3$, 25 cm$^3$, 30 cm$^3$, 35 cm$^3$, 40 cm$^3$, 50 cm$^3$, or any value there in-between. The small size of the housing may ensure that the sensor device 300 remains unobtrusive to a user of the sensor device 300. The upper body 302 and the lower body 304 may be configured to be permanently coupled to one another. Alternatively, the upper 302 and lower body 304 may be configured to be removably coupled to one another such that a user may remove the upper body 302 from the lower body 304 or vice versa.

In some instances, the upper body 302 and the lower body 304 may surround or enclose electronic components 310. The upper body 302 and the lower body 304 may partially, or wholly, surround or enclose the electronic components 310. The electronic components 310 of the sensor device 300 may comprise one or more circuit boards 311, batteries 312, interfaces 314, or other elements 308. The electronic components 310 of the sensor device 300 may comprise a speaker, one or more processors, one or more additional sensors, etc as further described elsewhere. The circuit boards 310 may be rigid and/or flexible. The circuit boards 310 may comprise two rigid components coupled together by a flexible component. In some instances, the two rigid components may sandwich there between one or more batteries 312. Advantageously, this configuration may allow a barometer 320 to be operably coupled to a pressure tap tube 410 as further described elsewhere while allowing an interactive component of the sensor device 300 (e.g., a switch 306) to be located on a top portion of the device 300. The circuit board 310 may enable various other electronic components to couple to one another and/or communicate with one another. The batteries 312 may provide a power source for the sensor device 300. The batteries 312 may allow the sensor device 300 to run for a period of time equal to or more than about 1 hour, 2 hours, 5 hours, 10 hours, 16 hours, 24 hours, 2 days, 5 days, a week, 2 weeks, 4 weeks, a month, 2 months, 4 months, 6 months, 8 months, 1 year, 2 years, or more years. Optionally, the batteries 312 may be rechargeable. The interfaces 314 may allow the sensor device 300 to communicate with one or more external devices. In some instances, the interface may be a USB port 314. In some instances, the sensor device is configured for wireless interface compatibility (e.g., Bluetooth®). Optionally, the interfaces 314 may allow the recharging of the batteries 312 of the sensor device 300. The other elements 308 may comprise various additional elements. In some instances, the other elements 308 may comprise a button, or a switch. The switch may be used to control a functionality of the sensor device 300, e.g., to turn the sensor device 300 on or off, or change an operating mode of the sensor device 300. For example, a user actuating a surface 306 of the sensor device 300 may press on the button 308, affecting the sensor device 300 (e.g., turning it on or off).

The other elements in some instances may comprise sensors, such as an accelerometer, a barometer 320, a temperature sensor, a magnetometer, an ambient light sensor, or a global positioning system (GPS). The accelerometer may allow the sensing device to measure various parameters described throughout such as the shake parameters, and/or orientation of the medicament device. In some instances, the accelerometer may be located on the sensor device 300 such that when the sensor device is coupled to the medicament device, it is located along a central axis of the medicament device, as depicted, for example, in FIG. 11. The barometer 320 may allow the sensor device to measure various parameters described throughout such as the inhalation parameters. The temperature sensor may allow the sensor device to measure various parameters described throughout such as a temperature of the environment around the sensor device and/or the medicament device. This may advantageously allow the sensor device to adjust guidance for using the medicament device, or inhaler, e.g., by varying the guidance depending on environmental factors. As one example, if it is determined that the medicament device is being used in a very cold environment, the sensor device may adjust its guidance to (e.g., shake parameters) or even recommend the user from refraining from using the medicament device until a predetermined temperature is reached. The predetermined temperature may be equal to or less than about 0° C., 2° C., 4° C., 6° C., 8° C., 10° C., 12° C., 14° C., 16° C., 18° C., 20° C., 22° C., 24° C., 26° C., 28° C., 30° C., 32° C., 34° C., 36° C., 38° C., or 40° C. The magnetometer may allow the sensor device to measure various parameters described throughout such as a true direction of the sensor device and/or the medicament device. This may advantageously allow the sensor device to adjust guidance for using the medicament device, or inhaler, e.g., by varying the guidance depending on environmental factors. As one example, if it is determined that a person would have been facing in the direction of sunlight, the sensor device may adjust its guidance from a visual (e.g., light) based guidance to an auditory based guidance. The ambient light sensor may allow the sensor device to measure the ambient light level of the environment where the sensor device is being used and adjust its indication settings automatically (e.g., increase/decrease the visual indicator brightness level). The GPS may allow the sensor device to measure various parameters described throughout, such as a global coordinate of where the sensor device is being used, etc. This may advantageously allow the sensor device to adjust guidance for using the medicament device, or inhaler, e.g., by varying the guidance depending on environmental factors such as an elevation, humidity, etc of where the device is being used in.

Figure 3B:
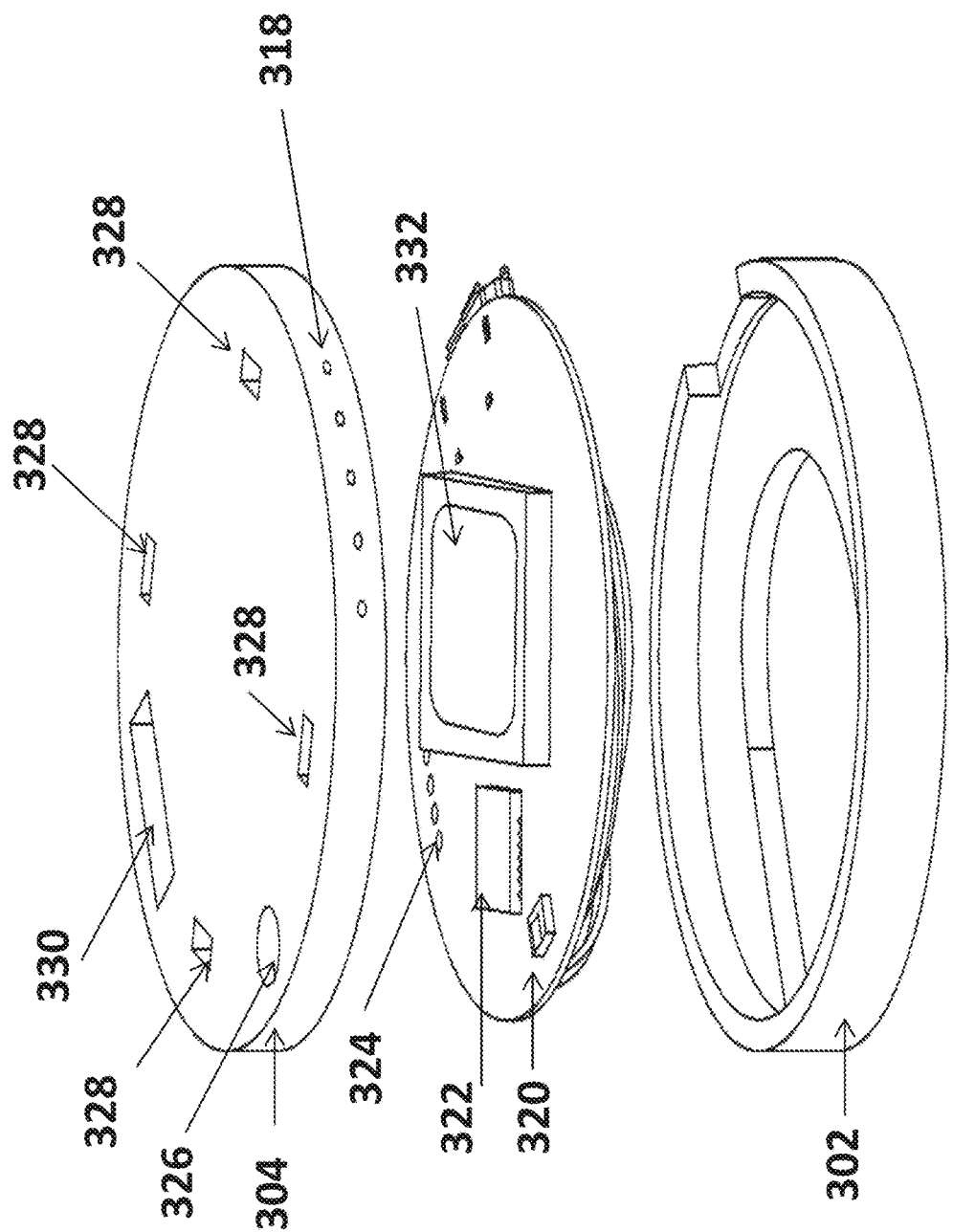
Figure 3C:
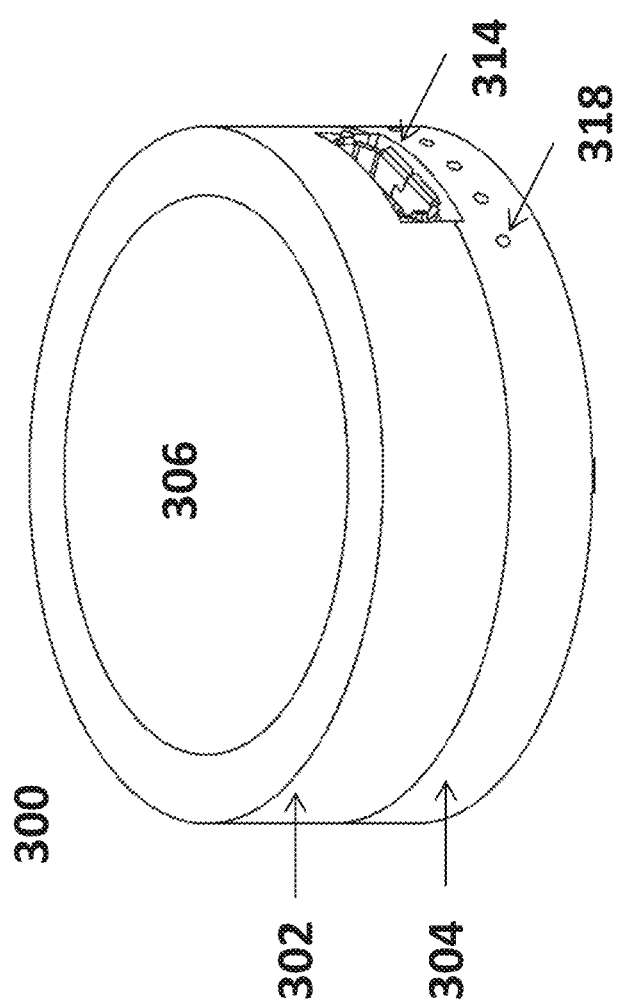
Figure 3D:
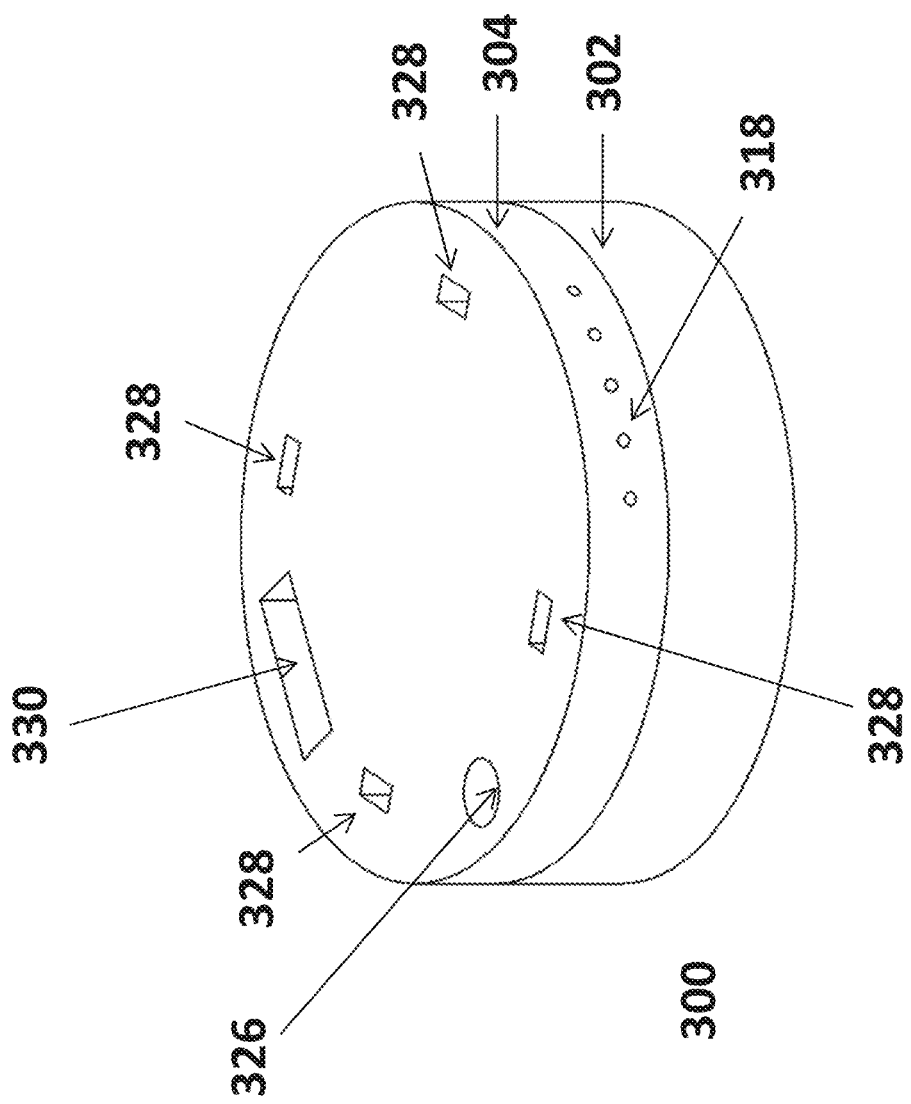

FIG. 3B illustrates a blown up view of a sensor device 300 from the bottom, in accordance with embodiments. FIG. 3D illustrates a perspective view of a sensor device 300 from the bottom, in accordance with embodiments. The sensor device 300 may be the sensor device 300 as described throughout, e.g., as shown in FIG. 3A. A lower body 304 of the sensor device 300 may comprise one or more couplers 328, 330. Optionally, the lower body 304 of the sensor device 300 together with the electronic components may comprise one or more couplers. The one or more couplers may be configured to couple to a medicament device, e.g. directly or indirectly via other intermediary devices. While couplers in the form of a receiving port 328, 330 are illustrated in FIG. 3B, it is to be understood that any form of coupling (e.g., adhesives, protrusions, form fitting mechanism, hooks, etc.) may be an example of a coupler. The one or more couplers may comprise a receiving port 328, 330. In some instances, the one or more couplers, or the one or more receiving ports 328, 330 may comprise, or lead to an electrical interface 324. The electrical interface 324 may be electrical contacts. In some instances, the electrical interface 324 may allow the sensor device 300 to communicate (e.g., electrically) with other devices, such as an adapter 400 described herein. Optionally, the receiving port 328, 330 may be configured (e.g., shaped) to removably receive a complementary protrusion of an adapter 408 described herein. Optionally, the receiving port 328, 330 may be configured to allow communication with an adapter 400 described herein, which may comprise a memory storing one or more parameters associated with a medicament device. In some instances, the one or more couplers may comprise one or more latch points 328. The latch points 328 may allow for secure form fitting of the sensor device 300 with one or more other devices, such as the medicament device and/or adapters 400 described herein. The one or more latch points 328 may be configured for receiving one or more latches 402 of other devices, such as the medicament device and/or adapters 400. Advantageously, the one or more latch points 328 which comprise a greater integrity (e.g., in structure) may allow the sensor device 300 to be used over long periods of time without failing, while other more disposable components such as the adapter 400 are used for shorter periods of time (e.g., with the protrusions).

Figure 8:
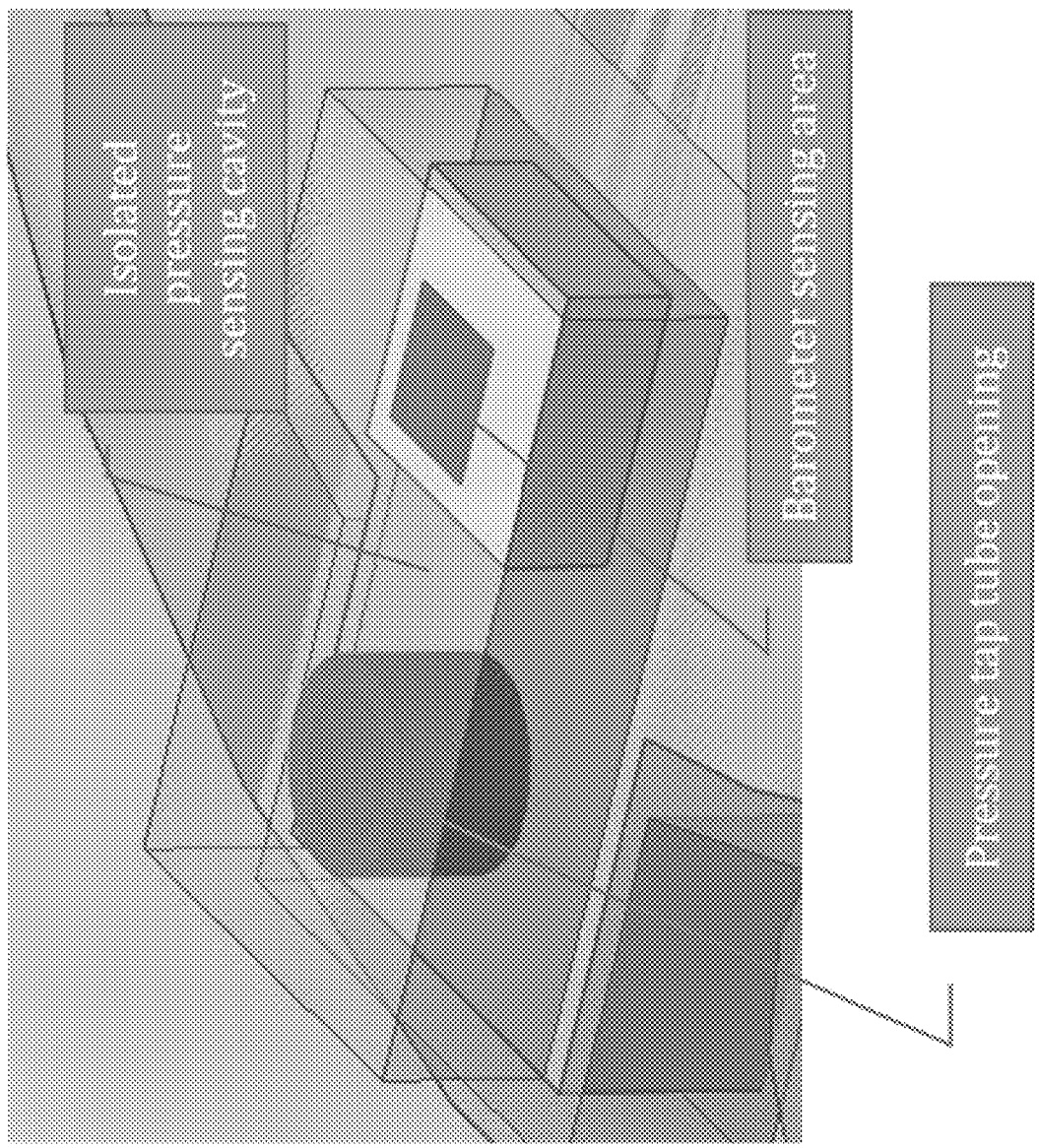
FIG. 8 depicts a non-limiting example of a pressure sensing cavity with a barometer located on a bottom surface of a circuit board in accordance with an embodiment of the disclosure.

The lower body 304 of the sensor device 300 may comprise an opening 326. The opening 326 may also be referred to herein as an interface to a pressure tap. The opening 326 may be configured to receive a pressure tap tube 410 of the adapter 400. The opening 326 may lead to a sensor, such as a barometer 320, and/or a pressure sensing cavity (see, e.g., FIG. 7). Optionally, the opening 326 may be a single opening (e.g., the only opening) to the pressure sensing cavity. Accordingly, the pressure sensing cavity may be isolated (e.g., except for the opening). FIG. 7 illustrates a pressure sensing cavity 320 coupled to a pressure tap tube 410 of an adapter 400, in accordance with embodiments. As described throughout, the pressure tap tube 410 may comprise a proximal portion 702 located on a first surface (e.g., top surface) of the adapter 400. The proximal portion 702 may comprise a sealing element 704. The sealing element in some instances may be an "O" ring. The pressure sensing cavity may comprise one or more sensors, such as the barometer 320. The pressure sensing cavity may be minimally sized so as to allow the barometer 320 to sense a pressure change due to a user's inhalation as soon as possible. In some instances, the pressure sensing cavity may comprise a size equal to or less than about 2 cm³, 4 cm³, 6 mm³, 8 mm³, 10 mm³, 12 mm³, 14 mm³, 16 mm³, 20 mm³, 22 mm³, 24 mm³, 26 mm³, 28 mm³, 30 cm³, or any value there between. The pressure sensing cavity in some instances may allow a bidirectional flow of air in and out of the pressure sensing cavity, e.g., through the opening. Each of the pressure sensing cavity and/or the barometer 320 may be located, or positioned on a circuit board 310 described above. While the barometer 320 is illustrated located hanging from a ceiling or an underside of the circuit board, it is to be understood that the configuration is illustrative and not limiting. FIG. 8 illustrates a pressure sensing cavity with a barometer located on a bottom surface of a circuit board, in accordance with embodiments. As shown, the barometer, or a sensing area of the barometer may be exposed on a silicon substrate itself.

Referring back to FIG. 3, the electronic components 310 may comprise an indicator. The indicator may comprise a speaker, a light source (e.g., a light emitting diode), or a visual display as referred to above. The indicator may be configured to operably receive a signal generated, processed, or output from a processor. In some instances, the indicator may be configured to output a guidance to a user of the medicament device described herein, e.g., via visual or auditory indications. In such cases where an auditory indicator is used, the auditory indicator may be adjustable or customizable by the user. For example, the volume may be adjusted or the style of voice or sound may be changed or customized. Similarly, when a visual indicator is used, the color of light, the pattern of light indications, and/or the brightness of the light may be adjusted. In some cases, the user may have the ability to change the device from an auditory indication to a visual indication and vice versa. In some instances, the guidance may vary depending on a type of medicament device that is selected, or being used. The type of medicament device that is being used may depend on the target indication for the device, shot rating, active ingredients, inactive ingredients, strength, propellants, recommended time between actuations, canister content weight, shot weight, formulation type, recommended number of priming steps, recommended duration between timing, recommended number of re-priming steps, or recommended shake duration, e.g., as shown in FIG. 9. In some instances, the guidance may be tailored such that the sensor gives a guidance according to the recommended parameters. In some instances, depending on the type of the medicament device, the guidance may vary in a duration of shaking a medicament device, a shake-to-fire interval, a wait time between actuations, a number of priming steps, a number of re-priming steps, or a duration until re-priming steps. In some instances, the duration of shaking the medicament device may vary between 0 and 30 seconds. In some instances, the wait time between actuations varies between 0 to 60 seconds. In some instances, the number of priming steps varies between 0 and 5. In some instances, the number of re-priming steps varies between 0 and 5. In some instances, the duration until re-priming steps varies between 0 and 30 days. In some instances, the shake-to-fire interval varies from 0 to 30 seconds.

The sensor device 300 may comprise one or more processors, or a microcontroller 322. The processor may be configured to automatically process one or more parameters associated with the medicament device. The one or more parameters may be recommended parameters for the medicament device (e.g., recommended shake parameters) for example, as shown in FIG. 9. In some instances, the processor may be configured to receive the one or more parameters from another device such as the adapter 400 referred to herein. For example, once the sensor device is connected to the adapter (as depicted in FIGS. 5A-B and FIGS. 6A-B) (e.g., and turned on and/or authenticated), the sensor device 300 may be configured to automatically receive the one or more parameters associated with the medicament device from the adapter 400. Accordingly, the sensor device may be configured to be utilized with a plurality of different medicament devices and output an appropriate guidance according to the type of the medicament device. The processor, may be configured to output a signal based on the processed one or more processors. In some instances, the sensor device may be configured to give different guidance depending on the type of medicament device. In some instances, the sensor device may be configured to give a guidance differing in 1, 2, 3, 4, 5, 6, 7, 8, 9, 10, or more parameters (e.g., shake parameter) depending on the type of medicament device (or adapter) it is coupled to. As described throughout, the medicament device may individually or collectively also refer to a canister or an inhaler. The inhaler may be a pressurized dose metered inhaler. Optionally, a kit may be provided. The kit may comprise the sensor device described throughout, and instructions for coupling and/or decoupling the sensor device to an adapter. Alternatively, the kit may comprise the sensor device described throughout, the adapter device described throughout, and instructions for coupling and/or decoupling the sensor device to an adapter.

In some embodiments, the adapter comprises electronics and/or working components. In some cases, the adapter is programmed with product-specific operating parameters (PSOPs), for example, the operating parameters for using a specific medicament device correctly. For example, the adapter may be programmed with specific shake parameters, actuation parameters, and the like, that are specific for a medicament device. PSOPs may be provided by the manufacturer of a medicament device (e.g., on an instruction sheet) or may be determined empirically. FIG. 9 depicts non-limiting examples of PSOPs for specific medicament devices that may be programmed into an adapter for use with such devices. When used in conjunction with the sensor device, the adapter may receive data from the sensor device, including, but not limited to, actuation date and/or time, shot number (corresponding to the number of times the device has been actuated), and sensor ID. The adapter, programmed with the PSOPs, may determine when one or more predetermined thresholds of shake parameters, actuation parameters, etc., has/have been reached. The adapter may then relay a signal to the sensor device, and a light or auditory or other indicator may be activated in the sensor device as further described herein. The adapter may include a cryptographic authenticating device for uniquely identifying the adapter and for preventing cloning or counterfeiting of the adapter. The adapter may further include a secure memory block for storing the PSOPs for reading exclusively by the adapter after successful authentication by the authenticating device.

Figure 4A:
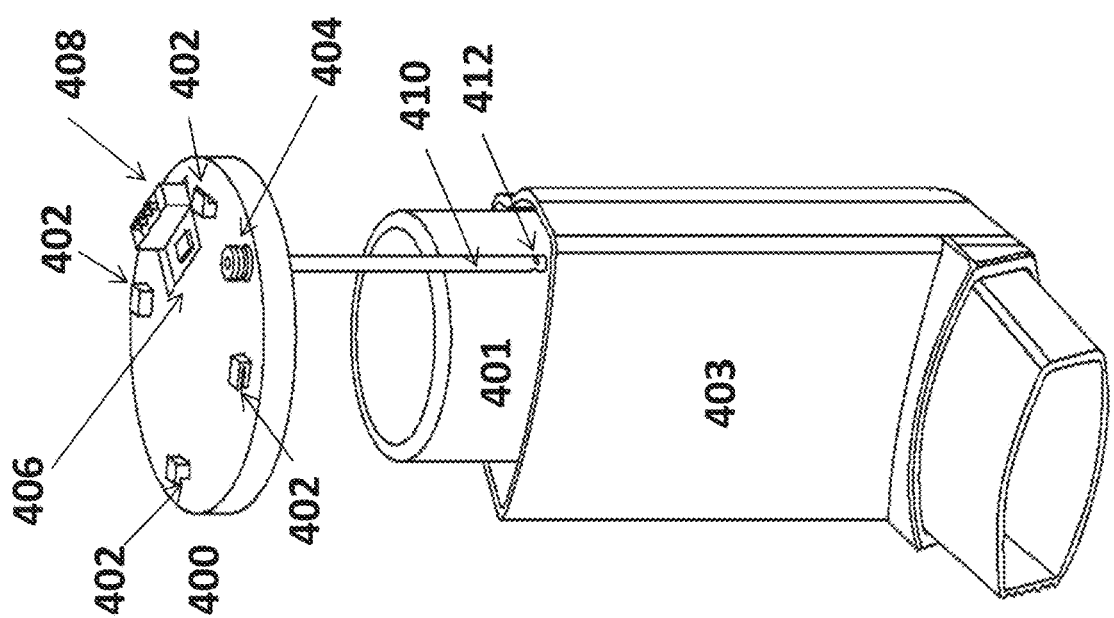
FIG. 4A, FIG. 4B, and FIG. 4C depict a non-limiting example of an adapter as described in accordance with various embodiments of the disclosure.
Figure 4B:
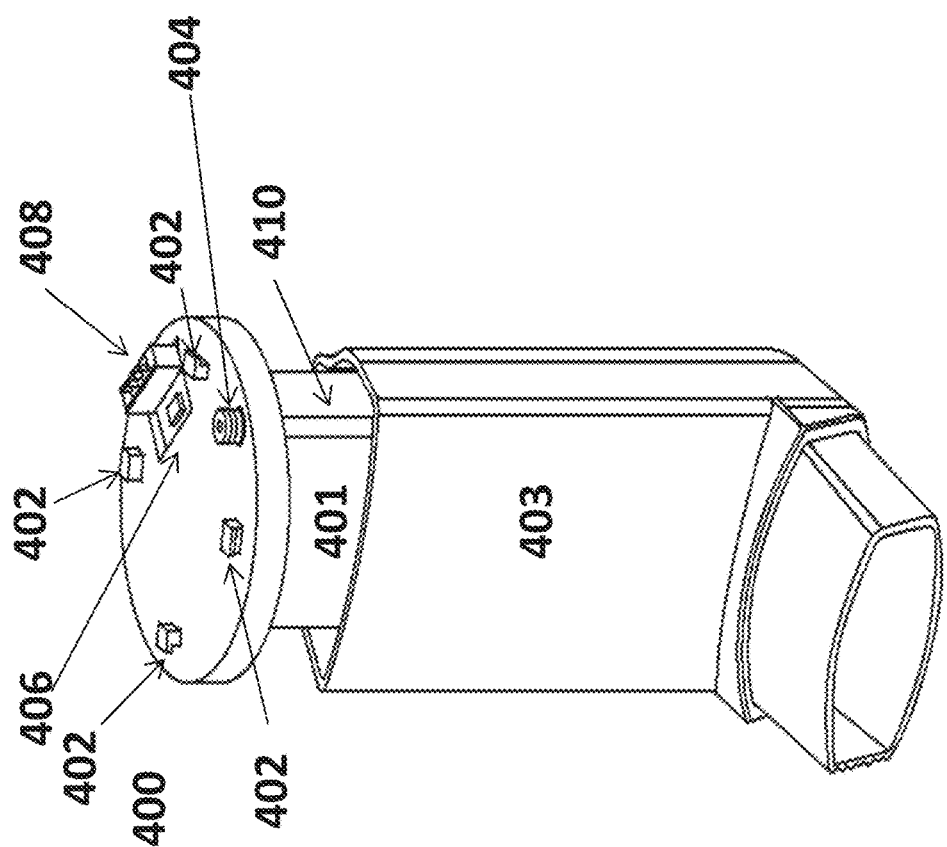
Figure 4C:
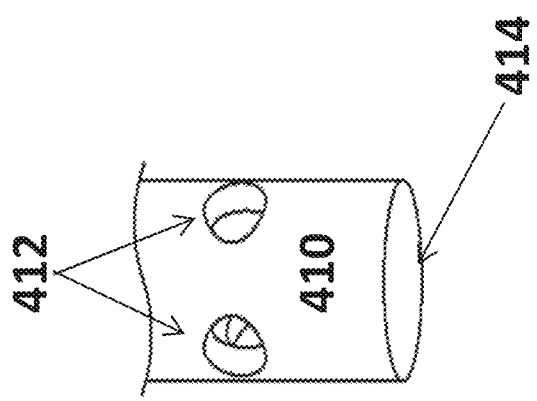
Figure 5A:
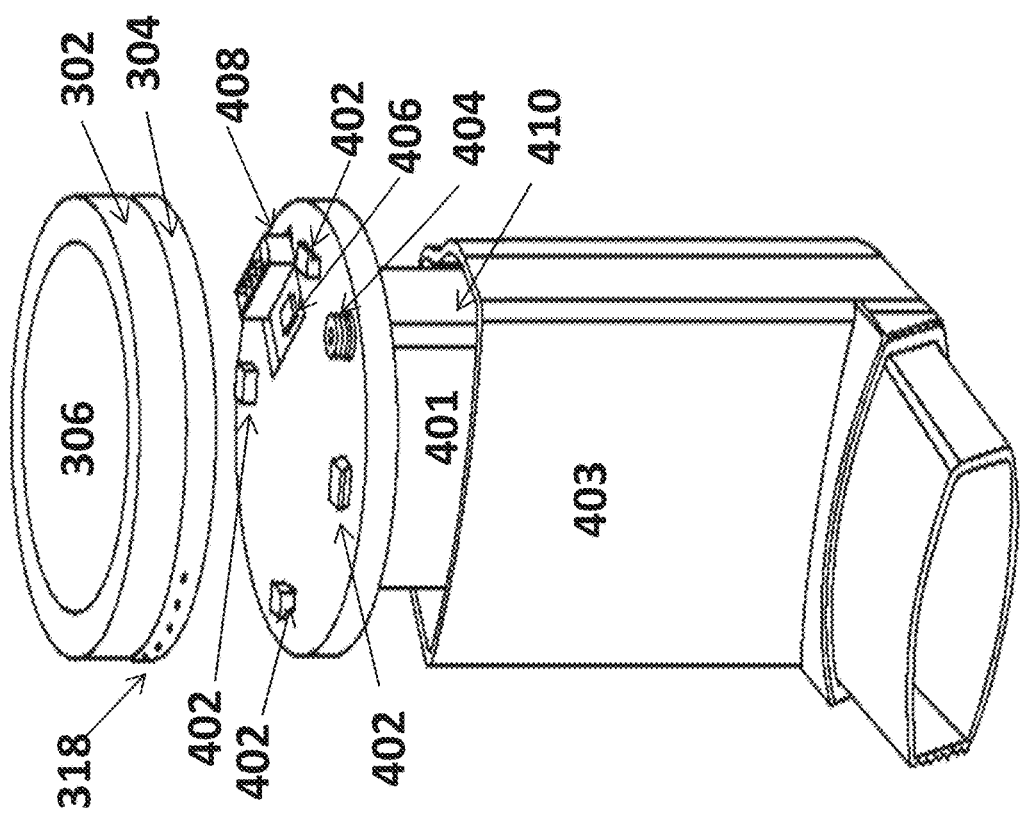
FIG. 5A and FIG. 5B depict a non-limiting example of a sensor device and adapter coupled to an inhaler device.
Figure 5B:
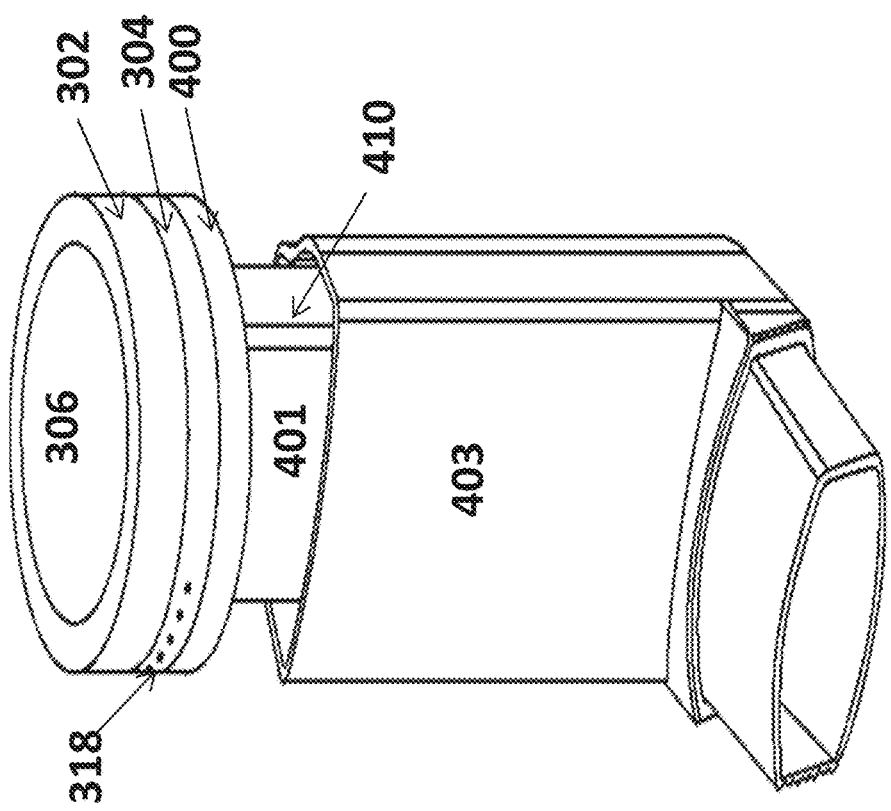
Figure 6A:
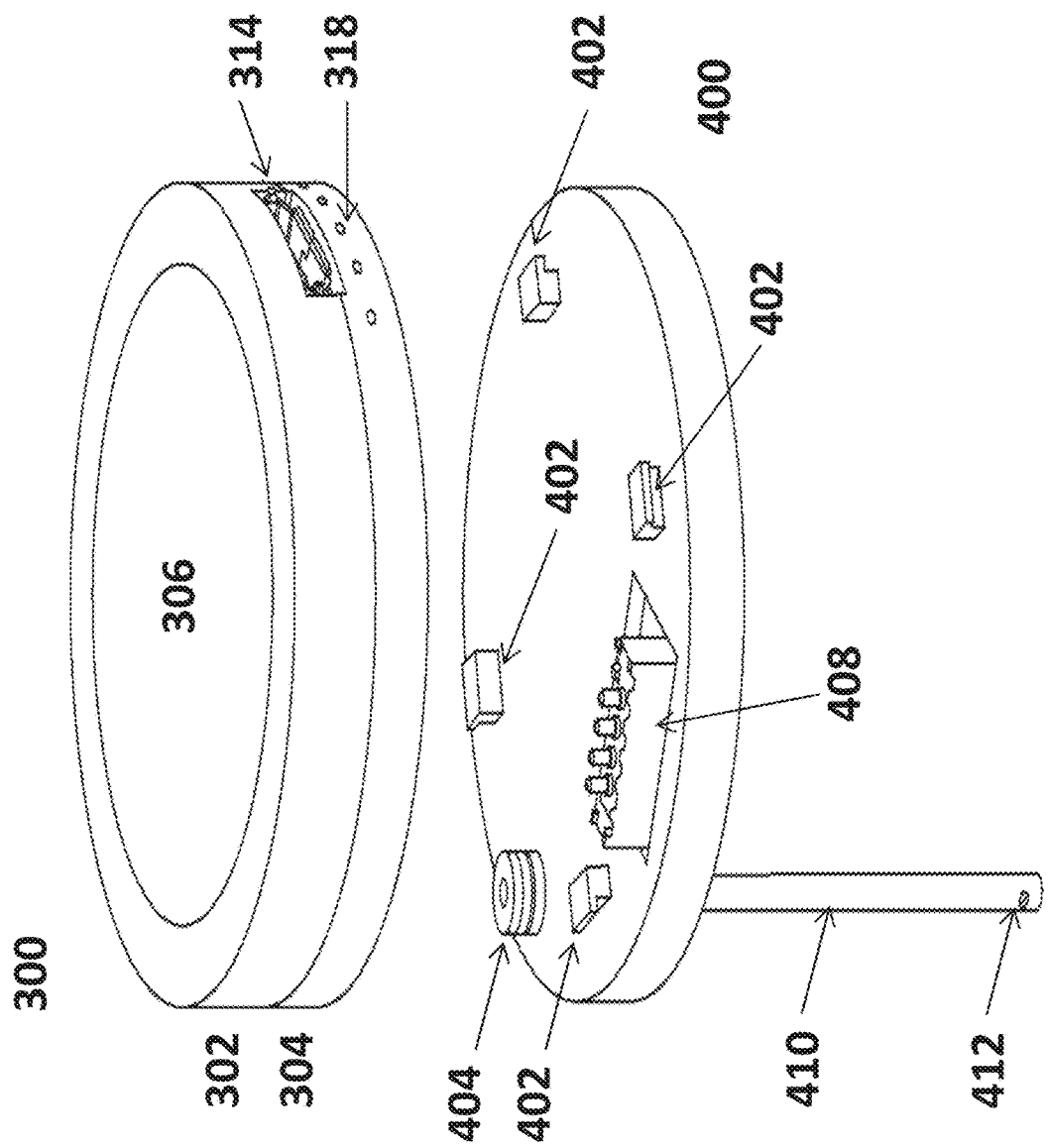
FIG. 6A and FIG. 6B depict a non-limiting example of coupling of a sensor device to an adapter.
Figure 6B:
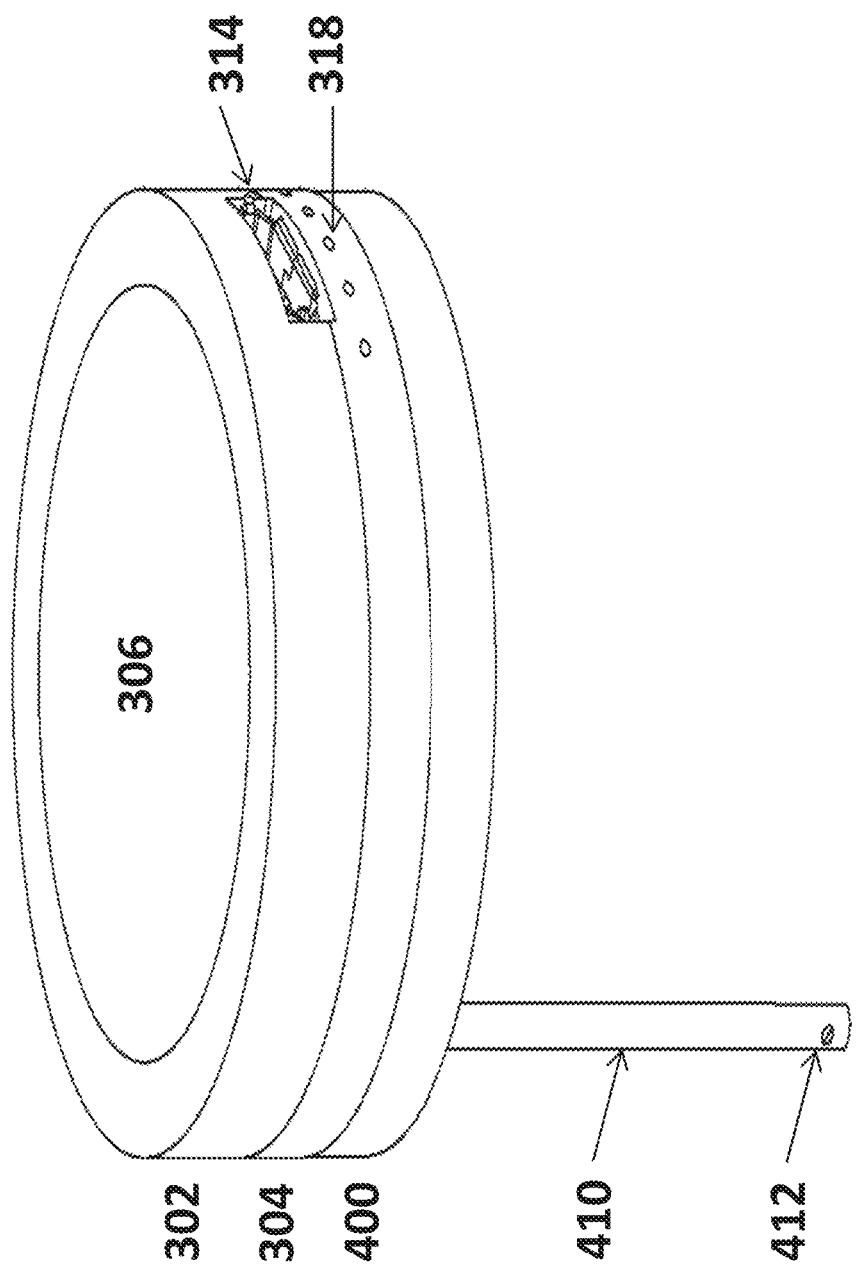

FIGS. 4A-C depict a non-limiting example of a product-specific adapter 400 as envisioned herein that may be used in conjunction with a sensor device 300 for coupling to a medicament device, such as one depicted in FIG. 3. The product-specific adapter 400 may include one or more latches 402 to allow for coupling to a sensor device 300 as described herein. The one or more latches 402 may be, for example, protrusions on the base of the adapter 400 that are complementary to one or more receiving ports 328 on a sensor device 300. The one or more latches 402 may be inserted into the complementary receiving ports 328 of the sensor device 300 allowing the adapter 400 to be affixed to the sensor device 300. The one or more latches 402 may allow for removable coupling of the adapter 400 with the sensor device 300. The adapter 400 may further include a hollow, non-intrusive pressure tap tube 410 for providing access to the air flowing in between the inhaler canister 401 and actuator body 403 during inhalation. The pressure tap tube may be hollow. In some instances, the pressure tap tube may be configured to be located on a side of the adapter and/or the sensor device. The pressure tap tube may be configured to run alongside, or be parallel to the medicament device. The pressure tap tube may be configured to be located towards a mouthpiece of a medicament device, or inhaler such that inhalation of a user can affect air within the pressure tap tube. The pressure tap tube may include one or more pressure tap ports 412. The pressure tap ports may allow inflow or outflow of air through the pressure tap tube, which may be sensed by a pressure sensor (e.g., located on a sensor device). The pressure tap ports may be located on a side of the pressure tap tube to allow sensing of pressure of the moving air going across the pressure tap tube. The pressure tap tube 410 may be configured such that it mates to the sensor device 300 by way of a mating surface 404 and provides a sealed interface to the sensor device's barometer 320 so that the system can accurately detect inhalation. In such cases, the barometer signal may be directly related to the user's inhalation. The pressure tab tube 410 may be positioned into the gap between the inhaler canister 401 and the actuator 403. The adapter 400 may additionally include a cryptographic authenticating device 406 for uniquely identifying the adapter 400 and for preventing cloning or counterfeiting of the adapter 400. The adapter 400 may further include a secure memory block for storing the PSOPs for reading exclusively by the adapter after successful authentication by the authenticating device 406. The adapter 400 may further include an electro-mechanical coupler 408 that allows the adapter 400 to be electronically connected to the sensor device 300 for receiving data from, and/or transmitting data to the one or more sensors and for relaying an output to the indicators on the sensor device 300. For example, the adapter may be configured to transmit one or more parameters described herein to the sensor device. In some instances, the adapter may automatically transmit one or more parameters stored on a memory relating to a medicament device when electrical connection is established between the sensor device and the adapter. Optionally, the adapter may transmit one or more parameters stored on a memory relating to a medicament device when the sensor device and/or adapter is authenticated. FIG. 4B depicts an adapter 400 coupled to an inhaler device. FIG. 4C depicts an expanded view of a distal end of the pressure tap tube 410 comprising pressure tap ports 412 and a pressure tap cap 414.

In one example, the sensor device may be product-agnostic (i.e., not tailored to a specific medicament device). The sensor device may be used in conjunction with a plurality of product-specific adapters each comprising different PSOPs, or with a plurality of product-specific adapters, each comprising the same PSOPs. In this example, the sensor device may be removably attached to a disposable adapter, and then the adapter may be attached to the specific medicament device. Alternatively, in this example, the sensor device may be removably attached to a disposable adapter that is already attached to the specific medicament device. After the medicament device has been exhausted, the sensor device may be removed from the adapter, the product-specific adapter may be disposed along with the empty medicament device, and the sensor device may be attached to a different product-specific adapter. In one non-limiting example, a user may purchase a set or kit comprising one or more sensor devices and a plurality of product-specific adapters, each product-specific adapter comprising PSOPs for a specific medicament device. During normal usage or after the user has exhausted the drug product, the user may dispose of the medicament device and the adapter, and attach the sensor device to a new adapter and medicament device. In this way, the sensor device can be reused a plurality of times.

Figure 10:
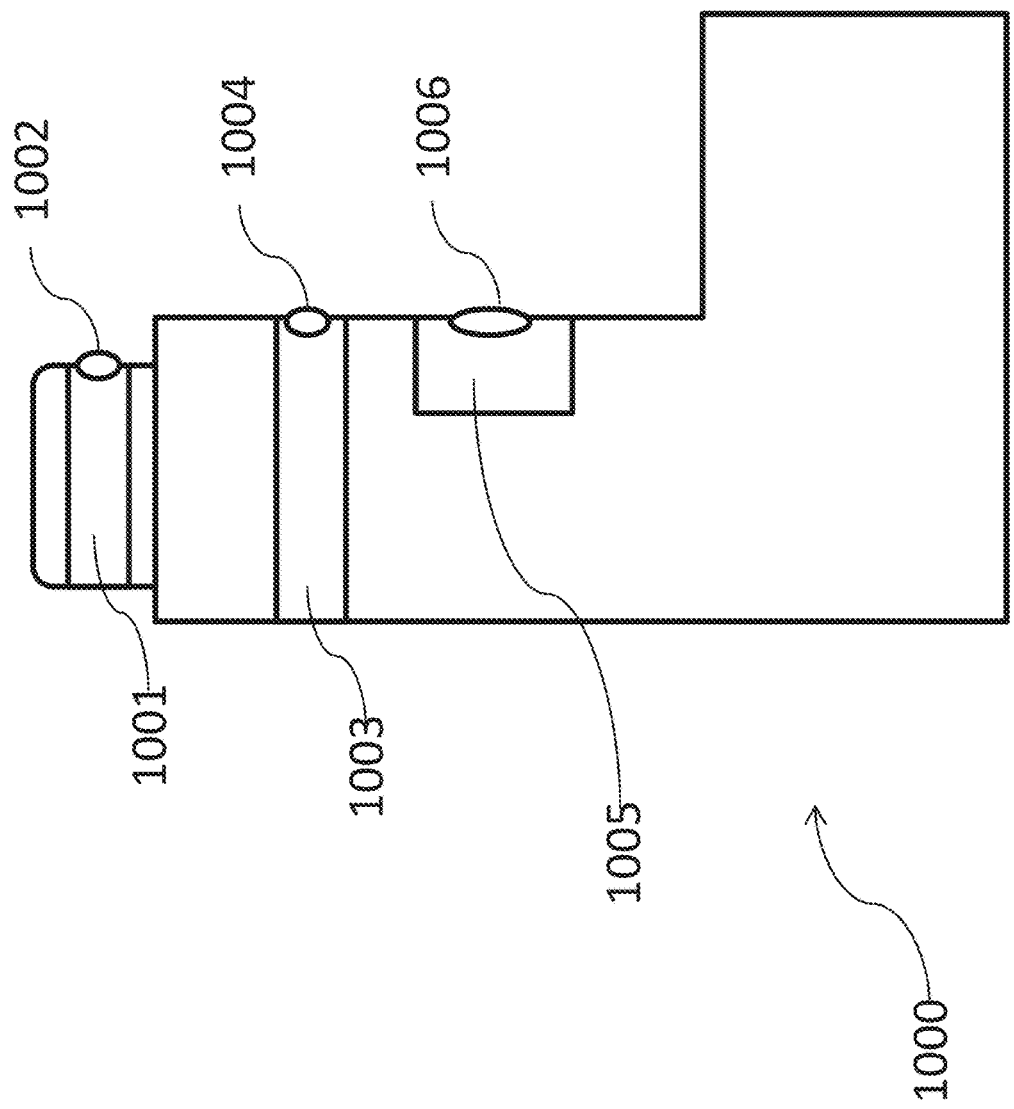
FIG. 10 depicts non-limiting examples of placement of a sensor and a visual indicator (e.g., LED) on an inhaler device.

The sensor device may be affixed to any component of the medicament device, and generally, the sensor device will be affixed such that the one or more sensors contained within the sensor device are capable of sensing or detecting one or more parameters of the medicament device. For example, a sensor device may be affixed to the holder of the medicament device to detect, for example, shake frequency of the medicament device. In another example, a sensor device may be affixed to the canister of the medicament device to detect, for example, shake angle (of the canister relative to its vertical axis). The sensor device may be affixed such that the sensor device does not impede the functionality of the medicament device. In some cases, the sensor device is affixed to a surface of the holder or the canister of the medicament device. The surface may be on the outside or the inside of the holder or the canister. In some cases, the sensor device may be embedded into the holder or the canister of the medicament device, for example, into a plastic or metal component of the medicament device. A portion of the sensor device or the entirety of the sensor device may be embedded into the holder or the canister of the medicament device. FIG. 10 depicts a medicament device 1000 demonstrating three non-limiting examples of positioning of the sensor device on the medicament device. The sensor device may be affixed to the medicament (e.g., with an adhesive strip, or by way of a product-specific adapter) 1001, 1003, 1005. The sensor device may be operably coupled to an indicator or signaling mechanism, such as an LED 1002, 1004, 1006. The LED may be positioned at the front of the device, for example, on the front of the housing or canister 1002, 1004, 1006 of the device such that the visual indicator (e.g., light) may be seen by a user of the device.

Figure 11:
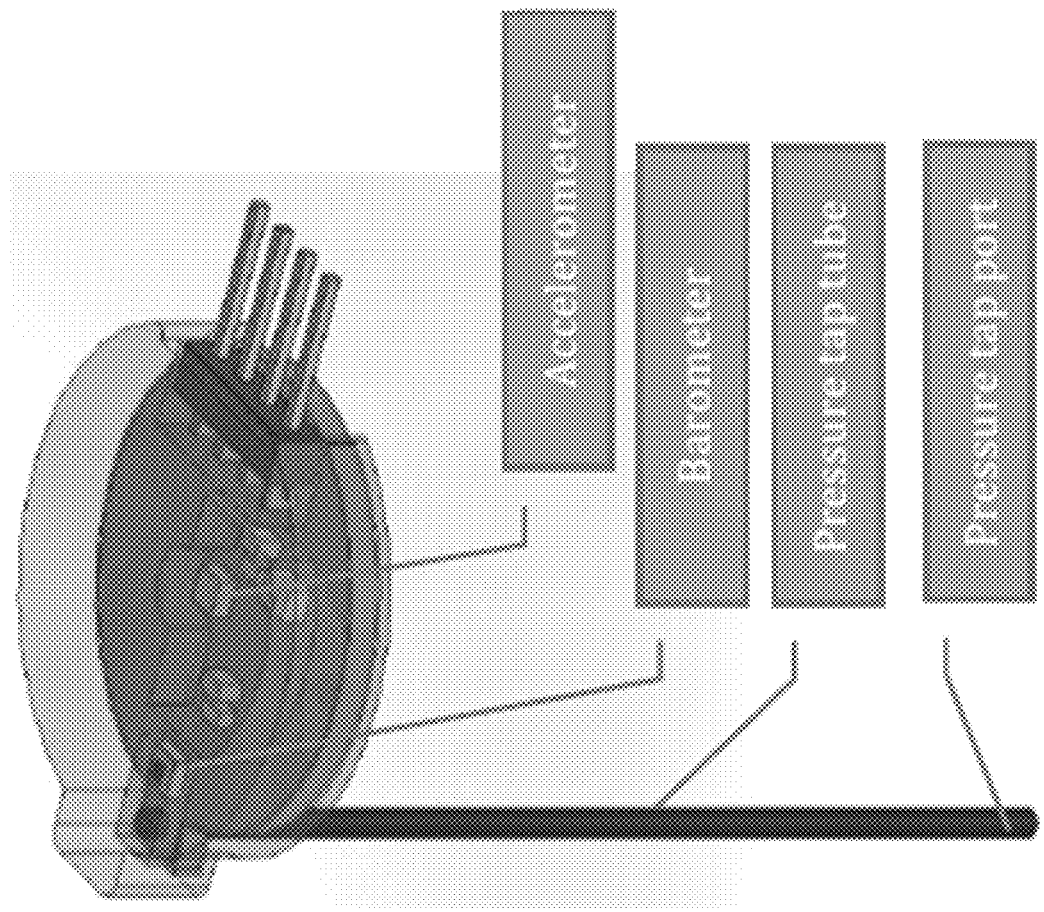
FIG. 11 depicts a non-limiting example of positioning of an accelerometer coincident with a long axis of an inhaler canister in accordance with an embodiment of the disclosure.

In some examples, the adapter may be configured to position the one or more sensors contained within the sensor device in a predetermined relation or manner to the medicament device. FIG. 11 demonstrates a non-limiting example of how a product-specific adapter can position the one or more sensors contained within the sensor device in relation to the medicament device. In this example, the sensor device comprises an accelerometer and a barometer. In order for the accelerometer to properly measure, for example, shake parameters of the medicament device, the accelerometer may need to be positioned along the centerline of the medicament canister. The adapter may function, inter alia, to position the accelerometer along the centerline of the medicament canister. Advantageously, the product-specific adapter may be designed in such a way as to position the accelerometer along the centerline of a specific medicament canister, regardless of the arrangement of the accelerometer within the sensor device. Thus, the present invention allows for the use of a universal sensor device with any configuration or arrangement of sensors with virtually any medicament device. Although a specific example using an accelerometer has been described, it should be understood that the adapter may be used in a similar fashion to position any sensor in a particular configuration with any medicament device.

In some cases, the methods and devices include one or more sensors for the detection of one or more parameters of the medicament device. The one or more parameters may include one or more shake parameters, one or more actuation parameters, one or more inhalation airflow parameters, or any combination thereof. In some cases, the one or more sensors contained within the sensor device detects if the medicament device meets or exceeds a predetermined threshold of the one or more parameters. For example, the one or more sensors may sense or detect if the medicament device has been shaken properly prior to actuation by, e.g., detecting one or more shake parameters. In another example, the one or more sensors may sense or detect if the medicament device has been actuated properly by, e.g., detecting one or more actuation parameters. In some cases, when each of the one or more parameters have met their respective thresholds, the medicament device, when actuated, may deliver an intended dosage range of a drug. In some cases, the one or more sensors may be used to detect when a predetermined threshold of one or more parameters have been met. Each of the one or more parameters may have a predetermined threshold that is specific for a particular medicament device, therefore, in some instances, the one or more sensors may be used to detect if each of the one or more parameters has individually reached its respective threshold. In some cases, the devices provide one or more outputs when a predetermined threshold of each of the one or more parameters has been met or exceeded. In some cases, the devices do not provide an output unless each of the one or more parameters has individually reached its respective threshold. Different medicament devices may have different requirements for proper shaking and actuation. Thus, the sensor device alone or in combination with the adapter may be pre-programmed and customized to operate with a specific medicament device. The sensor device alone or in combination with the adapter may be pre-programmed to detect a particular set of thresholds based on the medicament device and the formulation contained therein.

Any type of sensor may be utilized with the sensor devices described herein. For example, the sensor may be an airflow sensor (e.g., a thermistor or pressure sensor), an integrated flow sensor, a position or displacement sensor, a rate sensor, a tilt sensor, a touch sensor (e.g., an electrode, a capacitive or resistive touch sensor), a shake sensor (e.g., accelerometer), a magnetometer, a global positioning system (GPS) chip, an ambient light sensor, a sensor capable of detecting more than one parameter, and any combination thereof. The selection of the sensor(s) to be used with the medicament device will be dependent on the parameters that will be detected.

In some cases, the one or more sensors detect one or more shake parameters of the medicament device. In some cases, the one or more sensors detect if the medicament device meets or exceeds a predetermined threshold of each of the one or more shake parameters of the medicament device. The one or more shake parameters may include shake duration, shake angle, shake frequency, shake-to-fire interval, or any combination thereof. The term "shake duration" as used herein may refer to the length of time the medicament device is shaken. Shake duration may include from about 1 second to about 30 seconds. For examples, shake duration may include about 1 second, 2 seconds, 3 seconds, 4 seconds, 5 seconds, 6, seconds, 7 seconds, 8 seconds, 9 seconds, 10 seconds, 11 seconds, 12 seconds, 13 seconds, 14 seconds, 15 seconds, 20 seconds, 25 seconds, 30 seconds or greater.

The term "shake angle" as used herein may refer to the angle of the canister of the medicament device during shaking as measured from its vertical axis. For example, a shake angle of 90 degrees would include shaking the canister horizontally. Shake angle may include from about 50 degrees to about 150 degrees. For examples, shake angle may include about 50 degrees, 60 degrees, 70 degrees, 80 degrees, 90 degrees, 100 degrees, 110 degrees, 120 degrees, 130 degrees, 140 degrees, 150 degrees or greater.

The term "shake frequency" as used herein may refer to the number of times (cycles) the medicament device is shaken in a given time period. Shake frequency may be measured in Hertz (Hz) which is defined as the number of cycles in 1 second. Shake frequency may include from about 1.0 Hz to about 5.0 Hz. For examples, shake frequency may be about 1.0 Hz, 1.5 Hz, 2.0 Hz, 2.5 Hz, 3.0 Hz, 3.5 Hz, 4.0 Hz, 4.5 Hz, 5.0 Hz or greater.

The term "shake-to-fire interval" as used herein may refer to the length of time that occurs between the end of a shaking regimen and the actuation of the medicament device. Shake-to-fire interval may be from about 0 seconds to about 30 seconds. For examples, shake-to-fire interval may be about 0 seconds (i.e., immediate actuation after shaking), 1 second, 2 seconds, 3 seconds, 4 seconds, 5 seconds, 6, seconds, 7 seconds, 8 seconds, 9 seconds, 10 seconds, 11 seconds, 12 seconds, 13 seconds, 14 seconds, 15 seconds, 20 seconds, 25 seconds, 30 seconds or greater.

In some cases, the one or more sensors as described herein may be used to monitor a shaking regimen. A shaking regimen may include one or more shake parameters, including one or more of shake duration, shake angle, shake frequency, and shake-to-fire interval. The shaking regimen may be the specific combination of the one or more shake parameters that are required to be performed on the medicament device in order to deliver, upon actuation of the medicament device, an intended dosage range of a drug. The shaking regimen may be specific for a particular medicament device and may be at least partly dependent on the formulation of the drug, one or more characteristics of the medicament device, the volume of the metering valve, the relative mixing efficiency of the drug particles in the suspension with the excipient(s) and/or propellant(s), or any combination thereof. The shaking regimen may be affected by the composition of the formulation present in the canister (e.g., the number of excipients present with the drug in the formulation or the specific composition of the excipients present in the formulation). Therefore, different products each including the same drug may require very different shaking regimens to deliver an intended dosage range.

In some aspects, the methods described herein involve performing a shaking regimen on the medicament device, monitoring one or more shake parameters of the shaking regimen, and actuating the medicament device when a predetermined threshold of the one or more shake parameters has been reached or exceeded. For example, if a shaking regimen included a shake duration of 5 seconds, a shake angle of 60 degrees, and a shake frequency of 2.0 Hz, the medicament device would ideally be actuated after all three shake parameters of the shaking regimen had been reached. In some cases, if one or more of the shake parameters is not met before actuation of the medicament device, the delivered dose of the drug may be different, in some cases substantially different, than the intended target dose.

In some cases, the one or more sensors may detect one or more actuation parameters of the medicament device. For example, the one or more sensors may detect if the medicament device has been properly actuated (e.g., held in a fully actuated state for a defined period of time). The term "actuation" may refer to the act of compressing the canister of a medicament device for a period of time to release a substance contained within the canister or the holder. Actuation of the medicament device, for example, may release a single dose of a formulation contained therein. The one or more sensors may be designed to detect if the medicament device has been only partially actuated, which may indicate that an intended dosage range of a drug has not been released. The one or more actuation parameters may include, without limitation, compression velocity, compression acceleration, actuation hold time, decompression velocity, decompression acceleration, actuation stroke length, and any combination thereof.

"Compression velocity" as used herein may refer to the speed with which the medicament device is compressed (e.g., the speed with which a user pushes or compresses the canister or nasal actuator during actuation). Compression velocity may be from about 10 mm/s to about 100 mm/s. For example, compression velocity may be about 10 mm/s, 15 mm/s, 20 mm/s, 25 mm/s, 30 mm/s, 35 mm/s, 40 mm/s, 45 mm/s, 50 mm/s, 55 mm/s, 60 mm/s, 65 mm/s, 70 mm/s, 75 mm/s, 80 mm/s, 85 mm/s, 90 mm/s, 95 mm/s, 100 mm/s or greater than 100 mm/s.

"Compression acceleration" as used herein may refer to the rate of change in velocity per unit time of the canister or nasal actuator during compression. Compression acceleration may be from about 500 mm/s$^2$ to about 4000 mm/s$^2$. For example, compression acceleration may be about 500 mm/s$^2$, 600 mm/s$^2$, 700 mm/s$^2$, 800 mm/s$^2$, 900 mm/s$^2$, 1000 mm/s$^2$, 1100 mm/s$^2$, 1200 mm/s$^2$, 1300 mm/s$^2$, 1400 mm/s$^2$, 1500 mm/s$^2$, 1600 mm/s$^2$, 1700 mm/s$^2$, 1800 mm/s$^2$, 1900 mm/s$^2$, 2000 mm/s$^2$, 2100 mm/s$^2$, 2200 mm/s$^2$, 2300 mm/s$^2$, 2400 mm/s$^2$, 2500 mm/s$^2$, 2600 mm/s$^2$, 2700 mm/s$^2$, 2800 mm/s$^2$, 2900 mm/s$^2$, 3000 mm/s$^2$, 3100 mm/s$^2$, 3200 mm/s$^2$, 3300 mm/s$^2$, 3400 mm/s$^2$, 3500 mm/s$^2$, 3600 mm/s$^2$, 3700 mm/s$^2$, 3800 mm/s$^2$, 3900 mm/s$^2$, 4000 mm/s$^2$ or greater than 4000 mm/s$^2$.

"Actuation hold time" as used herein may refer to the amount of time a medicament device is held in its fully actuated state. "Fully actuated" may refer to maximal compression of the canister of a medicament device. Actuation of a medicament device may include compression of a medicament device and may include an "actuation hold time window", for example, a period of time in which a medicament device is held in its fully actuated state. An actuation hold time window may be from about 0 seconds to about 30 seconds. For example, an actuation hold time window may be about 0 seconds (immediate release), 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds or greater than 30 seconds.

In some cases, the one or more sensors may detect the decompression velocity. "Decompression velocity" as used herein may refer to the speed with which the medicament device is decompressed (e.g., speed with which a user releases or decompresses the canister or nasal actuator after actuation). Decompression velocity may be from about 10 mm/s to about 100 mm/s. For example, decompression velocity may be about 10 mm/s, 15 mm/s, 20 mm/s, 25 mm/s, 30 mm/s, 35 mm/s, 40 mm/s, 45 mm/s, 50 mm/s, 55 mm/s, 60 mm/s, 65 mm/s, 70 mm/s, 75 mm/s, 80 mm/s, 85 mm/s, 90 mm/s, 95 mm/s, 100 mm/s or greater than 100 mm/s.

In some cases, the one or more sensors may detect the decompression acceleration. "Decompression acceleration" as used herein may refer to the rate of change of velocity per unit time during decompression of the canister or nasal actuator during decompression. Decompression acceleration may be from about 500 mm/s$^2$ to about 4000 mm/s$^2$. For example, decompression acceleration may be about 500 mm/s$^2$, 600 mm/s$^2$, 700 mm/s$^2$, 800 mm/s$^2$, 900 mm/s$^2$, 1000 mm/s$^2$, 1100 mm/s$^2$, 1200 mm/s$^2$, 1300 mm/s$^2$, 1400 mm/s$^2$, 1500 mm/s$^2$, 1600 mm/s$^2$, 1700 mm/s$^2$, 1800 mm/s$^2$, 1900 mm/s$^2$, 2000 mm/s$^2$, 2100 mm/s$^2$, 2200 mm/s$^2$, 2300 mm/s$^2$, 2400 mm/s$^2$, 2500 mm/s$^2$, 2600 mm/s$^2$, 2700 mm/s$^2$, 2800 mm/s$^2$, 2900 mm/s$^2$, 3000 mm/s$^2$, 3100 mm/s$^2$, 3200 mm/s$^2$, 3300 mm/s$^2$, 3400 mm/s$^2$, 3500 mm/s$^2$, 3600 mm/s$^2$, 3700 mm/s$^2$, 3800 mm/s$^2$, 3900 mm/s$^2$, 4000 mm/s$^2$ or greater than 4000 mm/s$^2$.

In some cases, the one or more sensors may detect an actuation stroke length. "Actuation stroke length" as used herein may refer to the maximum amount the medicament device is compressed during actuation. In some cases, the actuation stroke length is the mechanical compression limit for the medicament device. Actuation stroke length may be from about 3 mm to about 20 mm. For example, actuation stroke length may be about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm or greater than 20 mm.

In some cases, the one or more sensors may detect one or more inhalation airflow parameters. For example, the one or more sensors may detect one or more inhalation airflow parameters, for example, during inhalation of a delivered amount of a formulation by a user of the medicament device. In some cases, the one or more sensors may detect inspiratory airflow rate. "Inspiratory airflow rate" as used herein may refer to the speed of airflow during inspiration. Inspiratory airflow rate may be a readout, for example, for the strength of a breath or a sniff. The inspiratory airflow rate may be from about 30 liters/minute to about 100 liters/minute depending on the flow resistance of the medicament device and the breathing capability of the user. For example, the inspiratory airflow rate may be about 30 liters/minute, 35 liters/minute, 40 liters/minute, 45 liters/minute, 50 liters/minute, 55 liters/minute, 60 liters/minute, 65 liters/minute, 70 liters/minute, 75 liters/minute, 80 liters/minute, 85 liters/minute, 90 liters/minute, 95 liters/minute, 100 liters/minute or greater than 100 liters/minute.

In some cases, the one or more sensors may detect inhaled volume. "Inhaled volume" as used herein may refer to the volume of air inhaled during a breath or a sniff. The inhaled volume may be about from about 0.5 liters to about 5 liters. For example, the inhaled volume may be about 0.5 liters, about 1.0 liter, about 1.5 liters, about 2.0 liters, about 2.5 liters, about 3.0 liters, about 3.5 liters, about 4.0 liters, about 4.5 liters, about 5.0 liters or greater than 5.0 liters.

In some cases, the one or more sensors may detect inflow velocity. "Inflow velocity" as used herein may refer to the velocity measured at a point in the stream of air inhaled during a breath or sniff. In some cases, the inflow velocity may be about from about 0.1 meters/second to about 3.0 meters/second. For example, the inflow velocity may be about 0.1 meters/second, 0.2 meters/second, 0.3 meters/second, 0.4 meters/second, 0.5 meters/second, 0.6 meters/second, 0.7 meters/second, 0.8 meters/second, 0.9 meters/ second, 1.0 meters/second, 1.1 meters/second, 1.2 meters/ second, 1.3 meters/second, 1.4 meters/second, 1.5 meters/ second, 1.6 meters/second, 1.7 meters/second, 1.8 meters/ second, 1.9 meters/second, 2.0 meters/second, 2.1 meters/ second, 2.2 meters/second, 2.3 meters/second, 2.4 meters/ second, 2.5 meters/second, 2.6 meters/second, 2.7 meters/ second, 2.8 meters/second, 2.9 meters/second, 3.0 meters/ second or greater than 3.0 meters/second.

The devices described herein may further guide a user in the proper usage and/or care of a medicament device. In some cases, the devices described herein may detect the expiration date of a drug contained within the medicament device. For example, the devices described herein may determine whether the date of actual usage of the drug falls inside or outside the expiration date of the drug. The devices may, by way of example, instruct the user that the drug contained within the medicament device has expired, and may instruct the user to cease usage of the drug or to replace the drug. The expiration of the drug may be determined by the manufacturer of the drug and may be marked on the drug product itself or the box of the drug product.

In some cases, the devices described herein may detect whether the medicament device has been properly primed prior to use. The devices may detect the number of times the medicament device is to be actuated prior to initial use of the medicament device, and may determine whether the user has properly primed the medicament device. In some cases, the devices described herein may provide guidance to the user on how to properly prime the medicament device, by, for example, informing the user how many times the medicament device should be actuated prior to initial use. When the devices detect that the medicament device has not been properly primed, the devices may alert the user. The priming regiment for a particular medicament device may be provided by the manufacturer of the medicament device, and may range from 2 to 10 actuations, and in some cases from 0 to 5 actuations. Optionally, the priming regiment may be equal to about 0, 1, 2, 3, 4, 5, 6, 7, 8, 9, or 10 actuations or steps.

In some cases, the devices described herein may detect whether the medicament device has been properly re-primed, for example, after a period of non-use. The device may detect whether a medicament device has not been used for a specified period of time, and then may instruct a user to re-prime the medicament device by actuating the medicament device a number of times before resuming use of the medicament device. The re-priming regiment may include from 2 to 10 actuations after about 5 to 7 days of non-use. In some cases, the number of re-priming actuations is from 0 to 5 actuations. Optionally, the re-priming regiment may be equal to about 0, 1, 2, 3, 4, 5, 6, 7, 8, 9, or 10 actuations or steps. In some cases, the duration until re-priming is from 0 to 30 days. Depending on the type of medicament device, the duration until re-priming (e.g., recommended duration) may be equal to about 0, 2, 4, 6, 8, 10, 12, 14, 16, 18, 20, 22, 24, 26, 30 days, or any value there in between.

In some cases, the devices described herein may provide guidance to a user such as the wait time between actuations. Proper administration of a drug from some medicament devices may require a user to wait for a period of time after an actuation event before inhaling. In such cases, the devices may instruct the user to actuate the device, wait for a defined period of time, and then inhale. In some cases, the wait time between actuations may be from about 0 to about 60 seconds. For example, the wait time between actuations may be from about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds.

In some cases, the devices described herein may instruct the user to clean the medicament device after a specified period of use. For example, the devices may detect when a specified number of actuations have occurred, and then instruct the user that a cleaning protocol should be performed on the medicament device.

In some cases, the devices described herein produce one or more outputs when the one or more parameters has met a predetermined threshold. In some cases, the devices are operably coupled to an indicator or a signaling mechanism and provide an indication to the user that the medicament device is in a condition suitable for delivering an intended dosage range of a drug. For example, when the sensor device has detected that one or more parameters of the medicament device has met or exceeded a predetermined threshold, the sensor device may produce one or more outputs that includes an indication to indicate that the medicament device is in a certain state or condition. For example, the sensor device may provide an indication to the user that the medicament device has been properly shaken. In another example, the sensor device may provide an indication to the user that the medicament device has been properly actuated. The indication may be a visual indication, an audible indication, or both. For example, as shown in FIG. 12A, the device may include a light source, such as a light-emitting diode (LED) that produces a visual indication 1201 (e.g., a light) when a predetermined threshold of the one or more parameters has been met or exceeded. The visual indication may be a change in the color of the light (for example, a red light indicates that the device is not properly shaken and a green light indicates that the device has been properly shaken). The visual indication can be the presence or absence of light (for example, a light is off when the device has not been properly shaken and the light switches on after the device has been properly shaken). In some cases, the visual indication can be a flashing of a light. The light may be on any component of the sensor device, on the adapter, or on the medicament device itself, although generally the light is positioned such that it is easily seen by the user. For example, the light can be on the holder (e.g., nasal spray device, or actuator or mouthpiece of an inhaler) of the medicament device. In some cases, the light is positioned on the medicament device such that it may be seen by the user when the medicament device has been placed in the user's mouth without having to first remove the medicament device from the mouth. In some cases, the indication is an audible indication. An audible indication may be used, for example, when a device user is visually impaired (e.g., blind, colorblind). An audible indication may be a beep, a chime, a buzz, music, or any other audible indication, as shown in FIG. 12B. In some cases, an audible indication may be the sound of a voice speaking instructions to the user, as shown in FIG. 12C. In some cases, the indication is a vibration of the device, as shown in FIG. 12D. In some cases, the devices include both a visual indication and an audible indication. In some cases, the devices include a plurality of different visual indications or a plurality of different audible indications that may indicate different conditions of the device (e.g., one indication indicates the device has been properly shaken and another indication indicates the device has been properly actuated).

In some aspects, the one or more outputs include data. The data may be collected by the sensor device, stored by the sensor device, or both. In some cases, the data may be transmitted to and/or read from a mobile device (e.g., a cell phone, a tablet), a computer, a cloud application or any combination thereof. The data may be transmitted by any means for transmitting data, including, but not limited to, downloading the data from the sensor (e.g., USB, RS-232 serial, or other industry standard communications protocol) and wireless transmission (e.g., Bluetooth®, ANT+, NFC, or other similar industry standard). The data may include information as to the conditions and/or status of the device at the time of actuation. For example, the data may include information on how the device was shaken, information on how the device was actuated, information on how the formulation was delivered to the device user (e.g., volume of air that was inhaled, etc.), information on the environmental conditions of the device (e.g., temperature, humidity), information regarding the date, time, and geographical location of the device, and the like. The information may be displayed as a report. The report may be displayed on the screen of a mobile device or a computer. The report may be transmitted to a healthcare provider or a caregiver. In some cases, the devices described herein may provide data including, without limitation, information about how the medicament device was shaken (e.g., one or more shake parameters such as shake angle, shake frequency, etc.), when the medicament device was actuated (e.g., within the shake-to-fire interval, etc.), how the medicament device was actuated (e.g., one or more actuation parameters such as compression velocity, actuation hold time, etc.), and when and how the medicament device was decompressed. The data may then be downloaded and provided to a healthcare provider or caregiver to assess whether the patient is properly using the medicament device and delivering the correct dose of drug. In some instances, the data may be downloaded to an electronic health record. Optionally, the data may comprise or be part of an electronic health record. For example, the data may be uploaded to an electronic health record of a user of the devices and methods described herein.

Figure 13:
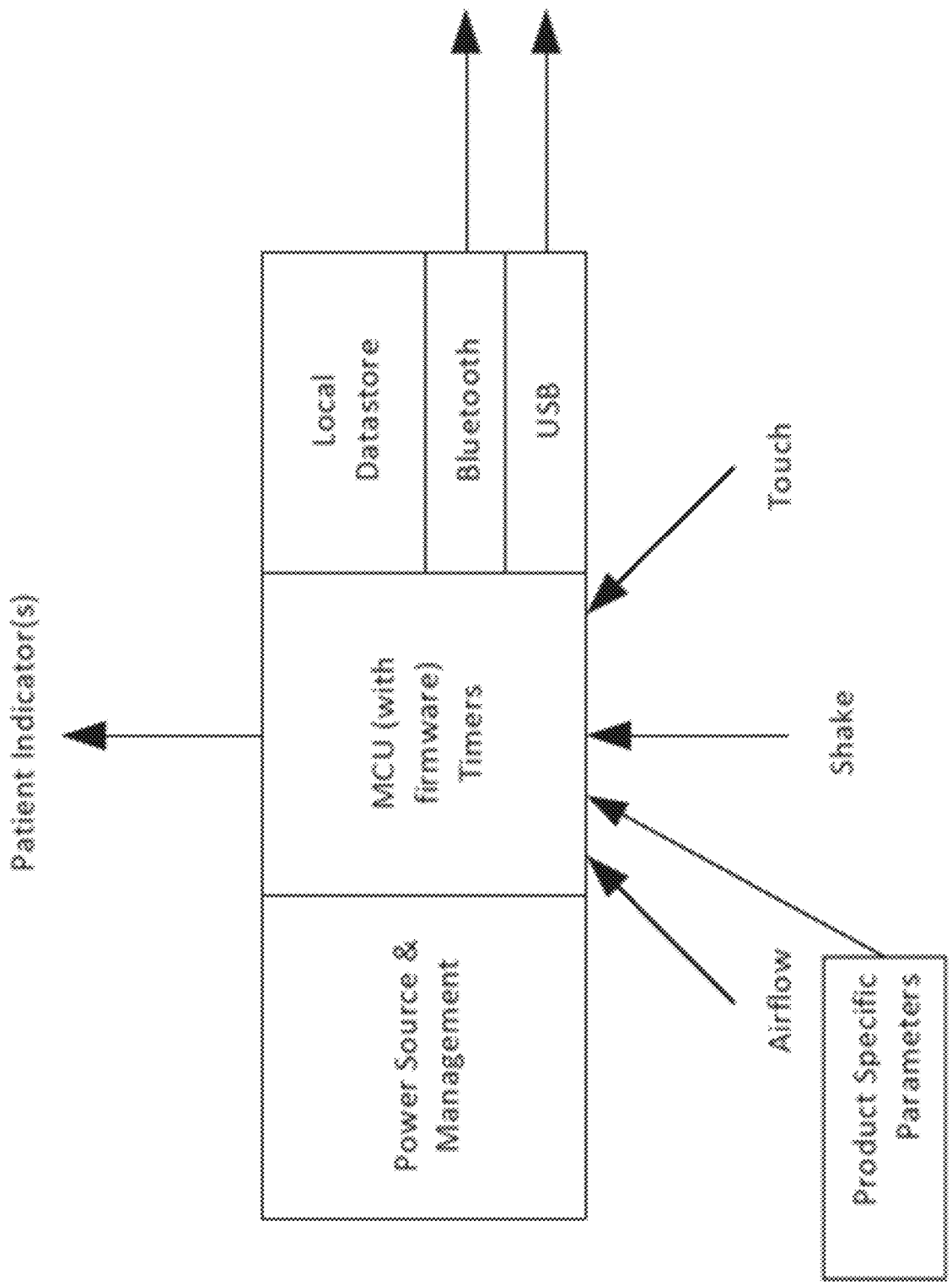
FIG. 13 depicts a non-limiting example workflow of a system as described herein.

The devices described herein may include one or more additional components. In some cases, the devices may include a power source, such as a battery, one or more timers, local data storage media, other supporting electronics such as resistors, capacitors, connectors, wireless antennae, switches, and the like. FIG. 13 depicts a non-limiting example of a workflow of a system as described herein.

In another aspect, methods and devices are provided for detecting a shake-to-fire interval for actuating an inhaler or nasal device, wherein when the one or more sensors detect the shake-to-fire interval, the sensor device, the adapter, or the medicament device produces one or more outputs. In some cases, the shake-to-fire interval indicates a period of time during which the medicament device, when actuated, may deliver an intended dosage range of a drug. For example, an indication may be provided to a medicament device user that the medicament device has been properly shaken and is in a condition suitable to deliver an intended dosage range of a drug upon proper actuation (i.e., the shake-to-fire interval has not expired). In some cases, the shake-to-fire interval detected by the one or more sensors includes a first time point at the start of the shake-to-fire interval and a second time point at the end of the shake-to-fire interval. In some cases, the one or more sensors detect the first time point (e.g., immediately after the one or more sensors have detected that the medicament device has been properly shaken) and the devices produce an output, such as an indicator that the medicament device is ready to be actuated. The one or more sensors may also detect a second time point, for example, at the end of the shake-to-fire interval, that indicates the medicament device is no longer in a suitable condition to deliver an intended dosage range of a drug upon actuation. For example, if the medicament device is not actuated within a specified time frame after shaking, the formulation contained within the medicament device may not be homogeneous and actuation of the medicament device may not provide an intended dosage range of the drug. For example, a suspension formulation may need to be properly shaken prior to actuation as the insoluble drug particles may settle to the bottom of the canister. Proper shaking may re-suspend the insoluble drug particles such that actuation of the device would deliver an intended dosage range of the drug. However, after a time period, the insoluble drug particles will again settle to the bottom of the canister. Therefore, actuation outside of this shake-to-fire interval may not deliver an intended dosage range of the drug. In some cases, the one or more sensors detect this second time point (i.e., at the end of the shake-to-fire interval) and the devices produce an output. In some cases, this output is another indication that the medicament device is no longer in a condition suitable to deliver an intended dosage range of the drug. The indication can be a visual indication or an audible indication or both as described herein. In some cases, the presence of a light may indicate that the medicament device is ready to be actuated and the absence of the light may indicate that the medicament device is not ready to be actuated. In some instances, the indication is a change in color (e.g., from green to red). In some cases, the one or more sensors may detect one or more parameters of the medicament device as described herein, for example, one or more shake parameters (e.g., shake angle, shake frequency, shake duration, shake-to-fire interval). In some cases, the one or more sensors may detect when a predetermined threshold of the one or more parameters has been met or exceeded. In some cases, the medicament device may be unable to be actuated if the shake-to-fire interval is not detected. For example, the medicament device may be locked or otherwise prevented from being actuated outside of the shake-to-fire interval. In some cases, the medicament device may be automatically actuated when the shake-to-fire interval is detected. The shake-to-fire interval may vary and will be dependent on the type of medicament device being used, the formulation of the drug, and other factors. The devices described herein may be pre-programmed and customized to detect the appropriate shake-to-fire interval for each medicament device.

In another aspect, methods and devices are provided comprising one or more sensors for detecting an actuation hold time window of a medicament device, wherein when the one or more sensors detect the actuation hold time window, the devices produce one or more outputs. The actuation hold time window, as described herein, may include a period of time in which the medicament device is held in a fully actuated position. The actuation hold time window may indicate a length of time after which the medicament device, when held in an actuated state, has delivered an intended dosage range of a drug. In some cases, the actuation hold time window may include a first time point at the start of the actuation hold time window and a second time point at the end of the actuation hold time window. In some cases, the one or more sensors may detect one or more actuation parameters, as described herein. In some cases, the one or more sensors may detect when a predetermined threshold of the one or more actuation parameters has been met or exceeded, and this may indicate that the medicament device is being held in a fully actuated state.

The actuation hold time window may be dependent on the type of the medicament device, the formulation of the drug, and other factors. In some cases, the devices described herein may produce one or more outputs, such as an indication, when a second time point (e.g., at the end) of the actuation hold time window has been detected. The indication may be a visual indication, an audible indication or both as described herein. The one or more sensors may further detect one or more additional parameters of the medicament device, such as shake parameters or inhalation airflow parameters.

In some aspects, methods are provided for using the devices described herein. In one aspect, a method is provided comprising: (a) shaking the medicament device, wherein the shaking comprises one or more shake parameters; and (b) actuating the medicament device when a predetermined threshold of the one or more shake parameters is met, wherein when the one or more sensors detect that the predetermined threshold has been met, the device produces one or more outputs.

In another aspect, a method is provided comprising: (a) compressing the medicament device for a period of time, wherein the period of time comprises an actuation hold time window; and (b) decompressing the medicament device when the device produces an output, wherein when the one or more sensors detect the end of the actuation hold time window, the device produces the output.

Figure 14:
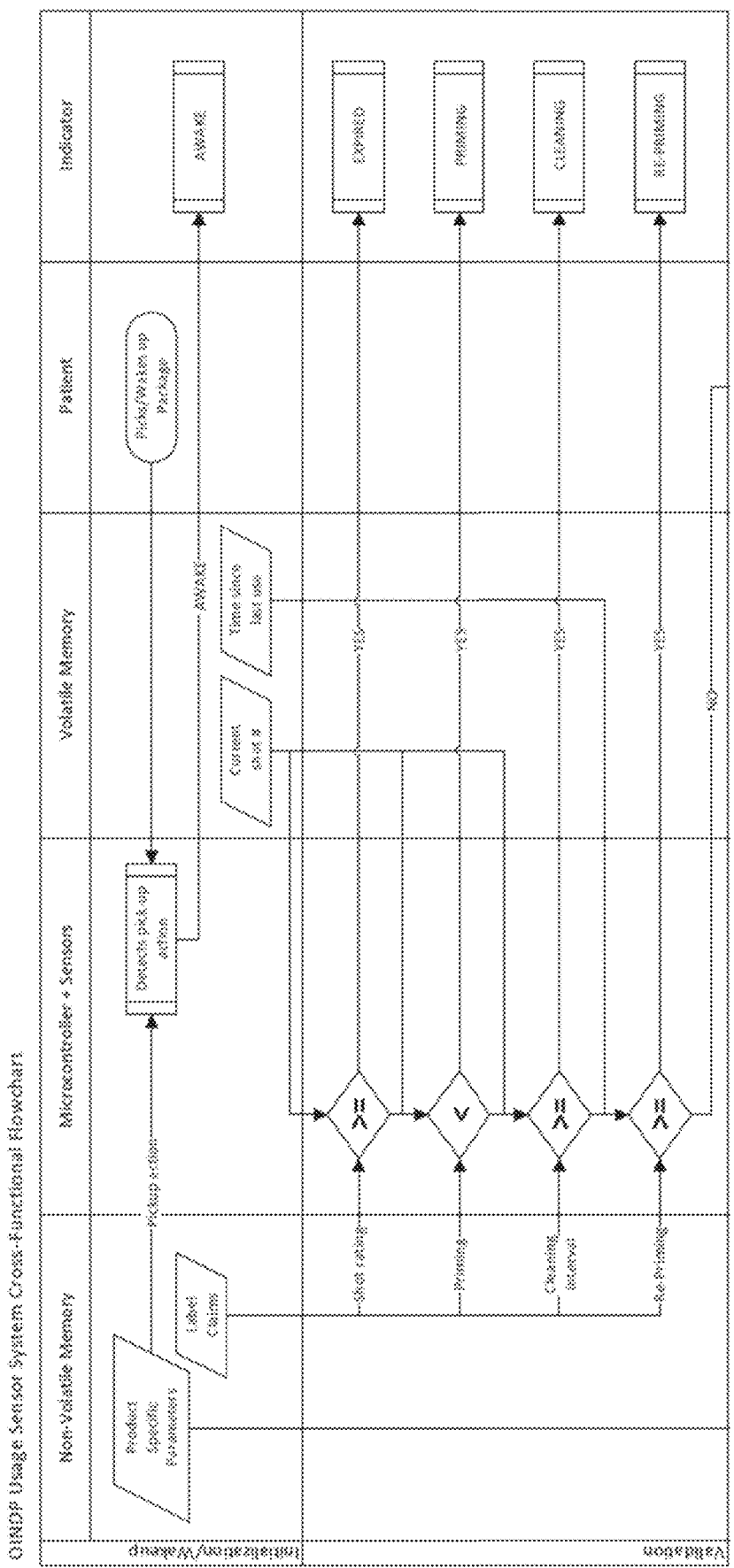
FIG. 14 depicts a non-limiting example workflow of a method of using the systems described herein.
Figure 14:
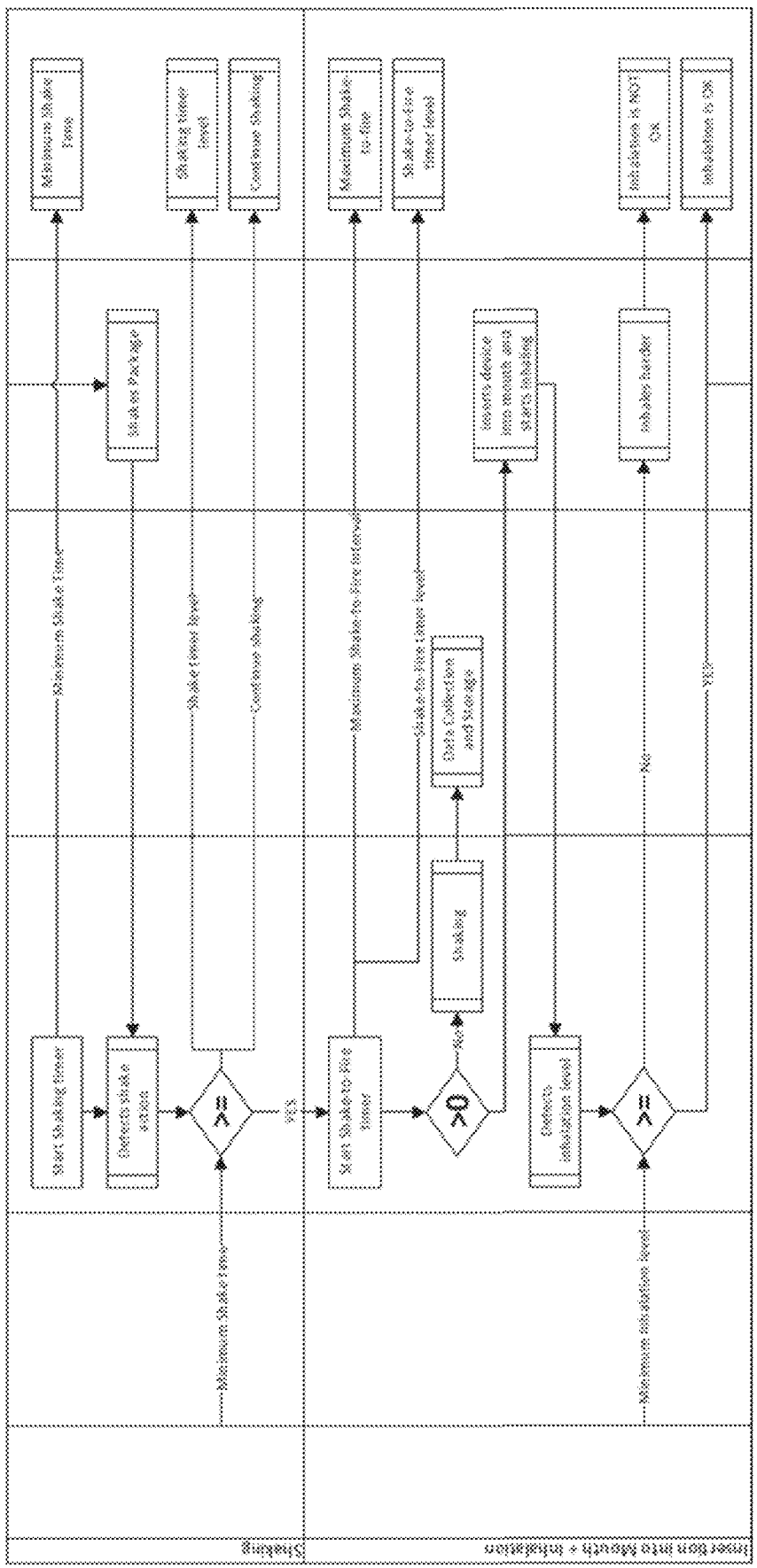
Figure 14:
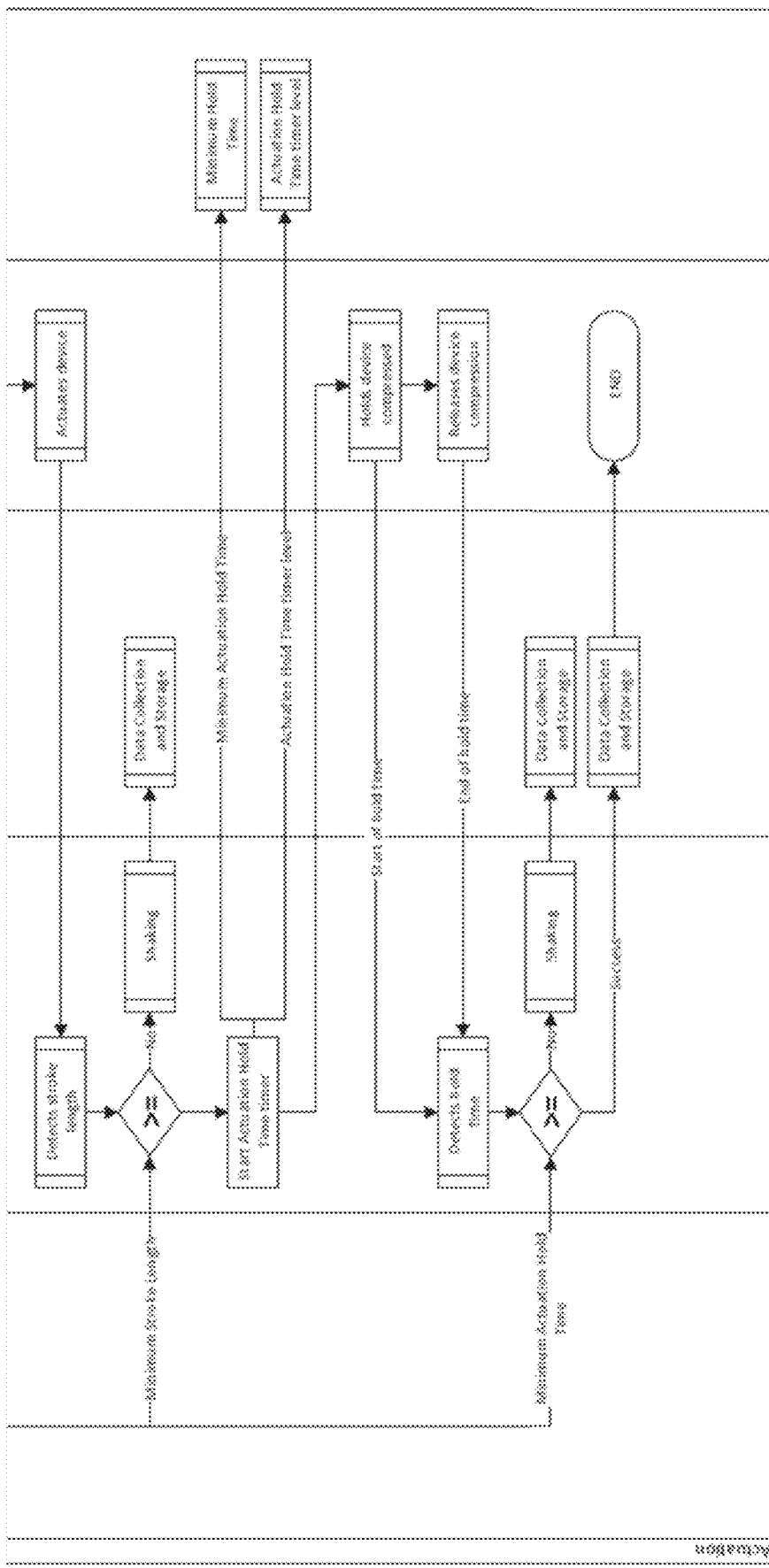

FIG. 14 depicts a non-limiting workflow of a method of using the devices as described herein. It should be understood that FIG. 14 is merely intended to be illustrative and variations on the methods of using the devices are also envisioned herein. Variations on the methods may be dependent on the various aspects of the devices, as have been described in detail throughout the disclosure. For example, the order of the workflow may be modified or steps may be added or subtracted from the method to accommodate the systems.

Figure 15C:
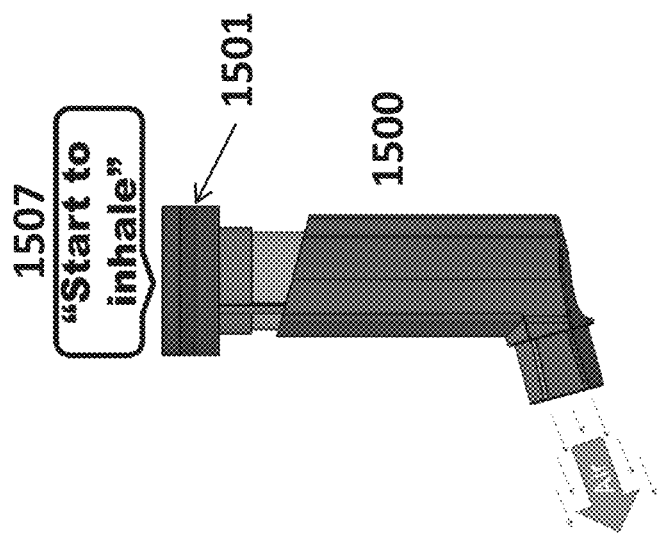
FIG. 15A, FIG. 15B, FIG. 15C, FIG. 15D, and FIG. 15E depict a non-limiting example of a method of using a device as described herein.
Figure 15B:
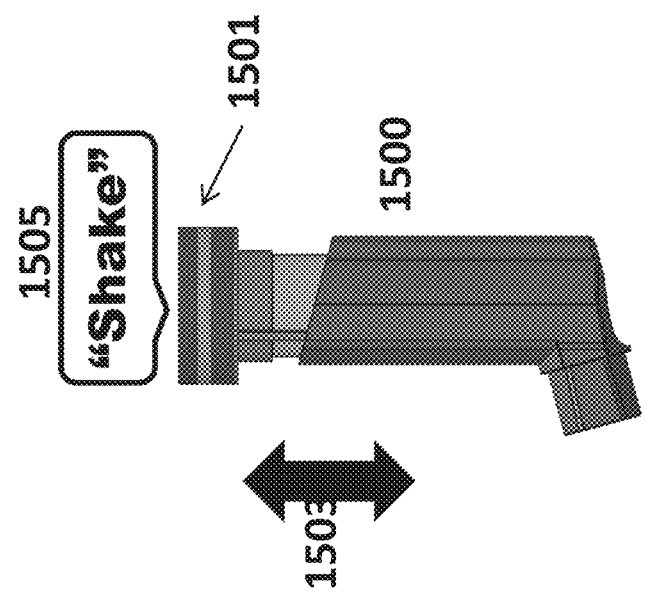
Figure 15A:
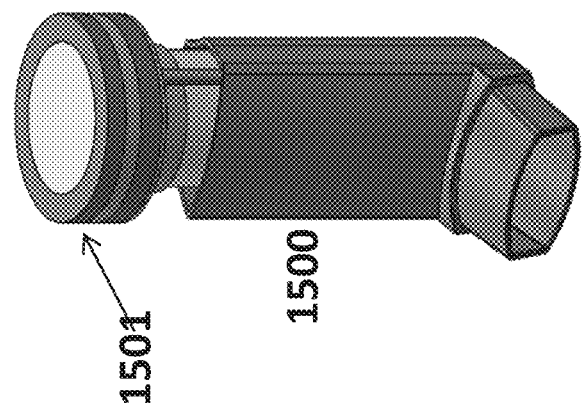
Figure 15E:
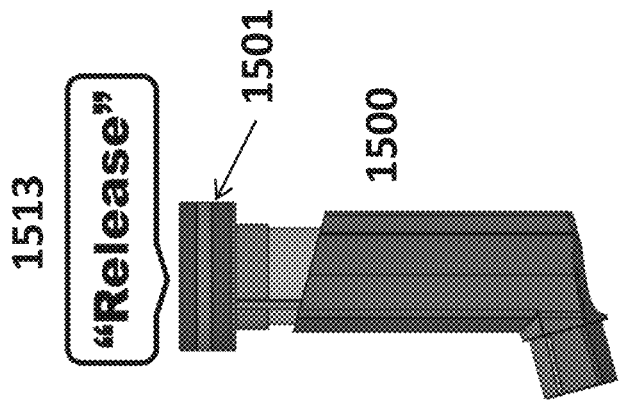
Figure 15D:
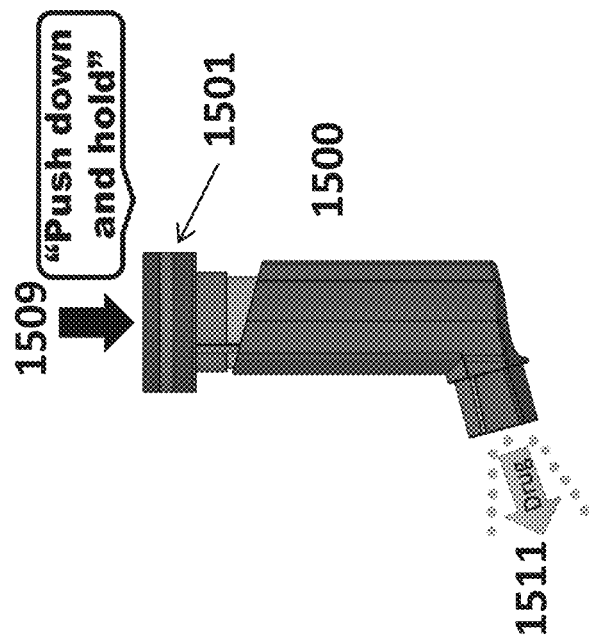

The sensor device may guide or instruct a user through each of the one or more parameters of a medicament device described throughout such that, when the user follows the instructions of the device, the accuracy of an emitted dosage may be improved. FIGS. 15A-E depict a non-limiting example of how a sensor device as provided by the disclosure may guide a user of a medicament device to deliver the correct dose of a drug. FIG. 15A depicts a medicament device 1500 with a sensor device and adapter 1501 affixed thereto. The sensor device 1501 may provide an output 1505 (e.g., an audible indication) to the user indicating that the medicament device 1500 is ready to be shaken as shown in FIG. 15B. The user may then shake 1503 the medicament device 1500. As shown in FIG. 15C, the sensor device 1501 may sense when the medicament device has been properly shaken (e.g., a predetermined threshold of one or more shake parameters has been met). The device may then provide an output 1507 to the user indicating that the shake-to-fire interval has begun and that the user should begin to inhale. As shown in FIG. 15D, the sensor device may then provide an output 1509 to the user indicating to the user to actuate the medicament device 1500. The user may then actuate the medicament device by compressing and holding down the canister which then delivers a dosage of a drug 1511 to the user. As shown in FIG. 15E, the sensor device 1501 may then provide an output 1513 to the user to indicate that the canister should be decompressed.

Figure 16:
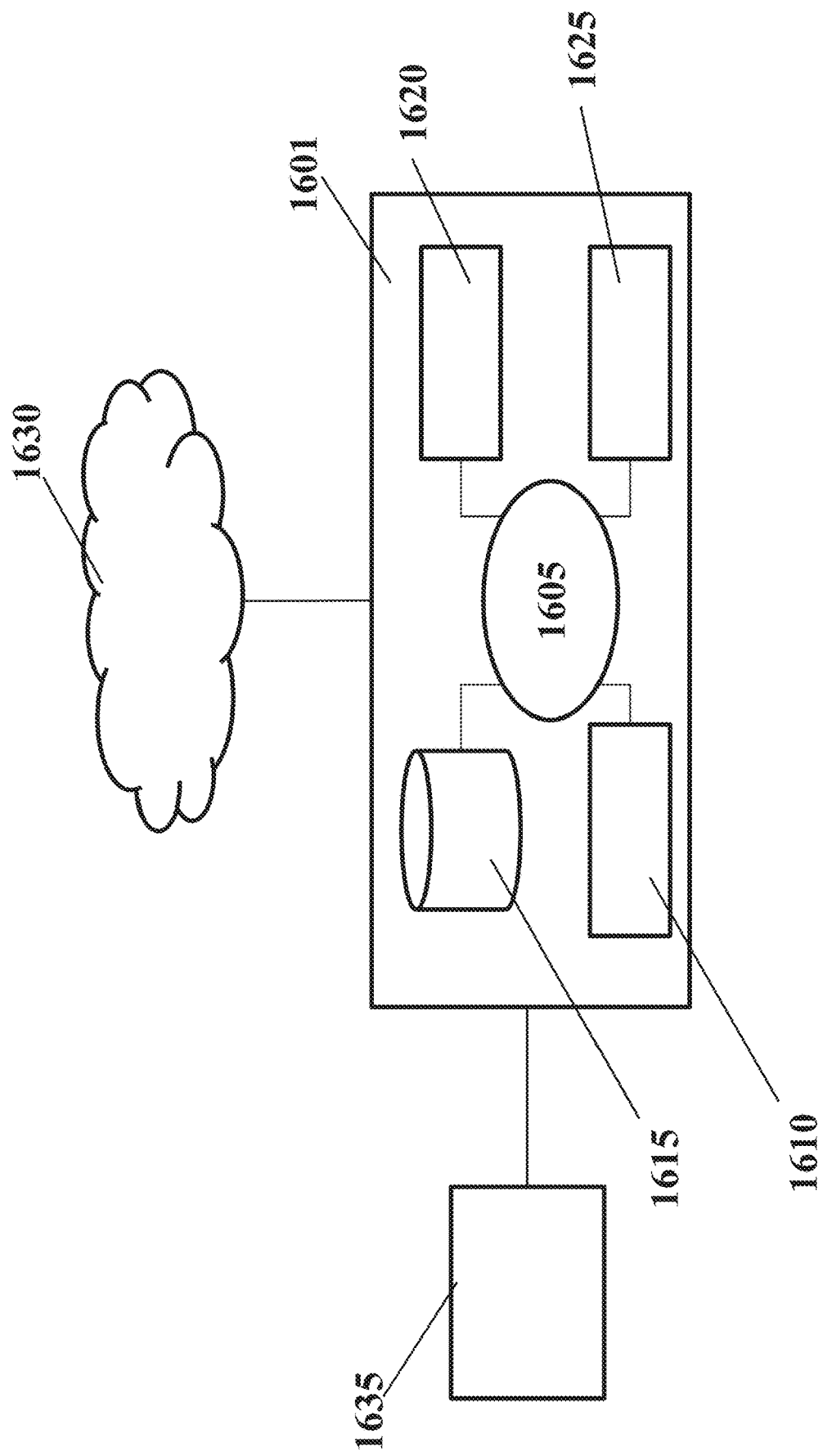
FIG. 16 depicts a non-limiting example of a computer system suitable to be used with a device of the disclosure.

The present disclosure further provides computer control systems that are programmed to implement the methods of the disclosure. FIG. 16 shows a computer system 1601 that is programmed or otherwise configured to operate a sensor device. The computer system 1601 can regulate various aspects of sensor devices, systems and methods of the present disclosure, such as, for example, automatically processing parameters associated with a medicament device as presently described herein. The computer system 1601 can execute a guidance program configured to guide a user to properly use the medicament device. The computer system 1601 can be an electronic device (e.g. sensor device, adapter, etc) of a user or a computer system that is remotely located with respect to the electronic device. The computer system 1601 can be a part of a sensor device or an adapter, individually or collectively. The electronic device can be a mobile electronic device such as a phone, IPAD, tablet, etc.

The computer system 1601 includes a central processing unit (CPU, also "processor" and "computer processor" herein) 1605, which can be a single core or multi core processor, or a plurality of processors for parallel processing. The computer system 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The computer system 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the computer system 1601, can implement a peer-to-peer network, which may enable devices coupled to the computer system 1601 to behave as a client or a server.

The CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and writeback.

The CPU 1605 can be part of a circuit, such as an integrated circuit. One or more other components of the system 1601 can be included in the circuit. In some cases, the circuit is an application specific integrated circuit (ASIC).

The storage unit 1615 can store files, such as drivers, libraries and saved programs. The storage unit 1615 can store user data, e.g., user preferences and user programs. The computer system 1601 in some cases can include one or more additional data storage units that are external to the computer system 1601, such as located on a remote server that is in communication with the computer system 1601 through an intranet or the Internet.

The computer system 1601 can communicate with one or more remote computer systems through the network 1630. For instance, the computer system 1601 can communicate with a remote computer system of a user (e.g., in need of medication). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1601 via the network 1630.

Methods as described herein can be implemented by way of machine (e.g., computer processor) executable code stored on an electronic storage location of the computer system 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1601 may be in communication with various other devices 1635. Although one device 1635 is shown, the computer system 1601 may be in communication with a plurality of other devices, such as adapters, or medicament devices. For example, the medicament device may comprise wired or wireless communication capabilities (e.g., RFID chip, etc). In such instances, a sensor device as referred to herein (e.g., with or without an adapter) may communicate with a medicament device.

The computer system 1601 can include or be in communication with an electronic display (not shown) that comprises a user interface (UI) for providing, for example, one or more controls or input elements to enable a user to control the sensor device 1635. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1605. The algorithm may be executed in some instances once an instruction from a user is received (e.g., through the computer system 1601), and may effect operation of the sensor device 1635. The algorithm can receive one or more signals through one or more sensors of the sensor device 1635, and in some cases adjust the manner in which guidance is provided to a user through the sensor device 1635.

The algorithm can execute or implement various aspects of methods provided herein. For example, the algorithm may be executed to generate the guidance (e.g. in form of data or signals) which is then communicated to a user via visual or auditory modes. The sensor device (e.g. processing unit of the sensor device) may further process the instructions to implement or execute various aspects of the methods.

In some instances, the algorithm may be programmed, or otherwise configured to determine or select appropriate parameters for using the medicament device to provide an effective usage session (e.g., of using the medicament device or dispensing a drug formulation). In some instances, the algorithm may be executed to provide, or guide a user according to manufacturer suggested parameters such that an inhalation session provided to a user is better, or more efficient to achieve a desired effect (e.g., in accordance with manufacturer standards). Optionally, the algorithm may be executed to provide further instructions to the sensor device. For example, via execution of the algorithm, instructions may be generated that instruct a processor on board the sensor device to receive parameters for guiding a user to use a medicament device, e.g., from an adapter via a wireless or wired mode. As another example, via execution of the algorithm, instructions may be generated that instruct a processor on board the sensor device to receive parameters from other sources, such as directly from a medicament device (e.g., via RFID chip, etc) or from the internet. For example, the sensor device may be programmable or may communicate with a server (e.g., cloud based server) which comprises parameters configurable by a user, guardians, or a healthcare provider. The user, guardian, or healthcare provider may be able to store appropriate parameters online which may be read by the sensor device as described throughout, which may process and use the parameters to guide a user.

In some instances, the algorithms may be executed by a third party. For example, the algorithms may be executed by a healthcare provider. The healthcare provider may provide an input (e.g. an instruction) to a cloud based platform, which may generate parameters that are transmitted to a user's sensor device (and/or mobile device in communication with the sensor device) which then executes the algorithm. Execution of the algorithm may further generate instructions that are transmitted to a sensor device. The instructions may instruct a processor on board the sensor device to run a user guidance program, and an indicator (e.g., visual or auditory indicator) may then output an indication to guide a user.

The computer system 1601 can execute an algorithm to provide a set of instructions. For example, relevant parameters for a medicament device may be transmitted (e.g. wired or wirelessly) to a communication module of a sensor device 1635 and be received by a processing unit (e.g., of the sensor device). The processing unit may or may not process the set of parameters and further instruct an indicator for transmission one or more indications to guide a user in using a medication device.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Sensor Device for Use with an Inhaler Device

Figure 17A:
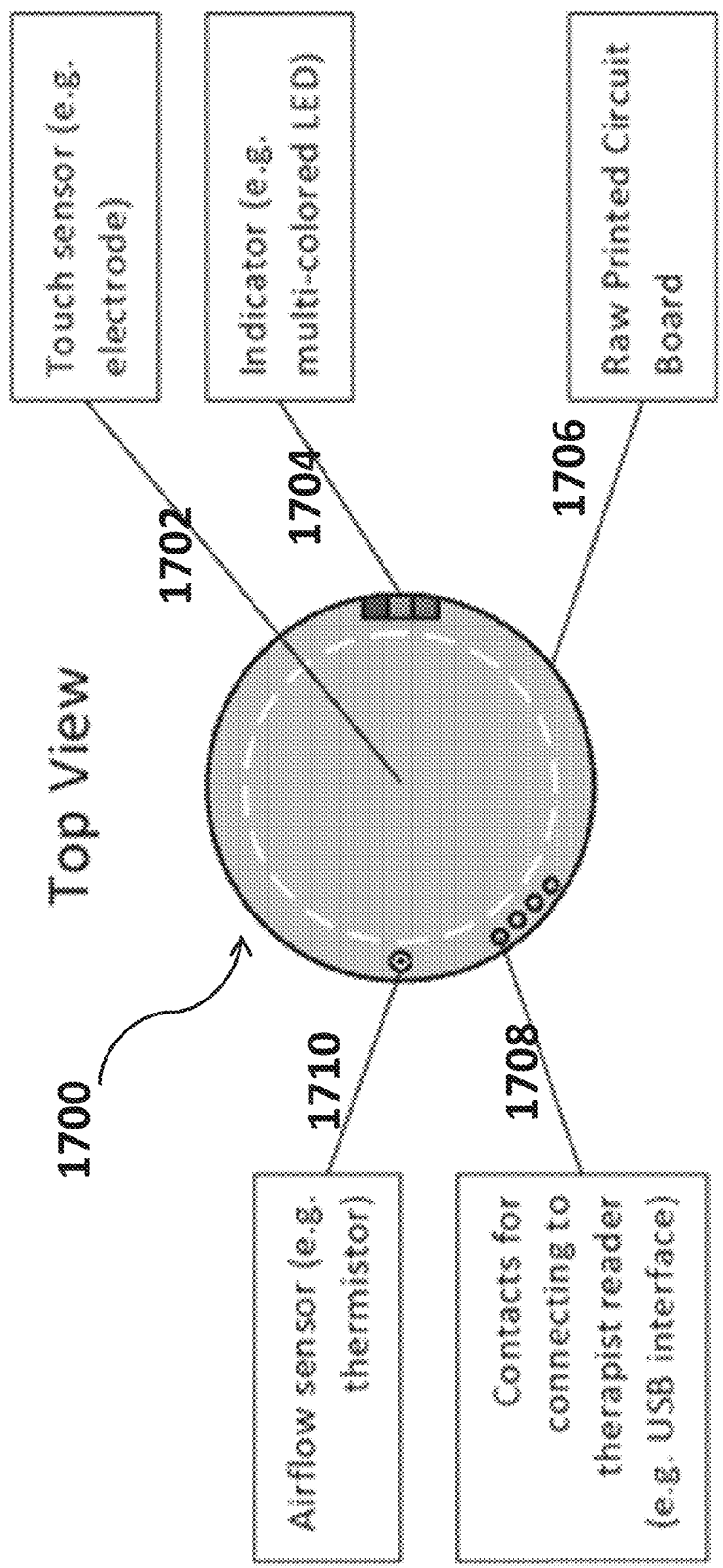
FIG. 17A, FIG. 17B, FIG. 17C, and FIG. 17D depict various views of an exemplary system as described herein.
Figure 17B:
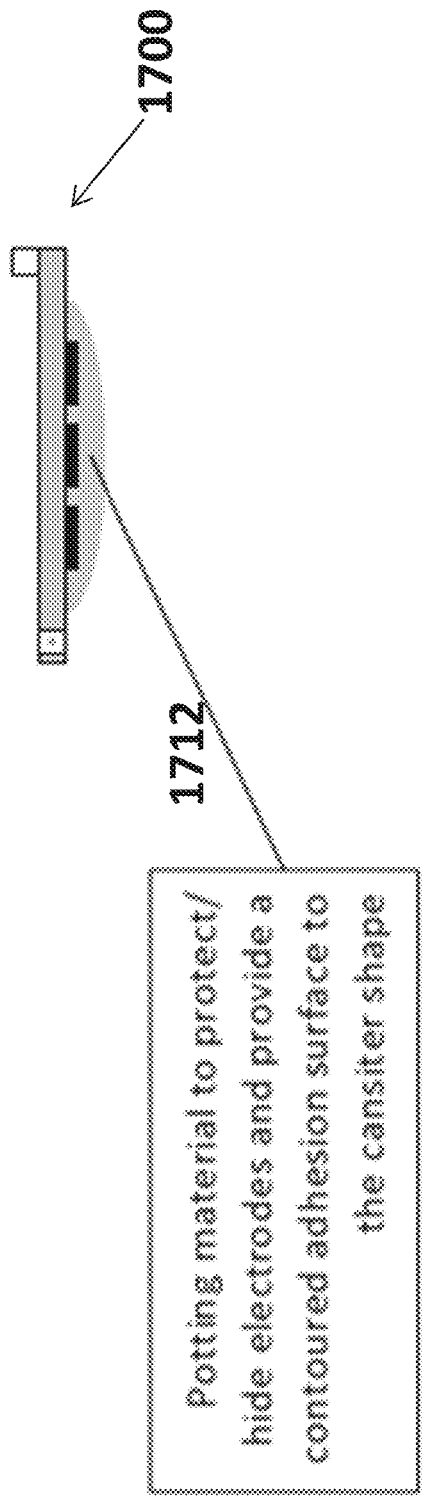
Figure 17C:
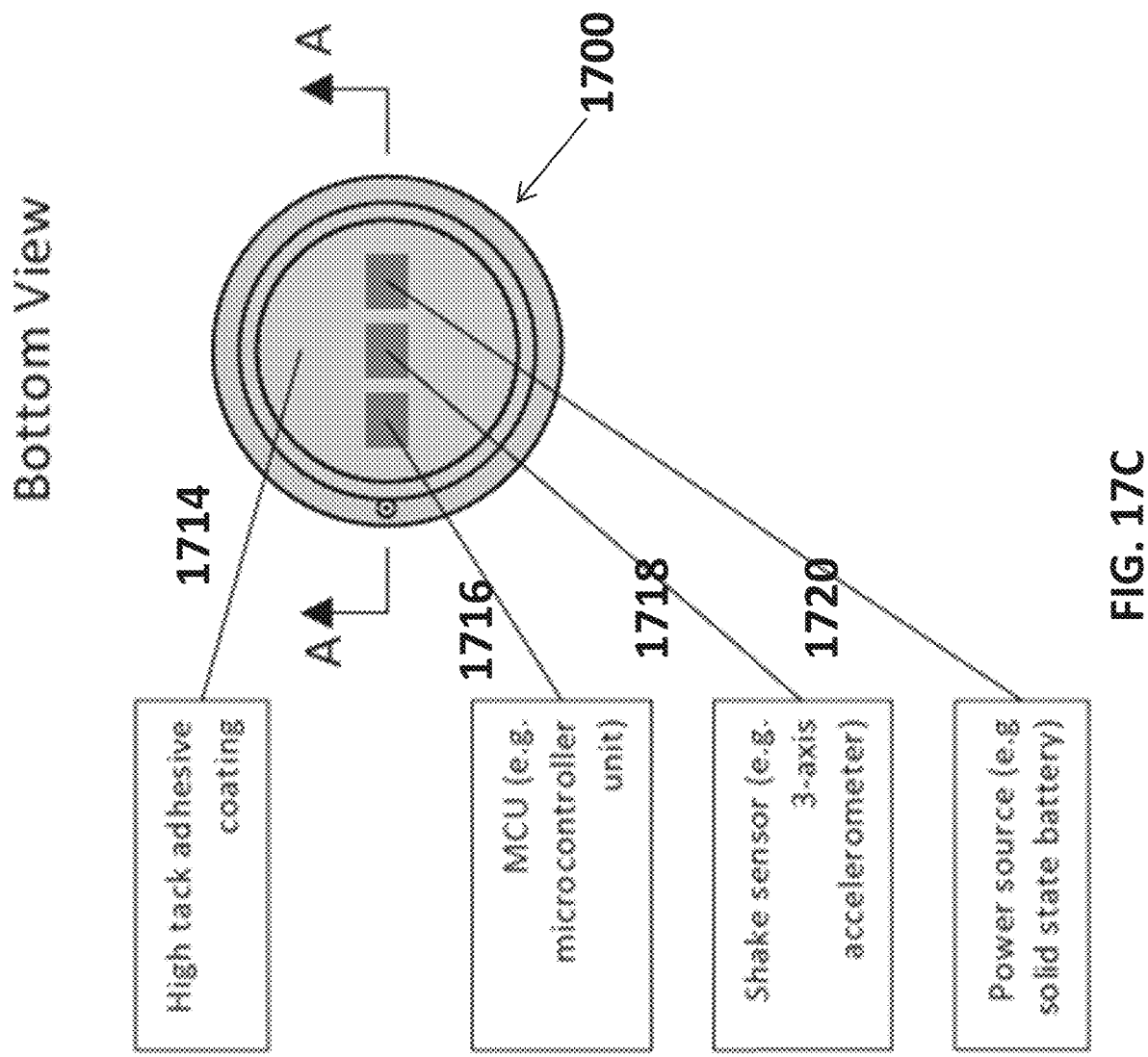
Figure 17D:
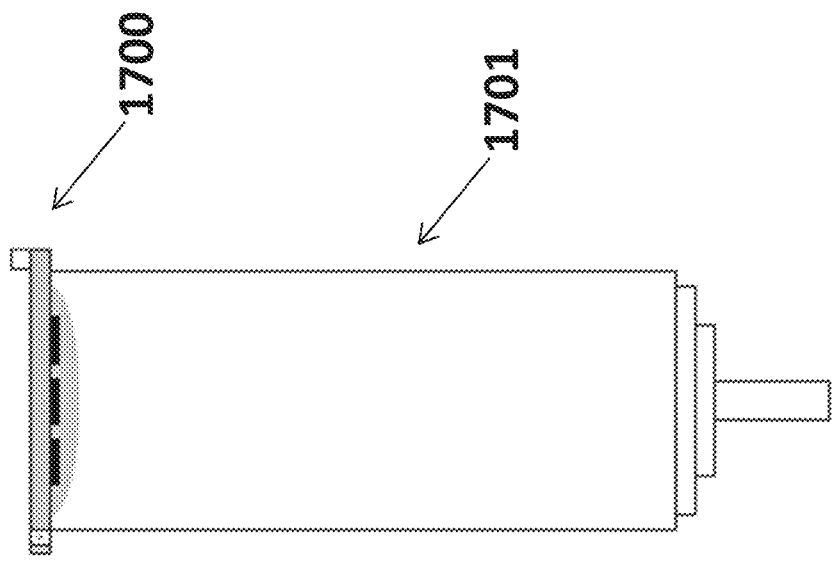

FIGS. 17A-D depict a non-limiting example of a sensor device 1700 that may be suitable for use with an inhaler device. FIG. 17A depicts a top view of the sensor device. The sensor device 1700 may include one or more sensors such as an airflow sensor 1710 (e.g., thermistor) and a touch sensor 1702 (e.g., electrode). The sensor device 1700 may further include one or more indicators, such as a multi-colored LED 1704 for providing a visual indication. The one or more indicators 1704 may be operably coupled to the sensor device 1700 such that when the one or more sensors 1702, 1710 detect a predetermined threshold of one or more parameters of the medicament device, the sensor device 1700 transmits an output to the indicator 1704. The sensor device 1700 may further include one or more contacts for downloading or extracting data from the sensor device 1708. The electronics and working components of the sensor device 1700 may be found in, for example, a raw printed circuit board 1706. FIG. 17B depicts a side view of the sensor device 1700. The sensor device 1700 may include a potting material 1712 to protect and/or hide the electronics and the working components of the sensor device 1700. FIG. 17C depicts a bottom view of the sensor device 1700. The sensor device may include a high-tack adhesive coating 1714, a microcontroller unit (MCU) 1716, an additional sensor such as a shake sensor 1718 (e.g., 3-axis accelerometer), and a power source 1720 (e.g., solid state battery). FIG. 17D depicts an example of the sensor device 1700 affixed to the canister of an inhaler device 1701.

In one example, a user picks up an inhaler device that includes the sensor device affixed to the top of the inhaler device and touches the touch sensor to awaken it. The user next begins to shake the inhaler device if the inhaler device contains a suspension formulation. In some cases, when the user has shaken the inhaler device at the angle, frequency, and duration appropriate for the particular formulation, the sensor device stores the data reflecting the shaking parameters employed by the user and produces an output that indicates by means of an indicator that the inhaler device is ready to be actuated. In one example, the indicator is a light, such as a LED. In one instance, the indicator is a LED light that remains on during the shake-to-fire interval. In another instance, the indicator is a LED light that blinks during the shake-to-fire interval. In some cases, when the sensor device produces an output that indicates by means of an indicator the beginning of the shake-to-fire interval, the user then compresses the inhaler device canister to actuate the inhaler device. In some cases, the sensor device captures and stores the actuation parameter data produced when the user actuates the inhaler device during the shake-to-fire interval. In some cases, when the user has fully compressed the canister, the sensor device produces an output that may be a second indicator to indicate the beginning of the actuation hold time window. In some cases, this indicator is a light, such as a LED. In one instance, the indicator is an LED light that remains on during the actuation hold time window. In another instance, the indicator is an LED light that blinks during the actuation hold time window. In another instance, the output is an indicator that is audible, such as a chirp, a beep, a tone, or a vibration. In some cases, the audible indicator remains on during the actuation hold time window. In some cases, at the end of the actuation hold time window, the sensor device produces an output that indicates by means of an indicator that the inhaler device canister valve has been held open by means of compression for the duration of the actuation hold time window sufficiently long enough to allow for the intended dosage range of a drug to be emitted from the inhaler device. In one instance, this output may be the turning off or absence of the LED light that turned on or blinked during the actuation hold time window. In another instance, this output may be audible, or a turning off or absence of a sound. In another instance, this output may be a vibration or absence of a vibration.

In some cases, the sensor device includes a counter to record the number of times an inhaler device has been actuated. In one example, a user picks up an inhaler device that includes a sensor device affixed to the top of it and touches the sensor device to awaken it. In some cases, the sensor device produces an output that is an indication to indicate that the inhaler device should be primed. In some cases, when the sensor device has not been awakened in a prescribed amount of time, the sensor device produces an output that is an indication to indicate that the inhaler device should be re-primed. In some cases, if the user is holding the inhaler device at an angle or orientation that will negatively impact delivery of the intended dosage range of the drug, such as a user holding the inhaler device upside down, the sensor device produces an output that is an indication to indicate that the user should re-orient the inhaler device. In some cases, the indication produced is visual, audible, or the absence of a visual or audible indicator.

In another example, a user picks up an inhaler device that includes a sensor device affixed to the top of it and touches the sensor device's touch sensor to awaken it. In some cases, the sensor device stores the number of times the inhaler device has been actuated. In some cases, the sensor device produces an output that is an indication to indicate when the inhaler device has expired, should be cleaned, has limited doses remaining, has exceeded the doses available in the device, and any combination of one or more thereof. In some cases, the indication is visible, audible, or a combination thereof. In some cases, the visible indication is a light or the absence of light. In some cases, the indication is a sound or the absence of sound. In some cases, the indication is a vibration or the absence of a vibration.

In some cases, the sensor device's output is data that is collected and stored by the sensor device. In some cases, the data is transmitted to or read from a mobile device, a computer, a cloud application or any combination thereof.

Example 2. Sensor Device for Use with a Nasal Device

A user picks up a nasal spray device that includes the sensor device affixed to the nasal device's bottle, pump, or actuator nozzle tip and touches the touch sensor to awaken it. The user next begins to shake the nasal device if the nasal device contains a suspension formulation. In some cases, when the user has shaken the nasal device at the angle, frequency, and duration appropriate for the particular formulation, the sensor device stores the data reflecting the shaking parameters employed by the user and produces an output that indicates by means of an indicator that the nasal device is ready to be actuated. In some cases, the indicator is a light, such as an LED. In one instance, the indicator is an LED light that remains on during the shake-to-fire interval. In another instance, the indicator is an LED light that blinks during the shake-to-fire interval. In some cases, when the sensor device produces an output that indicates by means of an indicator the beginning of the shake-to-fire interval, the user then compresses the nasal device's pump by pressing on the bottom of the nasal device's bottle relative to the nasal device's nozzle tip to actuate the nasal device. In some cases, the sensor device captures and stores the actuation parameter data produced when the user actuates the nasal device during the shake-to-fire interval. In some cases, when the user has fully compressed the pump, the sensor device produces an output that may be a second indicator to indicate the beginning of the actuation hold time window. In some cases, this indicator is a light, such as an LED. In one instance, the indicator is an LED light that remains on during the actuation hold time window. In another instance, the indicator is an LED light that blinks during the actuation hold time window. In some cases, the output is an indicator that is audible, such as a chirp, a beep, a tone, or a vibration. In some cases, the audible indicator remains on during the actuation hold time window. In some cases, at the end of the actuation hold time window, the sensor device produces an output that indicates by means of an indicator that the nasal device's pump has been held open by means of compression for the duration of the actuation hold time window sufficiently long enough to allow for the intended dosage range of a drug to be emitted from the nasal device. In some cases, this output may be the turning off or absence of the LED light that turned on or blinked during the actuation hold time window. In some cases, this output may be audible, or a turning off or absence of a sound. In some cases, this output may be a vibration or absence of a vibration.

In another example, the sensor device includes a dose counter to record the number of times a nasal device has been actuated. In some cases, a user picks up a nasal spray device that includes a sensor device affixed to the device's bottle, pump, or actuator nozzle tip and touches the sensor device to awaken it. In some cases, the sensor device produces an output that is an indication to indicate that the nasal device should be primed. In some cases, when the sensor device has not been awakened in a prescribed amount of time, the sensor device produces an output that is an indication to indicate that the nasal device should be re-primed. In some cases, if the user is holding the nasal device at an angle or orientation that will negatively impact delivery of the intended dosage range of the drug, such as a user holding the nasal device upside down, the sensor device produces an output that is an indication to indicate that the user should re-orient the nasal device. In some cases, the indication produced is visual, audible, or the absence of a visual or audible indication.

In another example, a user picks up a nasal spray device that includes a sensor device affixed to the nasal device's bottle, pump, or actuator nozzle tip and touches the sensor device to awaken it. In some cases, the sensor device stores the number of times the nasal device has been actuated. In some cases, the sensor device produces an output that is an indication to indicate when the nasal device has expired, should be cleaned, has limited doses remaining, has exceeded the doses available in the nasal device, and any combination of one or more thereof. In some cases, the indication is visible, audible, or a combination thereof. In some cases, the visible indication is a light or the absence of light. In some cases, the indication is a sound or the absence of sound. In some cases, the indication is a vibration or the absence of a vibration.

In some cases, the sensor device's output is data that is collected and stored by the sensor device. In some cases, the data is transmitted to or read from a mobile device, a computer, a cloud application or any combination thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for monitoring usage of a medicament device, the device comprising:
   a) an adapter, wherein the adapter comprises a memory storing a set of parameters specific to a type of the medicament device; and
   b) a sensor device separable from, and in operable communication with the adapter, wherein the sensor device is configured to be used with a plurality of different types of adapters each comprising a unique set of parameters specific to different types of medicament devices; and
   c) optionally, the medicament device,
   wherein the device is configured to produce an output based on the set of parameters,
   wherein the sensor device comprises a pressure sensing cavity comprising a single opening, and
   wherein the adapter comprises a pressure tap tube configured to couple to the single opening.

2. The device of claim 1, wherein the medicament device comprises a canister used with an inhaler.

3. The device of claim 2, wherein the adapter is configured to couple to an exterior of the canister, and wherein the sensor device is configured to couple indirectly to the canister via the adapter.

4. The device of claim 1, wherein the sensor device comprises an accelerometer configured to be located along a central line axis of the medicament device when the adapter and the sensor device is coupled to the medicament device.

5. The device of claim 1, wherein the pressure sensing cavity comprises a barometer.

6. The device of claim 1, wherein the sensor device comprises a receiving port, and wherein the adapter comprises a protrusion complementary to the receiving port.

7. The device of claim 6, wherein the receiving port and the protrusion each comprise an electrical interface.

8. The device of claim 1, wherein the output is a feedback provided to a user based on usage of the medicament device.

9. The device of claim 8, wherein the feedback guides the user on how to properly administer the medicament device in real-time.

10. The device of claim 1, wherein the output is produced when at least one of the set of parameters has met a predetermined threshold or when at least one of the set of parameters is outside a threshold range.

11. The device of claim 1, wherein the sensor device is configured to be operable with one or more different medicament devices.

12. The device of claim 1, wherein the sensor device is reusable.

13. The device of claim 1, wherein the adapter is disposable.

14. The device of claim 1, wherein the set of parameters comprises one or more shake parameters; optionally, wherein the one or more shake parameters is selected from the group consisting of: shake duration, shake angle, shake frequency, shake-to-fire interval, shake orientation, and any combination thereof.

15. The device of claim 1, wherein the set of parameters comprises one or more actuation parameters; optionally, wherein the one or more actuation parameters is selected from the group consisting of: compression velocity, compression acceleration, actuation hold time, decompression velocity, decompression acceleration, actuation stroke length, and any combination thereof.

16. The device of claim 1, wherein the set of parameters comprises one or more inhalation airflow parameters; optionally, wherein the one or more inhalation airflow parameters is selected from the group consisting of: inspiratory airflow rate, inhaled volume, inflow velocity, and any combination thereof.

17. The device of claim 1, wherein the medicament device contains a formulation of a drug, wherein the output is produced when at least one of the set of parameters has met a predetermined threshold, and wherein the predetermined threshold is determined based on a composition of the formulation of a drug, one or more characteristics of the medicament device, or both.

18. The device of claim 1, wherein the adapter is permanently or removably affixed to a housing or a canister of the medicament device.

19. The device of claim 1, wherein the sensor device is affixed to the adapter.

20. The device of claim 1, wherein the output comprises a visual indication, an audible indication or both.

21. The device of claim 1, wherein the output comprises data.

22. The device of claim 21, wherein the data is collected and stored by the device.

23. The device of claim 22, wherein the data is transmitted to or read from a mobile device, a computer, a cloud application, or any combination thereof.

24. The device of claim 1, wherein the one or more sensors is selected from the group consisting of: an accelerometer, a barometer, a temperature sensor, a magnetometer, an ambient light sensor, and a global positioning system (GPS).

25. A kit comprising: the device of claim 1; and instructions for coupling and/or decoupling the sensor device and the adapter to a medicament device selected from a plurality of different types of medicament devices.

* * * * *